(12) United States Patent
Williams et al.

(10) Patent No.: US 7,622,267 B2
(45) Date of Patent: Nov. 24, 2009

(54) LOW-DENSITY LIPOPROTEIN RECEPTOR 6 (LRP6) AS A MAMMARY STEM CELL MARKER AND RELATED METHODS

(75) Inventors: Bart O. Williams, Caledonia, MI (US); Charlotta Lindvall, Grand Rapids, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 77 days.

(21) Appl. No.: 11/755,638

(22) Filed: May 30, 2007

(65) Prior Publication Data

US 2007/0292348 A1    Dec. 20, 2007

Related U.S. Application Data

(60) Provisional application No. 60/809,281, filed on May 30, 2006.

(51) Int. Cl.
    G01N 33/53    (2006.01)
(52) U.S. Cl. ........................................ 435/7.1
(58) Field of Classification Search .................. 435/7.1
    See application file for complete search history.

(56) References Cited

FOREIGN PATENT DOCUMENTS

WO    2006055635 A2    5/2006
WO    2007140410 A2    12/2007

OTHER PUBLICATIONS

Tockman et al (Cancer Res., 1992, 52:2711s-2718s).*
Benhajk et al (Oncology Reports, 2006, 15:701-707).*
Al-Hajj M, et al. Prospective identification of tumorigenic breast cancer cells. Proc Natl Acad Sci 100, No. 7: 3983-3988; (Apr. 1, 2003).
Li Y, et al. Evidence that transgenes encoding components of the Wnt signaling pathway preferentially induce mammary cancers from progenitor cells. Proc Natl Acad Sci 100, No. 26: 15853-15858 (Dec. 23, 2003).
Liu B, et al. The transforming activity of Wnt effectors correlates with their ability to induce the accumulation of mammary progenitor cells. Proc Natl Acad Sci 101, No. 12: 4158-4163 (Mar. 23, 2004).
Reya T, et al. A role for Wnt signalling in self-renewal of haematopoietic stem cells. Nature 423: 409-414 (May 22, 2003).
Shackleton M, et al. Generation of a functional mammary gland from a single stem cell. Nature 439: 84-88 (Jan. 5, 2006).
Stingl J, et al. Purification and unique properties of mammary epithelial stem cells. Nature 439: 993-997 (Feb. 23, 2006).
Veltmaat J, et al. Mouse embryonic mammogenesis as a model for the molecular regulation of pattern formation. Differentiation 71: 1-17 (2003).
Benhaj K, et al. Redundant expression of canonical Wnt ligands in human breast cancer cell lines. Oncology Reports 15: 701-707 (2006).
Katoh M, et al. Cross-talk of WNT and FGF Signaling Pathways at GSK3β to Regulate β-Catenin and SNAIL Signaling Cascades. Cancer Biology & Therapy 5 (No. 9): 1059-1064 (Sep. 2006).
Khan Z, et al. Analysis of Endogenous LRP6 Function Reveals a Novel Feedback Mechanism by Which Wnt Negatively Regulates Its Receptor. Molecular and Cellular Biology 27 (No. 20): 7291-7301 (Oct. 2007).
He X, understanding Wnt/beta-catenin signaling. FASEB J. 20 (Abstract 862.1): A1337 (2006).
Lindvall C, et al. The Wnt Signaling Receptor Lrp5 Is Required for Mammary Ductal Stem Cell Activity and Wnt1-induced Tumorigenesis. The Journal of Biological Chemistry 281 (No. 46): 35081-35087. (Nov. 17, 2006).
Lindvall C, et al. Wnt Signaling, Stem Cells, and the Cellular Origin of Breast Cancer. Stem Cell Rev 3: 157-168 (2007).
Young J, et al. LRP5 and LRP6 Are Not Required for Protective Antigen-Mediated Internalization or Lethality of Anthrax Lethal Toxin. PLoS Pathogens 3 (No. 3): 0287-0295 (Mar. 2007).

* cited by examiner

*Primary Examiner*—Sean E Aeder
(74) *Attorney, Agent, or Firm*—Price, Heneveld, Cooper, DeWitt & Litton, LLP

(57) ABSTRACT

A method for enriching a population of somatic mammary stem cells or mammary tumor stem cells based on low-density lipoprotein receptor-related protein 6 (LRP6). Also included are methods for screening for LRP6 modulators, as well as methods for reducing Wnt signaling, for treating Wnt signaling-related diseases, for detecting mammary basal-like cells, for diagnosing basal-like breast cancer, and for inhibiting proliferation of a tumor expressing LRP6, and compositions thereof.

9 Claims, 15 Drawing Sheets

SEQUENCE LISTING

<160> NUMBER OF SEQ ID NOS: 4

<210> SEQ ID NO 1
<211> LENGTH: 5224
<212> TYPE: DNA
<213> ORGANISM: homo sapiens

<400> SEQUENCE: 1

```
atgggggccg tcctgaggag cctcctggcc tgcagcttct gtgtgctcct gagagcggcc      60
cctttgttgc tttatgcaaa cagacgggac ttgcgattgg ttgatgctac aaatggcaaa     120
gagaatgcta cgattgtagt tggaggcttg gaggatgcag ctgcggtgga ctttgtgttt     180
agtcatggct tgatatactg gagtgatgtc agcgaagaag ccattaaacg aacagaattt     240
aacaaaactg agagtgtgca gaatgttgtt gtttctggat tattgtcccc cgatgggctg     300
gcatgtgatt ggcttggaga aaaattgtac tggacagatt ctgaaactaa tcggattgaa     360
gtttctaatt tagatggatc tttacgaaaa gttttatttt ggcaagagtt ggatcaaccc     420
agagctattg ccttagatcc ttcaagtggg ttcatgtact ggacagactg gggagaagtg     480
ccaaagatag aacgtgctgg aatggatggt tcaagtcgct tcattataat aaacagtgaa     540
atttactggc aaatggact gactttggat tatgaagaac aaaagcttta ttgggcagat     600
gcaaaactta atttcatcca caatcaaat ctggatggaa caaatcggca ggcagtggtt     660
aaaggttccc ttccacatcc tttttgccttg acgttatttg aggacatatt gtactggact     720
gactggagca cacactccat tttggcttgc aacaagtata ctggtgaggg tctgcgtgaa     780
atccattctg acatcttctc tcccatggat atacatgcct tcagccaaca gaggcagcca     840
aatgccacaa atccatgtgg aattgacaat gggggttgtt cccatttgtg tttgatgtct     900
ccagtcaagc ttttttatca gtgtgcttgc cccactgggg tcaaactcct ggagaatgga     960
aaaacctgca aagatggtgc cacagaatta ttgcttttag ctcgaaggac agacttgaga    1020
cgcatttctt tggatacacc agattttaca gacattgttc tgcagttaga agacatccgt    1080
catgccattg ccatagatta cgatcctgtg gaaggctaca tctactggac tgatgatgaa    1140
gtgagggcca tacgccgttc atttatagat ggatctggca gtcagtttgt ggtcactgct    1200
caaattgccc atcctgatgg tattgctgtg gactgggttg cacgaaatct ttattggaca    1260
gacactggca ctgatcgaat agaagtgaca aggctcaatg ggaccatgag gaagatcttg    1320
atttcagagg acttagagga accccgggct attgtgttag atcccatggt tgggtacatg    1380
tattggactg actggggaga aattccgaaa attgagcgag cagctctgga tggttctgac    1440
cgtgtagtat tggttaacac ttctcttggt tggccaaatg gtttagcctt ggattatgat    1500
gaaggcaaaa tatactgggg agatgccaaa acagacaaga ttgaggttat gaatactgat    1560
ggcactggga cgagtactag tggaagac aaaattcctc acatatttgg atttactttg    1620
ttgggtgact atgtttactg gactgactgg cagaggcgta gcattgaaag agttcataaa    1680
cgaagtgcag agagggaagt gatcatagat cagctgcctg acctcatggg cctaaaggct    1740
acaaatgttc atcgagtgat tggttccaac ccctgtgctg aggaaaacgg gggatgtagc    1800
catctctgcc tctatagacc tcagggcctt cgctgtgctt gccctattgg ctttgaactc    1860
atcagtgaca tgaagacctg cattgtccca gaggctttcc ttttgtttc acggagagca    1920
gatatcagac gaatttctct ggaaacaaac aataataatg tggctattcc actcactggt    1980
gtcaaagaag cttctgcttt ggattttgat gtgacagaca accgaattta ttggactgat    2040
```

```
atatcactca agaccatcag cagagccttt atgaatggca gtgcactgga acatgtggta      2100
gaattcggct tagattatcc agaaggcatg gcagtagact ggcttgggaa gaacttgtac      2160
tgggcagaca caggaacgaa tcgaattgag gtgtcaaagt tggatgggca gcaccgacaa      2220
gttttggtgt ggaaagacct agatagtccc agagctctcg cgttggaccc tgccgaagga      2280
tttatgtatt ggactgaatg gggtggaaaa cctaagatag acagagctgc aatggatgga      2340
agtgaacgta ctaccttagt tccaaatgtg gggcgggcaa acggcctaac tattgattat      2400
gctaaaagga ggctttattg gacagacctg gacaccaact aatagaatc ttcaaatatg       2460
cttgggctca accgtgaagt tatagcagat gacttgcctc atccttttgg cttaactcag      2520
taccaagatt atatctactg gacggactgg agccgacgca gcattgagcg tgccaacaaa      2580
accagtggcc aaaaccgcac catcattcag ggccatttgg attatgtgat ggacatcctc      2640
gtctttcact catctcgaca gtcagggtgg aatgaatgtg cttccagcaa tgggcactgc      2700
tcccacctct gcttggctgt gccagttggg ggttttgttt gtggatgccc tgcccactac      2760
tctcttaatg ctgacaacag gacttgtagt gctcctacga cttttcctgct cttcagtcaa      2820
aagagtgcca tcaaccgcat ggtgattgat gaacaacaga gccccgacat catccttccc      2880
atccacagcc ttcggaatgt ccgggccatt gactatgacc cactggacaa gcaactctat      2940
tggattgact cacgacaaaa catgatccga aaggcacaag aagatggcag ccagggcttt      3000
actgtggttg tgagctcagt tccgagtcag aacctggaaa tacaacccta tgacctcagc      3060
attgatattt acagccgcta catctactgg acttgtgagg ctaccaatgt cattaatgtg      3120
acaagattag atgggagatc agttggagtg gtgctgaaag gcgagcagga cagacctcga      3180
gccattgtgg taaacccaga gaagggtat atgtatttta ccaatcttca ggaaaggtct       3240
cctaaaattg aacgggctgc tttggatggg acagaacggg aggtcctctt tttcagtggc      3300
ttaagtaaac caattgcttt agcccttgat agcaggctgg gcaagctctt tgggctgat       3360
tcagatctcc ggcgaattga aagcagtgat ctctcaggtg ctaaccggat agtattagaa      3420
gactccaata tcttgcagcc tgtgggactt actgtgtttg aaaactggct ctattggatt      3480
gataaacagc agcaaatgat tgaaaaaatt gacatgacag gtcgagaggg tagaaccaaa      3540
gtccaagctc gaattgccca gcttagtgac attcatgcag taaaggagct gaaccttcaa      3600
gaatacagac agcacccttg tgctcaggat aatggtggct gttcacatat ttgtcttgta      3660
aaggggatg gtactacaag gtgttcttgc cccatgcacc tggttctact tcaagatgag       3720
ctatcatgtg gagaacctcc aacatgttct cctcagcagt ttacttgttt cacggggaa       3780
attgactgta tccctgtggc ttggcggtgc gatgggttta ctgaatgtga agaccacagt      3840
gatgaactca attgtcctgt atgctcagag tcccagttcc agtgtgccag tgggcagtgt      3900
attgatggtg ccctccgatg caatggagat gcaaactgcc aggacaaatc agatgagaag      3960
aactgtgaag tgctttgttt aattgatcag ttccgctgtg ccaatggtca gtgcattgga      4020
aagcacaaga gtgtgatca taatgtggat tgcagtgaca gtcagatga actggattgt       4080
tatccgactg aagaaccagc accacaggcc accaatacag ttggttctgt tattggcgta      4140
attgtcacca ttttgtgtc tggaactgta tactttatct gccagaggat gttgtgtcca      4200
cgtatgaagg gagatgggga aactatgact aatgactatg tagttcatgg accagcttct      4260
gtgcctcttg gttatgtgcc acacccaagt tctttgtcag atctcttcc aggaatgtct       4320
cgaggtaaat caatgatcag ctccctcagt atcatggggg gaagcagtgg accccctat      4380
```

```
gaccgagccc atgttacagg agcatcatca agtagttctt caagcaccaa aggcacttac    4440
ttccctgcaa ttttgaaccc tccaccatcc ccagccacag agcgatcaca ttacactatg    4500
gaatttggat attcttcaaa cagtccttcc actcataggt catacagcta caggccatat    4560
agctaccggc actttgcacc ccccaccaca ccctgcagca cagatgtttg tgacagtgac    4620
tatgctccta gtcggagaat gacctcagtg gcaacagcca agggctatac cagtgacttg    4680
aactatgatt cagaacctgt gcccccacct cccacacccc gaagccaata cttgtcagca    4740
gaggagaact atgaaagctg cccaccttct ccatacacag agaggagcta ttctcatcac    4800
ctctacccac cgccaccctc tccctgtaca gactcctcct gaggaggggc cctcctcctc    4860
tgactgcctc caacgtaaaa atgtaaatat aaatttggtt gagatctgga ggggggagg    4920 gagctattag agaaggatga ggcagaccat gtacagttaa aattataaaa tggggtaggg    4980
aatactggag atatttgtac agaagaaaag gatatttata tattttctta aaacagcaga    5040
tttgctgctt gtgccataaa agtttgtata aaaaaaattt gtactaaaag ttttattttt    5100
gcaaactaaa tacacaaagc atgccttaaa cccagtgaag caactgagta caaaggaaac    5160
aggaataata aaggcatcac tgaccaggaa tatctgggct ttattgatac caaaaaaaaa    5220
aaaa                                                                 5224

<210> SEQ ID NO 2
<211> LENGTH: 1613
<212> TYPE: PRT
<213> ORGANISM: homo sapiens

<400> SEQUENCE: 2

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220
```

```
Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
            245                 250                 255

Gly Leu Arg Glu Ile His Ser Asp Ile Phe Ser Pro Met Asp Ile His
        260                 265                 270

Ala Phe Ser Gln Gln Arg Gln Pro Asn Ala Thr Asn Pro Cys Gly Ile
    275                 280                 285

Asp Asn Gly Gly Cys Ser His Leu Cys Leu Met Ser Pro Val Lys Pro
290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
            325                 330                 335

Thr Asp Leu Arg Arg Ile Ser Leu Asp Thr Pro Asp Phe Thr Asp Ile
        340                 345                 350

Val Leu Gln Leu Glu Asp Ile Arg His Ala Ile Ala Ile Asp Tyr Asp
    355                 360                 365

Pro Val Glu Gly Tyr Ile Tyr Trp Thr Asp Asp Glu Val Arg Ala Ile
370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
        405                 410                 415

Leu Tyr Trp Thr Asp Thr Gly Thr Asp Arg Ile Glu Val Thr Arg Leu
    420                 425                 430

Asn Gly Thr Met Arg Lys Ile Leu Ile Ser Glu Asp Leu Glu Glu Pro
        435                 440                 445

Arg Ala Ile Val Leu Asp Pro Met Val Gly Tyr Met Tyr Trp Thr Asp
450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
            485                 490                 495

Leu Asp Tyr Asp Glu Gly Lys Ile Tyr Trp Gly Asp Ala Lys Thr Asp
        500                 505                 510

Lys Ile Glu Val Met Asn Thr Asp Gly Thr Gly Arg Arg Val Leu Val
    515                 520                 525

Glu Asp Lys Ile Pro His Ile Phe Gly Phe Thr Leu Leu Gly Asp Tyr
530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
            565                 570                 575

Gly Leu Lys Ala Thr Asn Val His Arg Val Ile Gly Ser Asn Pro Cys
        580                 585                 590

Ala Glu Glu Asn Gly Gly Cys Ser His Leu Cys Leu Tyr Arg Pro Gln
    595                 600                 605

Gly Leu Arg Cys Ala Cys Pro Ile Gly Phe Glu Leu Ile Ser Asp Met
610                 615                 620

Lys Thr Cys Ile Val Pro Glu Ala Phe Leu Leu Phe Ser Arg Arg Ala
625                 630                 635                 640
```

```
Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Glu Phe Gly Leu
    690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
                740                 745                 750

Leu Ala Leu Asp Pro Ala Glu Gly Phe Met Tyr Trp Thr Glu Trp Gly
                755                 760                 765

Gly Lys Pro Lys Ile Asp Arg Ala Ala Met Asp Gly Ser Glu Arg Thr
                770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
                820                 825                 830

Pro His Pro Phe Gly Leu Thr Gln Tyr Gln Asp Tyr Ile Tyr Trp Thr
                835                 840                 845

Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
                900                 905                 910

Val Cys Gly Cys Pro Ala His Tyr Ser Leu Asn Ala Asp Asn Arg Thr
                915                 920                 925

Cys Ser Ala Pro Thr Thr Phe Leu Leu Phe Ser Gln Lys Ser Ala Ile
    930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
                980                 985                 990

Gln Glu Asp Gly Ser Gln Gly Phe Thr Val Val Ser Ser Val Pro
            995                 1000                1005

Ser Gln Asn Leu Glu Ile Gln Pro Tyr Asp Leu Ser Ile Asp Ile
        1010                1015                1020

Tyr Ser Arg Tyr Ile Tyr Trp Thr Cys Glu Ala Thr Asn Val Ile
        1025                1030                1035

Asn Val Thr Arg Leu Asp Gly Arg Ser Val Gly Val Val Leu Lys
        1040                1045                1050

Gly Glu Gln Asp Arg Pro Arg Ala Ile Val Val Asn Pro Glu Lys
```

```
                1055                1060                1065
Gly Tyr Met Tyr Phe Thr Asn Leu Gln Glu Arg Ser Pro Lys Ile
        1070                1075                1080
Glu Arg Ala Ala Leu Asp Gly Thr Glu Arg Glu Val Leu Phe Phe
        1085                1090                1095
Ser Gly Leu Ser Lys Pro Ile Ala Leu Ala Leu Asp Ser Arg Leu
        1100                1105                1110
Gly Lys Leu Phe Trp Ala Asp Ser Asp Leu Arg Arg Ile Glu Ser
        1115                1120                1125
Ser Asp Leu Ser Gly Ala Asn Arg Ile Val Leu Glu Asp Ser Asn
        1130                1135                1140
Ile Leu Gln Pro Val Gly Leu Thr Val Phe Glu Asn Trp Leu Tyr
        1145                1150                1155
Trp Ile Asp Lys Gln Gln Gln Met Ile Glu Lys Ile Asp Met Thr
        1160                1165                1170
Gly Arg Glu Gly Arg Thr Lys Val Gln Ala Arg Ile Ala Gln Leu
        1175                1180                1185
Ser Asp Ile His Ala Val Lys Glu Leu Asn Leu Gln Glu Tyr Arg
        1190                1195                1200
Gln His Pro Cys Ala Gln Asp Asn Gly Gly Cys Ser His Ile Cys
        1205                1210                1215
Leu Val Lys Gly Asp Gly Thr Thr Arg Cys Ser Cys Pro Met His
        1220                1225                1230
Leu Val Leu Leu Gln Asp Glu Leu Ser Cys Gly Glu Pro Pro Thr
        1235                1240                1245
Cys Ser Pro Gln Gln Phe Thr Cys Phe Thr Gly Glu Ile Asp Cys
        1250                1255                1260
Ile Pro Val Ala Trp Arg Cys Asp Gly Phe Thr Glu Cys Glu Asp
        1265                1270                1275
His Ser Asp Glu Leu Asn Cys Pro Val Cys Ser Glu Ser Gln Phe
        1280                1285                1290
Gln Cys Ala Ser Gly Gln Cys Ile Asp Gly Ala Leu Arg Cys Asn
        1295                1300                1305
Gly Asp Ala Asn Cys Gln Asp Lys Ser Asp Glu Lys Asn Cys Glu
        1310                1315                1320
Val Leu Cys Leu Ile Asp Gln Phe Arg Cys Ala Asn Gly Gln Cys
        1325                1330                1335
Ile Gly Lys His Lys Lys Cys Asp His Asn Val Asp Cys Ser Asp
        1340                1345                1350
Lys Ser Asp Glu Leu Asp Cys Tyr Pro Thr Glu Glu Pro Ala Pro
        1355                1360                1365
Gln Ala Thr Asn Thr Val Gly Ser Val Ile Gly Val Ile Val Thr
        1370                1375                1380
Ile Phe Val Ser Gly Thr Val Tyr Phe Ile Cys Gln Arg Met Leu
        1385                1390                1395
Cys Pro Arg Met Lys Gly Asp Gly Glu Thr Met Thr Asn Asp Tyr
        1400                1405                1410
Val Val His Gly Pro Ala Ser Val Pro Leu Gly Tyr Val Pro His
        1415                1420                1425
Pro Ser Ser Leu Ser Gly Ser Leu Pro Gly Met Ser Arg Gly Lys
        1430                1435                1440
Ser Met Ile Ser Ser Leu Ser Ile Met Gly Gly Ser Ser Gly Pro
        1445                1450                1455
```

-continued

```
Pro Tyr Asp Arg Ala His Val Thr Gly Ala Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 3
<211> LENGTH: 5440
<212> TYPE: DNA
<213> ORGANISM: mus musculus

<400> SEQUENCE: 3
ggcggcggca tggggcagg cgctggcgtc gcgcgagccc gggccggagc ggcgcgctag      60
agccctgacg tgcgcccttt tctttcttct cgcggccgcg gaaagcatga gcgtgcagac     120
ccgccgctgc ggcggccgcc ccggctcctc gcccgcgcgt ccctggccg ccgggcgccg     180 gtgagggccg cgagcgcgcg cggtggtggg gggaagatgg gggccgtgct gaggagcctc     240
ctggcctgca gcttctgcgt gctgctgaga gcggcccctt tgttgcttta tgcaaacaga     300
cgggacttga gattggttga tgctacaaat ggcaaagaga atgcaacgat gtagttgga      360 ggcttggagg atgcagctgc ggtggacttt gtgtttggtc atggcttgat atactggagt     420
gatgtcagcg aagaagccat taaacgaaca gaatttaaca aaactgaaag tgtacagaat     480
gttgttgttt ctggattatt gtccccggat gggctggcat gtgattggct tggagaaaaa     540
ttgtactgga cagattctga actaatcgt attgaagttt ctaatttaga tggatcttta     600
cgaaaagttt tattttggca agagttggat caacccagag ctattgcctt agatccatca     660
agtgggttca tgtactggac agactgggga gaagtgccaa agataacg tgctgggatg      720 gatggctcaa gtcgcttcgt tataataaac acagagattt actggccaaa cggactgact     780
ctggactatc aggagcggaa gctttactgg gccgatgcaa aacttaattt catccataaa     840
tcaaacctgg atgaacaaa ccggcaggca gtggttaaag gttcccttcc acatcctttt     900
gccttgacgt tatttgagga cacattgtac tggactgact ggaatacaca ctctattttg     960
gcttgcaaca aatatactgg cgagggtctg cgtgaaattc attctaacat cttctctccc    1020
atggatatac atgctttcag ccaacagagg cagccaaatg ctacaaatcc atgtggaatt    1080
gataatggtg gttgttccca tttgtgtttg atgtctccag tcaagccttt ttatcagtgt    1140
```

```
gcttgcccaa ctggggtcaa gctgctggag aatggaaaga cctgcaaaga tggtgccact    1200
gaactattgc tgttagcccg acggacagac ttgaggcgaa tttctttgga tacacccgat    1260
tttactgaca ttgttctgca gttagaagat atccggcatg ccattgccat agactatgac    1320
cctgtagaag gctacatata ctggacggat gacgaagtga gggctatccg tcgctccttc    1380
atagatggat ctgcagtca gtttgtggtc acggcccaga ttgctcatcc tgatggtatt    1440
gctgttgact gggttgcaag gaacctgtac tggacagaca ctggcacgga tcgtatagaa    1500
gtgacaaggc tcaatgggac catgaggaag atcttgattt cagaggactt agaggagccc    1560
cgggctatcg tgttagatcc catggttggg tacatgtatt ggacagactg gggagaaatc    1620
ccaaaaatag agcgagctgc tctggacgga tctgaccgag tagttcttgt caacacttcc    1680
cttggttggc caaacggctt agccctggat tatgatgaag gcacaatata ctggggagat    1740
gccaaaacag acaaaattga ggttatgaat accgatggca ccgggaggcg agtgctggtg    1800
gaagacaaga tccctcacat atttgggttt accttgctgg gtgactatgt ttactggact    1860
gactggcaga ggcggagcat cgagagagta cacaaacgga gcgcagagag ggaggtcatc    1920
atagatcagc tgccagacct catgggactg aaggccacaa gtgttcacag aatcattggt    1980
tctaacccct gtgctgagga caatggagga tgtagccatc tttgcctgta caggcctcag    2040
gggcttcgat gcgcctgtcc cattggcttt gagctcatca gtgacatgaa gacatgcatt    2100
gtccccgagg ctttccttct gttctcgagg agagcggata tcagacgcat atctttggaa    2160
acaaacaaca acaatgtggc cattcctctc actggtgtca agaagcctc tgctttggat    2220 tttgatgtca cagacaacag gatttactgg actgatatat cactgaagac tattagcaga    2280
gcctttatga atggcagtgc actggaacat gtggtagagt ttggcttaga ttatccagaa    2340
ggcatggcag tggactggct tgggaagaac ttatactggg cagacacagg aacaaatcgc    2400
attgaggtat cgaagttgga cggacagcac cgacaggttt ggtatgaa agaccttgac    2460 agtcctcgag ctctggcact ggatcctgct gaagggttta tgtattggac tgagtgggga    2520
ggcaagccta agattgacag ggctgctatg atggaagtg aacgcactac attagttcca    2580
aatgtaggcc gagcaaatgg tctcaccatc gactatgcta aaaggcggct ttactggaca    2640
gacctggaca ctaacctaat agaatcctca gatatgctcg gactcaaccg tgaagttata    2700
gcagatgact tgcctcatcc tttttggctta actcagtacc aagattacat ctactggaca    2760
gactggagcc gacgcagcat tgaacgtgcc aacaaaacca gtggccaaaa ccgcaccatc    2820
atccagggcc atttggacta tgtgatggac atcctggtct tccactcttc ccggcaggca    2880
gggtggaatg agtgtgcctc cagcaacggg cactgctccc acctctgctt ggctgtgccc    2940
gtcggaggtt ttgtgtgtgg atgccctgcc cactactccc tgaatgctga caacaggacc    3000
tgcagtgctc ccaccacctt cctgctcttc agtcagaaga gcgccatcaa ccgcatggtg    3060
attgatgaac aacagagccc tgacatcatc cttcctatcc acagccttcg gaacgtccgg    3120
gccattgact atgacccttt ggacaagcag ctctactgga ttgactctcg acaaaactcc    3180
atacgaaagg cacatgaaga tggtggccag ggttttaatg tagttgcaaa ctcagtcgca    3240
aatcagaacc ttgaaataca gccctatgat ctcagcattg atatttatag ccgttacatc    3300
tactggacct gtgaagctac caatgtcatt gatgtgacga gattagatgg acgatcagtt    3360
ggagtggttc taaaaggcga gcaagacaga cctcgagcca ttgtggtaaa ccccgagaaa    3420
gggtatatgt attttaccaa tcttcaggaa agatctccta aaaattgaacg gctgcattg    3480
```

```
gatggtacag aacgagaggt cctctttttc agtggcttaa gtaaaccaat tgctttggct    3540
cttgatagca agctgggcaa gctcttctgg gctgactcag atctccggcg aattgaaagc    3600
agtgatctct caggtgccaa caggatcgtg ctagaagact ctaatatatt acagcctgtg    3660
ggcctgaccg tgtttgaaaa ctggctctat tggattgata acagcagca gatgattgaa    3720
aaaattgaca tgactggtcg agaaggaaga accaaggtcc aggctcgaat tgctcagctg    3780
agtgacatcc atgcagtaaa ggagctgaac cttcaggagt acagacagca cccttgtgcc    3840
caggataatg gtggctgttc acatatctgc cttgtaaaag gagatggtac gacaagatgc    3900
tcctgcccca tgcacttagt tctgcttcag gatgagctgt cctgtggaga gcctccaacg    3960
tgttctcctc agcagtttac ctgcttcact ggggacattg actgcatccc tgtggcttgg    4020
cggtgtgatg ggtcactga gtgcgaagac acagcgatg aactcaattg tcccgtgtgc    4080
tcagagtctc agttccagtg tgccagcggg cagtgcattg atggtgccct cgatgcaat    4140
ggcgatgcga actgccagga caaatcagat gagaagaact gtgaagtgct ttgtttaatt    4200
gatcagttcc gctgtgccaa tggtcagtgc gttggaaagc acaagaaatg tgaccacagt    4260
gtggactgca gtgacagatc tgacgagctg actgttatc caactgagga gccagcacca    4320
caagccacca acacagttgg ttctgttatt ggagtaattg tcaccatttt tgtgtctgga    4380
accatatact ttatctgcca gaggatgctg tgtcctcgta tgaagggaga cggggagacc    4440
atgactaacg actatgtggt tcacagcccg gcgtctgtgc cccttggtta tgttcctcac    4500
ccaagctctc tctctggatc tcttccagga atgtctcgag gcaaatcaat gatcagttcc    4560
ctcagtatca tgggggaag cagtgggccc cctatgatc gagcgcacgt cacgggagcc    4620
tcctcaagca gttcttccag taccaaaggc acttacttcc ctgcaatttt gaacccacca    4680
ccatcgcctg ccacagaaag atcccattat accatggaat ttggttattc ttccaacagt    4740
ccttccacac ataggtccta cagctatagg ccgtacagct accggcactt tgcaccgccc    4800
accacaccct gcagcactga tgtctgtgac agtgactatg ctcctagccg gaggatgacc    4860
tcggtggcaa cagccaaggg ctacaccagt gacgtgaact atgactcaga acctgtgccc    4920
ccaccgccca caccccgaag ccagtacttg tcagcggagg agaactatga aagctgcccc    4980
ccttccccat acacggagag gagttactcc caccacctct acccgccacc accctccccc    5040
tgcacggact cctcctgagg agggcccctc ctcctctgac tgcctccacc gggacatgta    5100
aatacacatc tggttgagat ctggaggggg ggagggagct atagagaaga gtgaggcaga    5160
ctctgtacag ttaacattat aaagtgggtg ggtgctggaa atatttgtac agaagaaaag    5220
aatatttata tattttctta aaacagcagt tttgctgctt gtgccataaa agtttgtata    5280
aaaaataaat ttgtactaaa agtttttattt ttgcaaacta atacacaga gcatgcctta    5340
agcccagtga agagactgag tacaaaggaa acaggaaaag aaaggcatca ctgaccagga    5400
gtgtctgggt tttaacgata ccaaaaaaaa aaaaaaaaa                           5440
```

<210> SEQ ID NO 4
<211> LENGTH: 1613
<212> TYPE: PRT
<213> ORGANISM: mus musculus

<400> SEQUENCE: 4

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

```
Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Gly His Gly Leu
    50                  55                  60

Ile Tyr Trp Ser Asp Val Ser Glu Glu Ala Ile Lys Arg Thr Glu Phe
65                  70                  75                  80

Asn Lys Ser Glu Ser Val Gln Asn Val Val Ser Gly Leu Leu Ser
                85                  90                  95

Pro Asp Gly Leu Ala Cys Asp Trp Leu Gly Lys Leu Tyr Trp Thr
                100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Val Ile
                165                 170                 175

Ile Asn Thr Glu Ile Tyr Trp Pro Asn Gly Leu Thr Leu Asp Tyr Gln
                180                 185                 190

Glu Arg Lys Leu Tyr Trp Ala Asp Ala Lys Leu Asn Phe Ile His Lys
    195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Thr Leu Tyr Trp Thr
225                 230                 235                 240

Asp Trp Asn Thr His Ser Ile Leu Ala Cys Asn Lys Tyr Thr Gly Glu
                245                 250                 255

Gly Leu Arg Glu Ile His Ser Asn Ile Phe Ser Pro Met Asp Ile His
            260                 265                 270

Ala Phe Ser Gln Gln Arg Gln Pro Asn Ala Thr Asn Pro Cys Gly Ile
    275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Met Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
    355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
        435                 440                 445
```

```
Arg Ala Ile Val Leu Asp Pro Met Val Gly Tyr Met Tyr Trp Thr Asp
    450                 455                 460
Trp Gly Glu Ile Pro Lys Ile Glu Arg Ala Ala Leu Asp Gly Ser Asp
465                 470                 475                 480
Arg Val Val Leu Val Asn Thr Ser Leu Gly Trp Pro Asn Gly Leu Ala
                485                 490                 495
Leu Asp Tyr Asp Glu Gly Thr Ile Tyr Trp Gly Asp Ala Lys Thr Asp
            500                 505                 510
Lys Ile Glu Val Met Asn Thr Asp Gly Thr Gly Arg Arg Val Leu Val
        515                 520                 525
Glu Asp Lys Ile Pro His Ile Phe Gly Phe Thr Leu Leu Gly Asp Tyr
    530                 535                 540
Val Tyr Trp Thr Asp Trp Gln Arg Arg Ser Ile Glu Arg Val His Lys
545                 550                 555                 560
Arg Ser Ala Glu Arg Glu Val Ile Ile Asp Gln Leu Pro Asp Leu Met
                565                 570                 575
Gly Leu Lys Ala Thr Ser Val His Arg Val Ile Gly Ser Asn Pro Cys
            580                 585                 590
Ala Glu Asp Asn Gly Gly Cys Ser His Leu Cys Leu Tyr Arg Pro Gln
        595                 600                 605
Gly Leu Arg Cys Ala Cys Pro Ile Gly Phe Glu Leu Ile Gly Asp Met
    610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Asn Val Ala Ile
                645                 650                 655
Pro Leu Thr Gly Val Lys Glu Ala Ser Ala Leu Asp Phe Asp Val Thr
            660                 665                 670
Asp Asn Arg Ile Tyr Trp Thr Asp Ile Ser Leu Lys Thr Ile Ser Arg
        675                 680                 685
Ala Phe Met Asn Gly Ser Ala Leu Glu His Val Val Glu Phe Gly Leu
    690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
            740                 745                 750
Leu Ala Leu Asp Pro Ala Glu Gly Phe Met Tyr Trp Thr Glu Trp Gly
        755                 760                 765
Gly Lys Pro Lys Ile Asp Arg Ala Ala Met Asp Gly Ser Glu Arg Thr
    770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asp Met Leu Gly Leu Asn Arg Glu Val Ile Ala Asp Asp Leu
            820                 825                 830
Pro His Pro Phe Gly Leu Thr Gln Tyr Gln Asp Tyr Ile Tyr Trp Thr
        835                 840                 845
Asp Trp Ser Arg Arg Ser Ile Glu Arg Ala Asn Lys Thr Ser Gly Gln
    850                 855                 860
Asn Arg Thr Ile Ile Gln Gly His Leu Asp Tyr Val Met Asp Ile Leu
```

-continued

```
        865                 870                 875                 880
    Val Phe His Ser Ser Arg Gln Ala Gly Trp Asn Glu Cys Ala Ser Ser
                        885                 890                 895

Asn Gly His Cys Ser His Leu Cys Leu Ala Val Pro Val Gly Gly Phe
                    900                 905                 910

Val Cys Gly Cys Pro Ala His Tyr Ser Leu Asn Ala Asp Asn Arg Thr
                    915                 920                 925

Cys Ser Ala Pro Ser Thr Phe Leu Leu Phe Ser Gln Lys Ser Ala Ile
                    930                 935                 940

Asn Arg Met Val Ile Asp Glu Gln Gln Ser Pro Asp Ile Ile Leu Pro
    945                 950                 955                 960

Ile His Ser Leu Arg Asn Val Arg Ala Ile Asp Tyr Asp Pro Leu Asp
                    965                 970                 975

Lys Gln Leu Tyr Trp Ile Asp Ser Arg Gln Asn Ser Ile Arg Lys Ala
                    980                 985                 990

His Glu Asp Gly Gly Gln Gly Phe Asn Val Val Ala Asn Ser Val Ala
                995                 1000                1005

Asn Gln Asn Leu Glu Ile Gln Pro Tyr Asp Leu Ser Ile Asp Ile
            1010                1015                1020

Tyr Ser Arg Tyr Ile Tyr Trp Thr Cys Glu Ala Thr Asn Val Ile
            1025                1030                1035

Asp Val Thr Arg Leu Asp Gly Arg Ser Val Gly Val Val Leu Lys
            1040                1045                1050

Gly Glu Gln Asp Arg Pro Arg Ala Ile Val Val Asn Pro Glu Lys
            1055                1060                1065

Gly Tyr Met Tyr Phe Thr Asn Leu Gln Glu Arg Ser Pro Lys Ile
            1070                1075                1080

Glu Arg Ala Ala Leu Asp Gly Thr Glu Arg Glu Val Leu Phe Phe
            1085                1090                1095

Ser Gly Leu Ser Lys Pro Ile Ala Leu Ala Leu Asp Ser Lys Leu
            1100                1105                1110

Gly Lys Leu Phe Trp Ala Asp Ser Asp Leu Arg Arg Ile Glu Ser
            1115                1120                1125

Ser Asp Leu Ser Gly Ala Asn Arg Ile Val Leu Glu Asp Ser Asn
            1130                1135                1140

Ile Leu Gln Pro Val Gly Leu Thr Val Phe Glu Asn Trp Leu Tyr
            1145                1150                1155

Trp Ile Asp Lys Gln Gln Gln Met Ile Glu Lys Ile Asp Met Thr
            1160                1165                1170

Gly Arg Glu Gly Arg Thr Lys Val Gln Ala Arg Ile Ala Gln Leu
            1175                1180                1185

Ser Asp Ile His Ala Val Lys Glu Leu Asn Leu Gln Glu Tyr Arg
            1190                1195                1200

Gln His Pro Cys Ala Gln Asp Asn Gly Gly Cys Ser His Ile Cys
            1205                1210                1215

Leu Val Lys Gly Asp Gly Thr Thr Arg Cys Ser Cys Pro Met His
            1220                1225                1230

Leu Val Leu Leu Gln Asp Glu Leu Ser Cys Gly Glu Pro Pro Thr
            1235                1240                1245

Cys Ser Pro Gln Gln Phe Thr Cys Phe Thr Gly Asp Ile Asp Cys
            1250                1255                1260

Ile Pro Val Ala Trp Arg Cys Asp Gly Phe Thr Glu Cys Glu Asp
            1265                1270                1275
```

```
His Ser Asp Glu Leu Asn Cys Pro Val Cys Ser Glu Ser Gln Phe
    1280            1285            1290

Gln Cys Ala Ser Gly Gln Cys Ile Asp Gly Ala Leu Arg Cys Asn
    1295            1300            1305

Gly Asp Ala Asn Cys Gln Asp Lys Ser Asp Glu Lys Asn Cys Glu
    1310            1315            1320

Val Leu Cys Leu Ile Asp Gln Phe Arg Cys Ala Asn Gly Gln Cys
    1325            1330            1335

Val Gly Lys His Lys Lys Cys Asp His Ser Val Asp Cys Ser Asp
    1340            1345            1350

Arg Ser Asp Glu Leu Asp Cys Tyr Pro Thr Glu Glu Pro Ala Pro
    1355            1360            1365

Gln Ala Thr Asn Thr Val Gly Ser Val Ile Gly Val Ile Val Thr
    1370            1375            1380

Ile Phe Val Ser Gly Thr Ile Tyr Phe Ile Cys Gln Arg Met Leu
    1385            1390            1395

Cys Pro Arg Met Lys Gly Asp Gly Glu Thr Met Thr Asn Asp Tyr
    1400            1405            1410

Val Val His Ser Pro Ala Ser Val Pro Leu Gly Tyr Val Pro His
    1415            1420            1425

Pro Ser Ser Leu Ser Gly Ser Leu Pro Gly Met Ser Arg Gly Lys
    1430            1435            1440

Ser Met Ile Ser Ser Leu Ser Ile Met Gly Gly Ser Ser Gly Pro
    1445            1450            1455

Pro Tyr Asp Arg Ala His Val Thr Gly Ala Ser Ser Ser Ser Ser
    1460            1465            1470

Ser Ser Thr Lys Gly Thr Tyr Phe Pro Ala Ile Leu Asn Pro Pro
    1475            1480            1485

Pro Ser Pro Ala Thr Glu Arg Ser His Tyr Thr Met Glu Phe Gly
    1490            1495            1500

Tyr Ser Ser Asn Ser Pro Ser Thr His Arg Ser Tyr Ser Tyr Arg
    1505            1510            1515

Pro Tyr Ser Tyr Arg His Phe Ala Pro Pro Thr Thr Pro Cys Ser
    1520            1525            1530

Thr Asp Val Cys Asp Ser Asp Tyr Ala Pro Ser Arg Arg Met Thr
    1535            1540            1545

Ser Val Ala Thr Ala Lys Gly Tyr Thr Ser Asp Val Asn Tyr Asp
    1550            1555            1560

Ser Glu Pro Val Pro Pro Pro Pro Thr Pro Arg Ser Gln Tyr Leu
    1565            1570            1575

Ser Ala Glu Glu Asn Tyr Glu Ser Cys Pro Pro Ser Pro Tyr Thr
    1580            1585            1590

Glu Arg Ser Tyr Ser His His Leu Tyr Pro Pro Pro Ser Pro
    1595            1600            1605

Cys Thr Asp Ser Ser
    1610
```

LOW-DENSITY LIPOPROTEIN RECEPTOR 6 (LRP6) AS A MAMMARY STEM CELL MARKER AND RELATED METHODS

This application claims the benefit of U.S. Patent Application No. 60/809,281, filed on May 30, 2006, which is herein incorporated by reference in its entirety.

BACKGROUND OF THE INVENTION

The Mammary Gland and its Development

The mammary gland is a compound tubulo-alveolar gland composed of a series of branched ducts that, during lactation, drain sac-like alveoli (lobules). In humans, the mammary epithelium is embedded within a fibrous, fatty connective tissue. The mammary epithelium is composed of two lineages of epithelial cells: the luminal cells (which make milk during lactation) and basal positioned myoepithelial cells. Generation and maintenance of the mammary epithelium is via the somatic mammary stem cell. Currently, there is no single cell surface biomarker available that allows substantial enrichment of somatic mammary stem cells. All known enrichment protocols rely on combinations of cell surface markers.

During embryonic development, mammogenesis begins at E10.5 in mice [Veltmaat, J. et al. 2003. Differentiation 71: 1-17]. The mammary gland is derived from both the ectoderm and the mesoderm. Mammary development specifically commences with an increase in quantity of ectodermal cells. The cells form a mammary band and then rapidly multiply and differentiate through mammary streak, line, crest, and hillock stages until they finally form the murine mammary bud at E12-13.5 [Veltmaat, J. et al. 2003. Differentiation 71:1-17]. The mammary bud is the structure from which the mammary gland develops and activation of the canonical Wnt pathway causes localization of the mammary bud and the mammary fat pad precursor [Chu, E. et al. 2004. Development 131:4819-4829].

At E14 the mesenchyme, which has developed from the mesoderm, condenses and forms the fat pad precursor. At E15.5 each bud forms a sprout which invades the subcutaneous fat pad precursor. The sprouts form a lumen with an opening on the skin of the fetus and a nipple forms by epidermal invagination. Additionally, the sprouts continue their development by forming limited branches into the fat pad. At day 18.5 the sprouts have formed small mammary glands [Veltmaat, J. et al. 2003. Differentiation 71:1-17].

By birth, the mammary gland is composed of a few rudimentary ducts, containing an outer layer of myoepithelial and an inner layer of luminal epithelial cells, surrounded by the fat pad. Upon exposure to increased female sexual hormones at puberty, the ductal epithelium rapidly proliferates, elaborates its branching pattern and further invades the fat pad to create a mature mammary gland competent to respond to signals during pregnancy when the epithelium further proliferates and differentiates [Hennighausen, L. et al. 1998. Genes Dev 12:449-455]. Indeed, the sprouts of embryonic development have formed a simple mammary gland which is composed of many hollow ducts each ending in a terminal end bud (TEB). While the female is pregnant and while the female is lactating, these TEBs continue the growth of the simple mammary gland, increasing the branching of the gland, and ultimately increasing the number of alveoli in the breast tissue. When the growth of each simple mammary gland is completed, the fat pad of the breast is fully filled by the ductal trees of the simple mammary glands. The mammary gland is considered mature following this final growth during pregnancy and lactation and the complex mammary gland is composed of many simple mammary glands as a group.

The lumen of the duct is lined with luminal epithelial cells near the TEB and with ductal epithelial cells in the milk ducts. At the end of each mature branch, lobular cells form secretory acinar structures which become the milk secreting alveolar cells during pregnancy [Woodward, W. et al. 2005. J Cell Sci. 118:3585-3594].

The massive expansion of mammary epithelium during puberty and pregnancy, together with the remarkable regenerative capacity apparent during successive reproductive cycles, implicate the existence of a mammary stem cell. In fact, stem-like cells from mature mammary glands have been isolated and their ability to reconstitute the different epithelial lineages in vitro and functional ductal trees through limiting dilution transplants in vivo has been demonstrated [Shackleton, M., Vaillant, F., Simpson, K. J., Stingl, J., Smyth, G. K., Asselin-Labat, M. L., Wu, L., Lindeman, G. J., and Visvader, J. E. (2006), Nature 439, 84-88; Stingl, J., Eirew, P., Ricketson, I., Shackleton, M., Vaillant, F., Choi, D., Li, H. I., and Eaves, C. J. (2006), Nature 439, 993-997]. However, the signals that regulate mammary stem cells have yet not been defined.

The Role of the Wnt Pathway

Wnts are cysteine-rich glycoproteins that initiates signals by binding to a protein complex containing a member of the Frizzled family of seven transmembrane receptors and a molecule with homology to the low-density lipoprotein (LDL) receptor (LRP5 or LRP6) [Logan, C. Y. and R. Nusse, Annu Rev Cell Dev Biol, 2004. 20:781-810]. This down-regulates glycogen synthase kinase-3 (GSK-3) activity. Normally, GSK-3 phosphorylates β-catenin, marking it for ubiquitin-dependent degradation. Inhibition of GSK-3 increases β-catenin levels in the cytosol and nucleus, allowing physical interaction with the Tcf/Lef class of DNA-binding proteins and activation of specific target promoters [Logan, C. Y. and R. Nusse, Annu Rev Cell Dev Biol, 2004. 20:781-810]. Wnt proteins are a family of highly conserved secreted growth factors [Miller, J. R., 2002. Genome Biol. 3:3001]. Although Fzd proteins have been implicated in other pathways, recent work shows that LRP5 and LRP6 are specifically required for the canonical Wnt pathway [Liu, G., et al., 2005, Mol Cell Biol 25:3475-3482].

LRP5 and LRP6 are 71% identical and homologous to the low-density lipoprotein receptor (LDLR) [Brown, S. D., et al., Biochem Biophys Res Commun, 1998. 248(3): p. 879-88; Chen, D., W. Lathrop, and Y. Dong, Genomics, 1999. 55(3): 314-21; Dong, Y., et al., Biochem Biophys Res Commun, 1998. 251(3):784-90; Hey, P. J., et al., Gene, 1998. 216(1): 103-11].

Several reports link LRP5 and LRP6 to Wnt signaling. First, LRP6-deficient mice display phenotypes similar to those seen in several Wnt gene knockouts [Pinson, K. I., et al., Nature, 2000. 407(6803):535-8]. In addition, arrow, the *Drosophila* homolog of LRP5 and LRP6, is required for Wnt signaling in the fly [Wehrli, M., et al., Nature, 2000. 407 (6803):527-30]. mRNA encoding LRP6 induces a secondary axis when injected into the ventral region of the developing *Xenopus* embryo [Tamai, K., et al., Nature, 2000. 407(6803): p. 530-5]. LRP5 mRNA synergizes with mRNAs from other components of the pathway to induce a secondary axis, but was unable to do so on its own. Frizzleds and LRP6 form a physical complex in a Wnt-dependent manner [Tamai, K., et al., Nature, 2000. 407(6803):530-5].

The Dickkopf (Dkk) family of secreted proteins is an antagonist of the canonical Wnt pathway [Bafico, A. et al. 2001, Nat Cell Biol 3:683-686.; Mao, B. et al. 2001, Nature 411:321-325]. Specifically, Dkk-1, Dkk-2, or Dkk-4 competitively inhibits Wnt signaling through the binding of LRP5 or LRP6 and Kremen cell surface receptors. Mice overexpressing Dkk1 in the skin also fail to develop mammary glands [Andl, T., et al., Dev Cell, 2002. 2(5):643-53]. Dkk1 inhibits the Wnt signaling pathway by binding to, and presumably inactivating, LRP5 and LRP6.

In addition, other proteins regulate the activity of the Wnt pathway at several levels.

Secreted Frizzled-related proteins (SFRPs) or FRZBs as well as other secreted proteins like Norrin, connective tissue growth factor and Kremen regulate signaling at the level of the Wnt/Frizzled/LRP interaction, while other proteins, including APC, control the pathway intracellularly [Finch, P. W., et al., Proc Natl Acad Sci U S A, 1997. 94(13):6770-5; Wang, S., M. Krinks, and M. Moos, Jr., Biochem Biophys Res Commun, 1997. 236(2):502-4, Xu, Q., et al., Cell, 2004. 116(6): 883-95], Dickkopf [Semenov, M. V., et al., Curr Biol, 2001. 11(12):951-61; Mao, B., et al., Nature, 2001. 411(6835):321-5], Wise [Itasaki, N., et al., Development, 2003. 130(18):4295-305], connective tissue growth factor [Mercurio, S., et al., Development, 2004. 131(9):2137-47], and Kremen [Mao, B., et al., Nature, 2002. 417(6889):664-7; Logan, C. Y. and R. Nusse, Annu Rev Cell Dev Biol, 2004. 20:781-810].

Signaling by the Wnt family of secreted lipoproteins plays a central role in development and disease [Cadigan, K. M., and Nusse, R. (1997), Wnt signaling: a common theme in animal development. Genes Dev 11, 3286-3305; Nusse, R. (2005), Cell Res 15, 28-32; Polakis, P. (2000), Genes Dev 14, 1837-1851]. At the cellular level, Wnt proteins regulate a broad range of functions including self-renewal and differentiation of stem cells [Li, L., and Xie, T. (2005), Annu Rev Cell Dev Biol 21, 605-631; Reya, T., Duncan, A. W., Ailles, L., Domen, J., Scherer, D. C., Willert, K., Hintz, L., Nusse, R., and Weissman, I. L. (2003), Nature 423, 409-414]. Activation of the canonical Wnt cascade is initiated by binding of Wnt proteins to cell surface receptors composed of a member of the Frizzled (Fzd) protein family and one of the Low-density lipoprotein receptor-related proteins LRP5 or LRP6 [Schweizer, L., and Varmus, H. (2003), BMC Cell Biol 4, 4; Sharpe, C., Lawrence, N., and Martinez Arias, A. (2001), Bioessays 23, 311-318]. The cDNA and amino acid sequences for LRP6 for *Homo sapiens* are attached hereto as SEQ ID NOS.: 1 and 2 in the Sequence Listing. The cDNA and amino acid sequences for LRP6 for *mus musculus* are attached hereto as SEQ ID NOS.: 3 and 4 in the Sequence Listing. While Wnt-Frizzled interactions may also be involved in noncanonical Wnt signaling events, the LRP5/6 moiety appears to be specifically required for the canonical pathway [Liu, G., Bafico, A., and Aaronson, S. A. (2005). Mol Cell Biol 25, 3475-3482].

Studies in mice suggest that canonical Wnt signaling plays a significant role during normal mammary gland development which begins at approximately embryonic day 10.5 with the formation of two "mammary lines" [Andl, T., Reddy, S. T., Gaddapara, T., and Millar, S. E. (2002), Dev Cell 2, 643-653; Brisken, C., Heineman, A., Chavarria, T., Elenbaas, B., Tan, J., Dey, S. K., McMahon, J. A., McMahon, A. P., and Weinberg, R. A. (2000), Genes Dev 14, 650-654; Hsu, W., Shakya, R., and Costantini, F. (2001), J Cell Biol 155, 1055-1064; Tepera, S. B., McCrea, P. D., and Rosen, J. M. (2003), J Cell Sci 116, 1137-1149; van Genderen, C., Okamura, R. M., Farinas, I., Quo, R. G., Parslow, T. G., Bruhn, L., and Grosschedl, R. (1994), Genes Dev 8, 2691-2703; Veltmaat, J. M., Mailleux, A. A., Thiery, J. P., and Bellusci, S. (2003), Differentiation 71, 1-17]. In response to signals from the underlying mesenchyme, the mammary lines give rise to five pairs of lens-shaped mammary placodes which subsequently transform into buds of epithelial cells and sink into the dermis. Activation of the canonical Wnt signaling pathway along the mammary lines coincides with the initiation of mammary morphogenesis, and subsequently localizes to mammary placodes and buds [Chu, E. Y., Hens, J., Andl, T., Kairo, A., Yamaguchi, T. P., Brisken, C., Glick, A., Wysolmerski, J. J., and Millar, S. E. (2004), Development 131, 4819-4829]. Several Wnt ligands and receptor genes, including LRP6 (Is this correct), are expressed during embryonic mammary morphogenesis [Chu, E. Y., Hens, J., Andl, T., Kairo, A., Yamaguchi, T. P., Brisken, C., Glick, A., Wysolmerski, J. J., and Millar, S. E. (2004), Development 131, 4819-4829]. Embryos expressing the canonical Wnt inhibitor Dkk1 display a complete block in the formation of mammary placodes and mice deficient for Lef-1 fail to maintain their mammary buds [Andl, T., Reddy, S. T., Gaddapara, T., and Millar, S. E. (2002), Dev Cell 2, 643-653; van Genderen, C., Okamura, R. M., Farinas, I., Quo, R. G., Parslow, T. G., Bruhn, L., and Grosschedl, R. (1994), Genes Dev 8, 2691-2703] suggesting that Wnt signals might regulate embryonic mammary development. Dkk1 inhibits the Wnt signaling pathway by binding to, and presumably inactivating, LRP5 and LRP6 [Bafico, A., Liu, G., Yaniv, A., Gazit, A., and Aaronson, S. A. (2001), Nat Cell Biol 3, 683-686].

In addition to playing a key role in normal embryonic development, the Wnt pathway later plays a significant role in somatic stem cell renewal and determination [Li, L., et al. 2005. Stem cell niche: structure and function. Annu Rev Cell Dev Biol 21:605-631; Reya, T. et al. 2003, Nature 423:409-414]. Based on what pathway they are active in, Wnt proteins are divided into two types: canonical and noncanonical. Wnts classified as canonical include, but are not limited to Wnt1, Wnt2, Wnt3, Wnt3a, and Wnt8 [Liu, G. et al. 2005, Mol Cell Biol 25:3475-3482].

Tissue specific stem cell compartments, including that of the mammary gland, are formed during embryogenesis [Li, L., and Xie, T. (2005), Annu Rev Cell Dev Biol 21, 605-631]. Analysis of transgenic mice carrying the TOPGAL or BATgal Wnt reporter gene shows that canonical Wnt signaling is specifically active during embryonic mammary development [Chu, E. Y., Hens, J., Andl, T., Kairo, A., Yamaguchi, T. P., Brisken, C., Glick, A., Wysolmerski, J. J., and Millar, S. E. (2004), Development 131, 4819-4829], and its requirement is acute as mammary placodes fail to develop in transgenic mice overexpressing the Wnt inhibitor Dkk1 [Andl, T., Reddy, S. T., Gaddapara, T., and Millar, S. E. (2002), Dev Cell 2, 643-653].

Outgrowth of a full mammary branching tree from limiting dilutions of mammary epithelial cell transplants is considered to be an assay of clonal stem cell function [Kordon, E. C., and Smith, G. H. (1998), Development 125, 1921-1930]. Surgical removal of the area between the nipple and the fat pad at three weeks of age leaves a fat pad free of the endogeneous mammary epithelium. Mammary cells from another syngenic animal can be implanted and will develop an epithelial tree if the transplant contains cells with stem cell activity. One benefit of this technique is that the transplanted cells are exposed to normal circulating hormone levels and wild type stroma.

Canonical Wnt signaling has emerged as a critical regulatory pathway for stem cells. The association between ectopic activation of Wnt signaling and many different types of human cancer suggests that Wnt ligands can initiate tumor formation through altered regulation of stem cell populations.

Tumors induced by Wnt effectors are normally composed of both epithelial and myoepithelial cells, suggesting that they are derived from the transformation of multi-potential progenitor cells [Li, Y., Welm, B., Podsypanina, K., Huang, S., Chamorro, M., Zhang, X., Rowlands, T., Egeblad, M., Cowin, P., Werb, Z., et al. (2003), Proc Natl Acad Sci U S A 100, 15853-15858; Liu, B. Y., McDermott, S. P., Khwaja, S. S., and Alexander, C. M. (2004), Proc Natl Acad Sci U S A 101, 4158-4163; Owens, D. M., and Watt, F. M. (2003), Nat Rev Cancer 3, 444-451; Rosner, A., Miyoshi, K., Landesman-Bollag, E., Xu, X., Seldin, D. C., Moser, A. R., MacLeod, C. L., Shyamala, G., Gillgrass, A. E., and Cardiff, R. D. (2002), Am J Pathol 161, 1087-1097].

A growing body of evidence suggests that specific subtypes of the most common human tumors including breast [Al-Hajj, M., Wicha, M. S., Benito-Hemandez, A., Morrison, S. J., and Clarke, M. F. (2003), Proc Natl Acad Sci U S A 100, 3983-3988], lung [Kim, C. F., Jackson, E.

L., Woolfenden, A. E., Lawrence, S., Babar, I., Vogel, S., Crowley, D., Bronson, R. T., and Jacks, T. (2005), Cell 121, 823-835] and colon [Radtke, F., and Clevers, H. (2005), Science 307, 1904-1909] originate in stem cell compartments. Signaling pathways that regulate stem cell activity could therefore be effective drug targets. In fact, several studies have shown that activation of canonical Wnt signaling is common in human breast cancer [Lin, S. Y., Xia, W., Wang, J. C., Kwong, K. Y., Spohn, B., Wen, Y., Pestell, R. G., and Hung, M. C. (2000), Proc Natl Acad Sci U S A 97, 4262-4266; Ugolini, F., Charafe-Jauffret, E., Bardou, V. J., Geneix, J., Adelaide, J., Labat-Moleur, F., Penault-Llorca, F., Longy, M., Jacquemier, J., Birnbaum, D., and Pebusque, M. J. (2001), Oncogene 20, 5810-5817; Klopocki, E., Kristiansen, G., Wild, P. J., Klaman, I., Castanos-Velez, E., Singer, G., Stohr, R., Simon, R., Sauter, G., Leibiger, H., et al. (2004), Int J Oncol 25, 641-649].

A connection between mammary stem/progenitor cells and Wnt1- or β-catenin-induced tumorigenesis has recently been established. Transgenic expression of these genes result in widespread mammary hyperplasia and rapid tumor formation [Imbert, A., Eelkema, R., Jordan, S., Feiner, H., and Cowin, P. (2001), J Cell Biol 153, 555-568; Nusse, R., and Varmus, H. E. (1982), Cell 31, 99-109; Tsukamoto, A. S., Grosschedl, R., Guzman, R. C., Parslow, T., and Varmus, H. E. (1988), Cell 55, 619-625]. The hyperplastic tissue contains an increased ratio of mammary stem/progenitor cells which are thought to directly give rise to transformed cells [Li, Y., Welm, B., Podsypanina, K., Huang, S., Chamorro, M., Zhang, X., Rowlands, T., Egeblad, M., Cowin, P., Werb, Z., et al. (2003), Proc Natl Acad Sci U S A 100, 15853-15858; Liu, B. Y., McDermott, S. P., Khwaja, S. S., and Alexander, C. M. (2004), Proc Natl Acad Sci U S A 101, 4158-4163; Shackleton, M., Vaillant, F., Simpson, K. J., Stingl, J., Smyth, G. K., Asselin-Labat, M. L., Wu, L., Lindeman, G. J., and Visvader, J. E. (2006), Nature 439, 84-88]. Tumors arising from stem/progenitor cells often show mixed lineage differentiation [Owens, D. M., and Watt, F. M. (2003), Nat Rev Cancer 3, 444-451] and tumors induced by Wnt effectors indeed contain cells from both epithelial lineages [Li, Y., Welm, B., Podsypanina, K., Huang, S., Chamorro, M., Zhang, X., Rowlands, T., Egeblad, M., Cowin, P., Werb, Z., et al. (2003), Proc Natl Acad Sci U S A 100, 15853-15858; Liu, B. Y., McDermott, S. P., Khwaja, S. S., and Alexander, C. M. (2004), Proc Natl Acad Sci U S A 101, 4158-4163; Rosner, A., Miyoshi, K., Landesman-Bollag, E., Xu, X., Seldin, D. C., Moser, A. R., MacLeod, C. L., Shyamala, G., Gillgrass, A. E., and Cardiff, R. D. (2002), Am J Pathol 161, 1087-1097].

Alterations in Wnt signaling occur in many human tumors [Taipale, J. and P. A. Beachy, Nature, 2001. 411(6835):349-54]. These changes increase the cytoplasmic level of β-catenin. This can occur via loss of both copies of the *adenomatous polyposis coli* (APC) gene. APC was first identified as a gene mutated in families in which individuals develop hundreds of colon polyps, some of which undergo malignant transformation [Polakis, P., Biochim Biophys Acta, 1997. 1332(3): F127-47]. At the cellular level, loss of APC function inhibits β-catenin degradation [Polakis, P., Genes Dev, 2000. 14(15): 1837-51]. Thus, β-catenin levels increase and eventually cause excess target gene activation. Loss-of-function mutations in the axin or conductin genes are associated with hepatocellular and colorectal carcinomas [Satoh, S., et al., Nature Genetics, 2000. 24: p. 245-250; Liu, W., et al., Nat Genet, 2000. 26(2):146-7]. Many human tumors contain alterations in β-catenin, typically point mutations in the GSK3 phosphorylation sites that produce a protein that cannot be degraded [Polakis, P., Current Opinion in Genetics and Development, 1999. 9:15-21]. Moreover, several human tumor types contain alterations in Wnt signaling for which the underlying mutation is undefined (for example, see [Rimm, D. L., et al., Am J Pathol, 1999. 154(2):325-9].

The association of inappropriate Wnt signaling and mammary tumorigenesis has been appreciated since the cloning of Wntl as a gene whose expression was up-regulated by mouse mammary tumor virus (MMTV) integrations [Nusse, R. and H. E. Varmus, Cell, 1982. 31(1):99-109]Alterations of several other genes in the pathway have also been associated with mammary pathology. For example, as many as 45% of breast fibromatosis cases examined in one study contained activating mutations in β-catenin [Abraham, S. C., et al., Hum Pathol, 2002. 33(1):39-46]. Fibromatosis are benign stromal lesions in the breast. A more direct link to breast carcinoma is that the large majority of human breast tumors overexpress cytoplasmic and nuclear levels of β-catenin, a hallmark of activation of the canonical Wnt signaling pathway [Lin, S. Y., et al., Proc Natl Acad Sci U S A, 2000. 97(8):4262-6; Ryo, A., et al., Nat Cell Biol, 2001. 3(9):793-801]. Activation of the pathway is one of the more common events associated with human breast cancer. For example, many human breast tumors up-regulate Pin1, which inhibits β-catenin degradation by preventing its association with APC [Ryo, A., et al., Nat Cell Biol, 2001. 3(9): p. 793-801; Wulf, G. M., et al., Embo J, 2001. 20(13):3459-72]. Another recent report links amplification and overexpression of Dishevelledl, a positively acting component of the pathway upstream of GSK3, to breast cancer [Nagahata, T., et al., Cancer Sci, 2003. 94(6): 515-8]. Further reinforcing the importance of Wnt signaling in breast cancer, a recent report has linked down-regulation of the secreted Wnt inhibitors sFRP1 to breast cancer [Ugolini, F., et al., Oncogene, 2001. 20(41): p. 5810-7; Klopocki, E., et al., Int J Oncol, 2004. 25(3):641-9] and Wif1 [Wissmann, C., et al., J Pathol, 2003. 201(2):204-12].

Aberrant canonical Wnt activation in somatic stem cells has been associated with a variety of diseases in addition to breast cancer. Activating mutations have been identified in both ovarian and breast carcinomas [Bafico, A. et al. 2004. Cancer Cell 6:497-505], hepatocellular carcinoma, hepatoblastoma, gastric carcinoma, melanoma, prostate cancer, thyroid carcinoma, medulloblastoma, and Wilm's tumor [Li, Y. et al. 2005. Future Oncol 1:673-681]. Additionally, the canonical Wnt pathway has been implicated in adenomas, pliomatricomas, and trichofolliculomas [Reya, T. et al. 2005. Nature 434:843-850]. Finally, aberrant canonical Wnt expression has been involved in neurodegeneration [Caricasole, A. et al. 2005. Biosci Rep 25:309-327], as in Alzheimer's disease and Parkinson's disease.

Tumors induced by Wnt effectors ultimately arise within a context of widespread mammary hyperplasia that is noticeable as early in development as embryonic day 18 [Tsukamoto, A. S., Grosschedl, R., Guzman, R. C., Parslow, T., and Varmus, H. E. (1988), Cell 55, 619-625]. The hyperplastic mammary tissue of Wnt1 transgenic mice contains an increased ratio of mammary progenitor cells [Li, Y., Welm, B., Podsypanina, K., Huang, S., Chamorro, M., Zhang, X., Rowlands, T., Egeblad, M., Cowin, P., Werb, Z., et al. (2003), Proc Natl Acad Sci U S A 100, 15853-15858; Liu, B. Y., McDermott, S. P., Khwaja, S. S., and Alexander, C. M. (2004), Proc Natl Acad Sci U S A 101, 4158-4163; Shackleton, M., Vaillant, F., Simpson, K. J., Stingl, J., Smyth, G. K., Asselin-Labat, M. L., Wu, L., Lindeman, G. J., and Visvader, J. E. (2006), Nature 439, 84-88]. These progenitor cells are thought to directly give rise to transformed cells.

Branching complexity of adult mice is a function of terminal end bud (TEB) activity during juvenile ductal extension. TEBs normally disappear when the ductal tree is fully branched and fill the fat pad.

Canonical Wnt signaling has been implicated in the regulation of various stem cells including hematopoietic, intestinal and epidermal stem cells [Reya, T., and Clevers, H. (2005), Nature 434, 843-850]. For example, soluble Wnt proteins promote growth and inhibit differentiation of hematopoietic stem cells [Reya, T., Duncan, A. W., Ailles, L., Domen, J., Scherer, D. C., Willert, K., Hintz, L., Nusse, R., and Weissman, I. L. (2003), Nature 423, 409-414]. Wnt signaling also inhibits differentiation of stem cells in the intestinal epithelium and in hair follicles [Huelsken, J., Vogel, R., Erdmann, B., Cotsarelis, G., and Birchmeier, W. (2001), Cell 105, 533-545; Korinek, V., Barker, N., Moerer, P., van Donselaar, E., Huls, G., Peters, P. J., and Clevers, H. (1998), Nat Genet 19, 379-383; van de Wetering, M., Sancho, E., Verweij, C., de Lau, W., Oving, I., Hurlstone, A., van der Horn, K., Batlle, E., Coudreuse, D., Haramis, A. P., et al. (2002), Cell 111, 241-250]. Importantly, in many of the same tissues where the Wnt cascade controls stem cells, deregulation of Wnt signaling leads to tumor formation. Stabilization of β-catenin in the intestinal epithelium or overexpression of β-catenin in the epidermis result in the development of intestinal adenomas and hair tumors, respectively [Dietrich, W. F., Lander, E. S., Smith, J. S., Moser, A. R., Gould, K. A., Luongo, C., Borenstein, N., and Dove, W. (1993), Cell 75, 631-639; Gat, U., DasGupta, R., Degenstein, L., and Fuchs, E. (1998), Cell 95, 605-614]. This suggests that Wnt ligands can initiate tumor formation through altered regulation of stem cell populations. Consistently, mice that overexpress Wnt signaling effectors in the mammary epithelium develop tumors with stem/progenitor cell properties, in contrast to mice overexpressing several other oncogenes [Li, Y., Welm, B., Podsypanina, K., Huang, S., Chamorro, M., Zhang, X., Rowlands, T., Egeblad, M., Cowin, P., Werb, Z., et al. (2003), Proc Natl Acad Sci U S A 100, 15853-15858]. The preneoplastic hyperplasia contain an increased ratio of cells positive for various mammary progenitor cell markers and the likelihood of progression to carcinoma correlates with the overall number of progenitor cells [Li, Y., Welm, B., Podsypanina, K., Huang, S., Chamorro, M., Zhang, X., Rowlands, T., Egeblad, M., Cowin, P., Werb, Z., et al. (2003), Proc Natl Acad Sci U S A 100, 15853-15858; Liu, B. Y., McDermott, S. P., Khwaja, S. S., and Alexander, C. M. (2004), Proc Natl Acad Sci U S A 101, 4158-4163) (Shackleton, M., Vaillant, F., Simpson, K. J., Stingl, J., Smyth, G. K., Asselin-Labat, M. L., Wu, L., Lindeman, G. J., and Visvader, J. E. (2006), Nature 439, 84-88]. In addition, mammary ductal cells from preneoplastic Wnt1 transgenic mice exhibit an increase ability to reconstitute ductal trees in limiting dilution experiments [Liu, B. Y., McDermott, S. P., Khwaja, S. S., and Alexander, C. M. (2004), Proc Natl Acad Sci U S A 101, 4158-4163; Shackleton, M., Vaillant, F., Simpson, K. J., Stingl, J., Smyth, G. K., Asselin-Labat, M. L., Wu, L., Lindeman, G. J., and Visvader, J. E. (2006), Nature 439, 84-88], a method employed to test the frequency and division potential of ductal stem cells. This finding again demonstrates the ability of the Wnt pathway to target stem cells for transformation, possibly reflecting a role of the Wnt pathway in the self-renewal of normal breast epithelium.

The Cancer Stem Cell Model for Carcinogenesis.

For decades, oncologists have focused on developing therapeutic approaches that shrink tumor mass [Reya, T., et al., Nature, 2001. 414(6859):105-11]. Unfortunately, while many treatments could dramatically shrink tumors initially, recurrence of the initial tumor is common. Recently, a new model has been proposed that may explain these observations [Reya, T., et al., Nature, 2001. 414(6859):105-11]. This "cancer stem cell" model postulates that, in many cases, the cell that is transformed is a cell with pluripotent capabilities. The phenotypic manifestation seen in the tumor is mostly the result of cells that have differentiated from the transformed pluripotent cells. Treatments that shrink the majority of the tumor by attacking the differentiated cells may not affect the small population of pluripotent cells that actually give rise to the tumor. Thus, the tumor recurs and eventually becomes resistant to any known treatment, leading to metastatic progression and, ultimately, the death of the patient. Thus, what is needed to increase success in treating cancer are therapies that target the stem cells within the tumor. Thus, various investigations have been undertaken to examine targeting stem cells as a therapy for cancer. [Yilmaz, O. H., Valdez, R., Theisen, B. K., Guo, W., Ferguson, D. O., Wu, H., Morrison, S. J., Nature, 2006; 1-8; Rossi, D. J., Weissman, I. L., Cell, April 21, 2006; 125:229-231].

Mammary malignancies have been shown to have a stem cell component that propagates the tumor (Al-Hajj M et al. Proc Natl Acad Sci USA 2003,100:3983-8). Thus, cell surface markers for mammary tumor stem cells are of great value in targeting the stem cell population of a mammary tumor. The strong association between Wnt signaling and stem cell regulation is of importance to targeting stem cells within tumors. Activation of the Wnt signaling pathway is associated with expansion of the hematopoietic stem cell compartment, maintenance of muscle stem cells, and regulation of stem cells in the skin [Willert, K., et al., Nature, 2003. 423(6938): p. 448-52; Reya, T., et al., Nature, 2003. 423(6938):409-14; Polesskaya, A., P. Seale, and M. A. Rudnicki, Cell, 2003. 113(7):841-52; Alonso, L. and E. Fuchs, Genes Dev, 2003. 17(10):1189-200; Merrill, B. J., et al., Genes Dev, 2001. 15(13):1688-705]. Reports link Wnt signaling to the regulation of mammary stem cells [Li, Y., et al., Proc Natl Acad Sci U S A, 2003. 100(26):15853-8; Liu, B. Y., et al., Proc Natl Acad Sci USA, 2004. 101(12):4158-63]. Overall, the present disclosure has identified Wnt signaling as a key to maintaining pluripotency, and the role of LRP6 in Wnt signaling in cancer stem cells and carcinogenesis, particularly as it relates to breast cancers involving basal-like cells.

SUMMARY OF THE INVENTION

The present invention includes a method for enriching a population of somatic mammary cells or mammary tumor cells for mammary stem cells or mammary tumor stem cells using low density lipoprotein-receptor-related protein 6 (LRP6) as a cell surface marker. This method includes obtaining said population, contacting said population with an anti-LRP6 antibody, and selecting the cells that bind the LRP6 antibody. In other embodiments, the population of mammary cells or mammary tumor cells is a population of human, mouse, or rat cells; the antibody is attached to a solid matrix; cells that bind to the antibody are selected by flow cytometry; the top 10% or higher of the highest LRP6 expressing mammary cells or mammary tumor cells of the total population is selected; or the method is for enriching a population of mammary cells for somatic mammary stem cells. In further embodiments, the method also includes the step of contacting the population of mammary cells with an antibody against a cell surface marker for endothelial cells, hematopoietic cells, or stromal cells wherein cells that bind to the anti-LRP6 antibody but not the antibody against the cell surface marker for endothelial cells, hematopoietic cells, or stromal cells are selected; at least 1% of the selected cells are somatic mammary stem cells; or at least 5% of the selected cells are somatic mammary stem cells.

The present invention also includes a method of screening for agents that modulate Wnt signaling in mammary tumor stem or progenitor cells including: providing a mammary cell that has low density lipoprotein receptor-related protein 6 (LRP6) activity and attenuated low density lipoprotein receptor-related protein 5 (LRP5) activity; selecting an agent that may be an LRP6 modulator; exposing the cell to the agent; performing an assay on the cell for LRP6 activity; and concluding from the assay whether Wnt signaling is modulated in the mammary cell. In other embodiments: the cell is an LRP5 knock-out cell; the selected agent inhibits LRP6, is an RNAi for LRP6, is an antibody for LRP6, or is an antibody for LRP6 carrying a toxic moiety; or the LRP6 activity is determined by measuring the level of LRP6 mRNA or protein, by measuring the level or activity of GSK3, by measuring the level of β-catenin, or by measuring the activity of a Wnt pathway responsive promoter.

The present invention further includes a composition for reducing Wnt signaling in a cancer stem cell or progenitor cell utilizing a compound to inhibit LRP6 activity in a cancer stem cell or progenitor cell. In one embodiment of the composition, the compound inactivates LRP6 in the cancer stem cell or progenitor cell. In another embodiment the compound is an RNAi for LRP6. In a further embodiment, the mammary tumor cells or progenitor cells are basal-like cells. In further embodiments of the present invention, the compound is an antibody for LRP6, or such antibody carrying a toxic moiety.

The present invention further includes a method of reducing Wnt signaling in a cancer stem cell or progenitor cell in a mammal comprising administering to the mammal an effective amount of a cancer stem cell-specific or progenitor cell-specific LRP6 antagonist. In another embodiment of this method, the cancer stem cell-specific or progenitor cell-specific LRP6 antagonist inactivates LRP6 in cancer stem cells or progenitor cells in the mammal. In a further method of the present invention, the cancer stem cell-specific or progenitor cell-specific LRP6 antagonist is an RNAi for LRP6. In another embodiment, the mammary tumor stem cell or progenitor cell is a basal-like cell. In further embodiments of the present method, the cancer stem cell-specific or progenitor cell-specific LRP6 antagonist is an antibody for LRP6, or such LRP6 antibody carries a toxic moiety.

The present invention also includes a method of treating a condition or disease associated with Wnt signaling comprising administering a pharmaceutical compound that inhibits LRP6 in a cancer stem cell or progenitor cell of a patient. In another embodiment, the compound is administered in an amount effective to reduce Wnt activity. In further embodiments of the present method, the pharmaceutical compound is an RNAi for LRP6, an shRNA for LRP6, an antibody specific to LRP6, or an antibody specific to LRP6 carrying a toxic moiety. The present invention further includes a method for inhibiting the proliferation or causing the death of a mammary tumor cell that expresses LRP6 by contacting the mammary tumor cell with an agent that inhibits LRP6 activity in an amount sufficient to inhibit the proliferation or cause the death of the mammary tumor cell. In additional embodiments, the mammary tumor cell is in a mammal and the step of contacting is carried out by administering the agent to the mammal; a second tumor therapeutic agent is administered; the agent that inhibits LRP6 activity is selected from an anti-LRP6 antibody, an antisense oligonucleotide that inhibits the expression of LRP6, and an RNAi molecule that inhibits the expression of LRP6; or the anti-LRP6 antibody is linked to a cytotoxic agent. In a further embodiment, the mammary tumor cell is a basal-like cell.

The present invention also includes a method for detecting the presence of mammary basal-like cells in mammary tissue or a biological sample, which tissue or sample is suspected of including mammary basal-like cells, comprising the steps of: (a) contacting the tissue or sample with a diagnostically labeled LRP6 antibody; and (b) detecting the presence of the diagnostic label associated with the tissue or sample. Further embodiments of this method include contacting and detecting in vitro; contacting in vivo and detecting in vitro; and contacting and detecting in vivo. In other embodiments, the detectable label is a radionuclide, the detecting is by radioimmunoscintigraphy, or the diagnostic label is an MRI-imageable agent and the detecting is by MRI.

A further aspect of the present invention includes a method for diagnosing basal-like cell breast cancer comprising the steps of: (a) contacting a tissue, organ or sample of a patient with a diagnostically labeled LRP6 antibody; (b) detecting the presence of the diagnostic label associated with the tissue, organ or sample; (c) determining the level of Lrp6 expression in the tissue, organ or sample; and (d) comparing the Lrp6 level of expression in the tissue, organ or sample to a suitable control. In an additional embodiment, the suitable control is the median or average expression level from at least 25 breast cancer patients.

BRIEF DESCRIPTION OF THE DRAWINGS

FIG. 2A is staining of a wild-type control mammary gland (no β-gal activity). FIGS. 2B-2D are staining from LRP6$^{+/-}$ gland at various ages (β-gal expression is derived from the endogenous LRP6 locus.) FIG. 2B is an adult 11-week-old virgin female. FIG. 2C is a 5-week-old female. FIG. 2D is a female in the 12th day of pregnancy. The inset in FIG. 2C shows localization of B-gal in the myoepithelial layer (arrow) after paraffin sectioning of the whole mounts, and the stem cell population is located in the myoepithelial layer.

FIG. 4B is the inventors' FACS sort, 34,500 events. The luminal cells are located in the R3 fraction (left-circled portion) and the myoepithelial cells are located in the R2 fraction (right circled-portion). LRP6 is expressed in the MRU fraction of the myoepithelial cells (FIG. 4C; R2). Only LRP6 expressing cells are shown.

FIG. 7A shows representative whole mount preparations (stained with carmine to reveal the ductal tree) are shown for juvenile Lrp6+/+ (left panel) and Lrp6+/− (right panel) female mice.

The arrows indicate typical terminal end buds. LN, lymph node. FIG. 7B shows the result of morphometric analysis of the average number of TEBs at 5 weeks. In Lrp6+/− females the number of TEBs is reduced by 32% (p=3.8×10$^{-6}$, 2-tailed t test assuming unequal variances) compared to Lrp6+/+ littermate controls.

As shown in FIG. 8A, data are plotted as the proportion of mice in each of the three genotypes remaining tumor-free as a function of days of age.

DETAILED DESCRIPTION OF THE PREFERRED EMBODIMENTS

Figure 1:
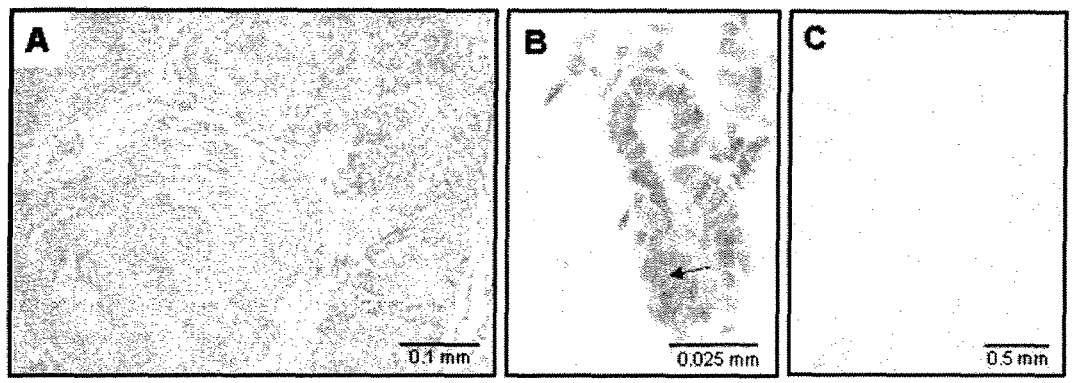
FIGS. 1A-C: LRP6 is expressed in MMTV-Wnt1 transgenic mammary glands and tumors. Shown in panels A-C are immunohistochemical staining using an LRP6 specific polyclonal antibody. LRP6 is expressed in Wnt1-induced tumors (FIG. 1A) and Wnt1-induced tumors originate from the stem cell compartment. LRP6 is also shown expressed in a fraction of mammary ductal cells from hyperplastic Wnt1 transgenic mammary gland (FIG. 1B). The arrow indicates a representative cell with positive staining. No staining was observed in LRP6$^{-/-}$ embryos, which were used as negative controls since LRP6$^{-/-}$ pups die shortly after birth (FIG. 1C).

The preferred embodiments of the present invention may be understood more readily by reference to the following detailed description of the specific embodiments and the Examples and Sequence Listing included hereafter.

The text file filed concurrently with this application, titled "VAN67P380.txt" contains material identified as SEQ ID NO: 1-4, which material is incorporated herein by reference. This text file was created on May 30, 2007, and is 45,056 bytes.

As used herein, "antibody" means an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The term "antibody" includes bivalent or bispecific molecules, diabodies, triabodies, and tetrabodies. Bivalent and bispecific molecules are described in, e.g., Kostelny et al. J Immunol 1992, 148:1547, Pack and Pluckthun Biochemistry 1992, 31:1579, Zhu et al. Protein Sci 1997, 6:781, Hu et al. Cancer Res. 1996, 56:3055, Adams et al. Cancer Res. 1993, 53:4026, and McCartney, et al. Protein Eng. 1995, 8:301. The term "antibody" also includes antigen binding forms of antibodies, including fragments with antigen-binding capability (e.g., Fab', F(ab')$_2$, Fab, Fv and rIgG) and recombinant single chain Fv fragments (scFv). Antibodies exist, e.g., as intact immunoglobulins or as a number of well-characterized fragments produced by digestion with various peptidases. Thus, for example, pepsin digests an antibody below the disulfide linkages in the hinge region to produce F(ab)'.sub.2, a dimer of Fab which itself is a light chain joined to V.sub.H-C.sub.H1 by a disulfide bond. The F(ab)'.sub.2 may be reduced under mild conditions to break the disulfide linkage in the hinge region, thereby converting the F(ab)'.sub.2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Preferably, antibodies employed to practice the present invention bind to a selected target antigen on the surface of a cell with an affinity (association constant) of greater than or equal to $10^7$ $M^{-1}$. When an antibody is referred to as specific for a particular antigen, it means that the binding reaction is determinative of the presence of the antigen in a heterogeneous population of proteins and other biologics. Thus, under suitable conditions, the specified antibodies bind to a particular protein sequences at least two times the background and more typically more than 10 to 100 times the background.

As used herein, the term "an effective amount" means an amount of the compound or pharmaceutical composition that produces a statistically significant result. For example, with respect to the present invention, an effective amount of a compound or pharmaceutical composition means an amount that provides a statistically significant reduction in Wnt signaling; or the stabilization of or reversal of a disease or condition associated with Wnt signaling. An effective amount can be determined using known techniques, depending upon variables such as the particular disease or condition treated, the patient, the patient condition, the method of administration, the formulation, and other factors. An effective amount is demonstrated by a statistically significant difference in Wnt signaling between a treatment group and a control group.

The term "biological sample" means any fluid or other material derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term is a organ or tissue extract and a culture fluid in which any cells or tissue preparation from the subject has been incubated.

The term "cell" is used in its usual biological sense, and does not refer to an entire multicellular organism. The cell can, for example, be in vitro, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The phrase "detectable moiety" as used herein refers to a moiety that can be imaged and/or detected in vivo, ex vivo, or in vitro, by a procedure or modality described herein or known to one of skill in the art. As used herein, the detectable moiety can be directly or indirectly linked to the ligand used in the methods of the present invention.

The term "diagnostically labeled" means that the antibody has attached to it a diagnostically detectable label.

A protein that is "linked to a detectable moiety" is one that is bound, either covalently, through a linker, or through ionic, van der Waals or hydrogen bonds to a label such that the presence of the protein may be detected by detecting the presence of the label or detectable moiety bound to the protein.

The term "mammary tumor stem cells" means mammary tumor cells that are tumorigenic, i.e., that they can give rise to additional tumorigenic cells (self-renew) and non-tumorigenic tumor cells ("differentiation"). For example, a mammary tumor stem cell can form a new tumor when grafted to a mammary fat pad of a mouse (e.g., a nude mouse, a NOD immuno-deficient mouse, or a NOD/SCID immuno-deficient mouse). Mammary tumor stem cells can be analyzed using dilution xenograft assay.

The term "somatic mammary stem cells" means cells that can generate both the ductal and lobular structures of the mammary gland, can generate all the cell lineages of the mammary epithelium (e.g., luminal cells and myoepithelial cells), and can self-renew. For example, when transplanted to a mammary fat pad in a mouse or rat in vivo, a somatic mammary stem cell can generate functional ductal trees. Somatic mammary stem cells can also generate mammary progenitor cells. The progenitor cells have proliferative capability and are the immediate precursors to the differentiated mammary cells such as luminal cells and myoepithelial cells. Mammary progenitor cells can be detected by their ability to generate colonies in vitro.

As used herein, the terms "treatment" or "treating" means prophylaxis and therapy.

Thus, methods of treatment or treating of the present invention include treatments or treating to prevent or reduce Wnt signaling, or to stabilize or reverse conditions or diseases associated with Wnt activity.

The term "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. A "tumor" includes at least one tumor cell.

All references, patents, patent publications, articles, and databases, referred to in this application are incorporated-by-reference in their entirety, as if each were specifically and individually incorporated herein by reference.

It is disclosed here that Wnt signaling receptor LRP6 is highly expressed in a cell fraction that contains somatic mammary stem cell activity. The inventors established co-localization of mammary epithelial cells having high LRP6 expression with the somatic mammary stem cell-enriched fraction and determined the enhanced stem cell function of the LRP6 high fraction. In situ examination of LRP6 expression confirmed the heterogeneous expression of LRP6 and located the cells with high levels of LRP6 expression in the mammary ductal cell population. Similar to somatic mammary stem cells, it is expected that mammary tumor stem cells also express high levels of LRP6. Although the observations disclosed here were made with mice, it is expected that they also apply to other mammals such as humans and rats given that the Wnt pathway and the mammary gland development are highly conserved across the mammalian species.

In one aspect, the present invention relates to a method for enriching somatic mammary stem cells from a population of mammary cells. The method includes the steps of obtaining a population of mammary cells containing one or more somatic mammary stem cells, contacting said population of mammary cells with an anti-LRP6 antibody, and selecting cells that bind to the antibody. Preferably, at least 1%, 2%, 3%, 4%, 5%, 6%, or 7% of the selected cells are somatic mammary stem cells. As Shackleton M et al. (Nature 439:84-88,2006) estimated that mammary stem cells occur at a frequency of about 1 in 1,300 total mammary cells in mice, a 1% mammary stem cell concentration represents a 13-fold enrichment. While other methods of enriching for mammary stem cells that involve the use of cell surface markers are known, these methods require a combination of at least two cell surface markers (see e.g., "Stingl J et al. *Nature* 2006, 439:993-997" for the use of cell surface markers CD49f and CD24). The method provided here uses a single marker (LRP6) and can achieve a comparable enrichment level to the methods that involve the use of multiple markers.

It is well within the capability of a skilled artisan to isolate mammary cells from a mammary gland. One example is provided in Example 1 below (see also Stingl J et al. *Nature* 2006, 439:993-997, which is herein incorporated by reference in its entirety). Other methods are known in the art. Typically, known procedures provide a population of mammary cells that is essentially free of adipocyte contamination but includes mammary epithelial cells, stromal cells (e.g., fibroblasts and other connective tissue cells), endothelial cells, and hematopoietic cells. Methods of isolating mammary epithelial cells are also well known in the art (see e.g., Gould MN et al. Cancer Res 1986, 46:4942-4945, which is herein incorporated by reference in its entirety). Somatic mammary stem cells can then be enriched using the LRP6 marker for positive selection from the population of mammary cells. Optionally, a somatic mammary stem cell "negative marker" (i.e., a marker not present on the cell surface of somatic mammary stem cells) is used for negative selection (i.e., for the elimination of cells that are not somatic mammary stem cells). For example, endothelial cell markers CD31 and Von Willebrand factor, hematopoietic cell markers CD45 and Ter119, and stromal cell marker CD140a can be used to eliminate certain endothelial, hematopoietic, and stromal cells to facilitate the enrichment of somatic mammary stem cells. Depending on the particular enrichment techniques, the negative markers can be used to eliminate certain non-mammary stem cells before the positive selection with LRP6 or the positive and negative selections can be accomplished in one step. As an example for the former, antibodies to one or more of CD31, Von Willebrand factor, CD45, Ter119, and CD140a can be conjugated to a matrix such as magnetic beads to deplete the non-epithelial cells. The leftover epithelial enriched population of mammary cells is then labeled with fluorochrome-conjugated LRP6 antibodies for enriching somatic mammary stem cells by, for example, flow cytometry. As an example for the latter, antibodies to one or more of CD31, CD45, Ter119, and CD140a and antibodies to LRP6 can be conjugated to different fluorochrome so that endothelial, stromal, and/or hematopoietic cells can be gated out from LRP6 flow cytometry enrichment. Similarly, one or more mammary epithelial cell surface markers can optionally be used to enrich for mammary epithelial cells first before the LRP6 marker is used to enrich for somatic mammary stem cells.

Any agent that can bind to the cell surface markers can be used to practice the present invention. Antibodies specific for the markers are examples of such agents.

cDNA and amino acid sequences for LRP6 in various species are available and it is well within the capability of a skilled artisan to generate specific antibodies to these proteins if they are not already available. The human LRP6 cDNA and amino acid sequences are provided in the sequence listing at SEQ ID NO: 1 and 2, respectively. The mouse LRP6 cDNA and amino acid sequences are provided in the sequence listing at SEQ ID NO:3 and 4, respectively.

In some embodiments, flow cytometry could be employed to conduct the positive selection and, if applicable, the negative selection as well. A skilled artisan is familiar with flow cytometry-related techniques such as labeling targeted cells (e.g., somatic mammary stem cells) with cell surface marker antibodies (e.g., anti-LRP6 antibodies), setting suitable parameters for sorting and collecting labeled cells, and collecting the targeted cells (see e.g., Givan A, Flow Cytometry: First Principles, Wiley-Liss, New York, 1992; and Owens M A & Loken M R, Flow Cytometry: Principles for Clinical Laboratory Practice, Wiley-Liss, New York, 1995). For the purpose of the present invention, a population of LRP6 high mammary epithelial cells is taken for the enrichment of somatic mammary stem cells. By LRP6 high mammary epithelial cells, the inventors mean the top 10% of the total mammary epithelial cell population in terms of LRP6 expression level at the cellular surface. Therefore, examples of a population of LRP6 high mammary epithelial cells that could be taken for enriching for somatic mammary stem cells include the top 10%, 9%, 8%, 7%, 6%, 5%, 4% 3%, 2%, or 1% of the total mammary epithelial cell population in terms of LRP6 expression level at the cellular surface. Said enrichment for somatic mammary stem cells could be achieved by collecting the top 10% (in terms of LRP6 expression level at the cellular surface) or any fraction within the top 10% (e.g., top 9%, 8%, 7%, 6%, 5%, 4% 3%, 2%, or 1%) of a mammary cell population that includes the total mammary epithelial cell population (or a substantial portion thereof) and is essentially free of adipocyte contamination. In one form, the mammary cell population is depleted of certain endothelial cells, hematopoietic cells, and/or stroma cells using one or more of the following markers: CD31, Von Willebrand factor, CD45, Ter119, and CD140a. For example, the mammary cell population could be depleted of CD31+ cells. By a substantial portion of the total mammary epithelial cell population, the inventors mean at least 70%, 80%, 90%, or 95% of the total mammary epithelial cell population.

In some embodiments, a matrix such as magnetic beads to which an antibody (e.g., an anti-LRP6 antibody) could be conjugated directly or indirectly is employed to conduct the positive selection and, if applicable, the negative selection as well. In this regard, targeted cells could be separated from other cells by binding to the matrix through the antibody. When the matrix is used for positive selection in connection with an anti-LRP6 antibody, a skilled artisan could readily adjust and find suitable binding conditions so that LRP6 high mammary epithelial cells are bound to the matrix while other mammary epithelial cells (LRP6 negative and LRP5 low) are not.

In some other embodiments, flow cytometry is used to conduct the positive selection and a matrix described above is used to conduct the negative selection or vise versa.

Antibodies (e.g., anti-LRP6 antibodies) useful in the present invention could be labeled with a marker or they may be conjugated to a matrix. In some embodiments, the marker is used to conjugate the antibodies to the matrix. Examples of markers include biotin, which can be removed by avidin bound to a support, and fluorochromes (e.g. fluorescein), which provide for separation using fluorescence activated sorters. Examples of matrices include magnetic beads, which allow for direct magnetic separation (Kemshead J T, J Hematother 1992;1:35-44), panning surfaces such as plates, (Lebkowski J S et al., J. of Cellular Biochemistry supple. 1994, 18b:58), dense particles for density centrifugation (Van Vlasselaer P, Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, CA.), dense particles alone (Zwerner et al., Immunol. Meth. 1996, 198:199-202), adsorption columns (Berenson et al., Journal of Immunological Methods 1986, 91:11 - 19), and adsorption membranes.

The antibodies may be directly or indirectly coupled to a matrix. For example, the antibodies may be chemically bound to the surface of magnetic particles (e.g., using cyanogen bromide). When the magnetic particles are reacted with a sample, conjugates will form between the magnetic particles with bound antibodies and the cells having the corresponding markers on their surfaces. Alternatively, the antibodies may be indirectly conjugated to a matrix. For example, the antibodies may be biotinylated and indirectly conjugated to a matrix which is labeled with avidin. Magnetic iron-dextran particles that are covalently labeled with avidin (Miltenyi S et al., Cytometry 1990, 11:231) can be used in this regard. Many alternative indirect ways to specifically cross-link the antibodies and matrices would also be apparent to those skilled in the art.

As another example, a matrix may be coated with a second antibody having specificity for the antibodies against the cell surface markers. By way of example, if the antibodies against the cell surface markers are mouse IgG antibodies, the second antibody may be rabbit anti-mouse IgG.

As another example, bispecific antibodies and tetrameric antibody complexes can be used. Bispecific antibodies contain a variable region of an antibody specific for a cell surface marker and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (Proc Natl Acad Sci USA 1986, 83:1453) and Staerz & Bevan, (Immunology Today 1986, 7:241). Bispecific antibodies may also be constructed by chemical means using procedures such as those described by Staerz et al. (Nature 1985, 314:628) and Perez et al. (Nature 1985, 316:354), or by expression of recombinant immunoglobulin gene constructs.

A tetrameric immunological complex may be prepared by mixing a first monoclonal antibody which is capable of binding to an antigen on the surface of a matrix and a second monoclonal antibody specific for a cell surface marker. The first and second monoclonal antibodies are from a first animal species. The first and second antibody are reacted with an about equimolar amount of monoclonal antibodies of a second animal species which are directed against the Fc-fragments of the antibodies of the first animal species. The first and second antibodies may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles having a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. in J. Hematotherapy 1992, 1:35-44, at pages 36 to 39 and Ziolo et al. Science 1994, 257:219 which are incorporated herein by reference. Colloidal particles of dextran-iron complex are preferably used in the process of the invention (Molday, R. S. and McKenzie, L. L. FEBS Lett. 1984, 170:232; Miltenyi et al. Cytometry 1990, 11:231; Molday, R. S. and MacKenzie, D., J. Immunol. Methods 1982, 52:353; Thomas et al., J. Hematother. 1993, 2:297; and U.S. Pat. No. 4,452,733, which are each incorporated herein by reference).

In accordance with the magnetic separation method, a sample containing the cells to be recovered, is reacted with an antibody specific for a cellular surface marker of the cells so that the antibody binds to the cells present in the sample to form cell conjugates of the targeted cells and the antibody. The reaction conditions are selected to provide the desired level of binding of the targeted cells and the antibody. The concentration of the antibody is selected depending on the estimated concentration of the targeted cells in the sample. The magnetic particles are then added and the mixture is incubated for a suitable period of time at a suitable temperature. The sample is then ready to be separated in a magnetic device.

In another aspect, the present invention relates to a method of enriching mammary tumor stem cells from a population of mammary tumor cells. The method includes the steps of obtaining a population of mammary tumor cells containing one or more mammary tumor stem cells, contacting said population of mammary tumor cells with an anti-LRP6 antibody, and selecting cells that bind to the antibody. Preferably, at least 1%, 2%, 3%, 4%, 5%, 6%, or 7% of the selected cells are mammary tumor stem cells. Also preferably, the mammary tumor stem cells are enriched for at least 2-fold, 3-fold, 5-fold, 7-fold, or 10-fold relative to the original tumor from which said population is derived (unfractionated tumor cells). Reagents and procedures for enriching somatic mammary stem cells can be used similarly here for enriching mammary tumor stem cells.

In another aspect, the present invention relates to a method for screening for an agent that may modulate (either inhibit or enhance) LRP6 activity in a cell. The method includes the steps of providing a cell that has attenuated LRP5 activity (e.g., the LRP5 activity is reduced by at least 80%, 90%, or 95%), exposing the cell to a test agent, determining the LRP6 activity in the cell, and comparing the LRP6 activity to that of a control cell (the same type of cell as the exposed cell) not exposed to the test agent wherein a higher or lower LRP6 activity in the exposed cell than that of the control cell indicates that the agent can modulate LRP6 activity. If the cell does not express any Wnt ligand or produces an insufficient amount of Wnt for the purpose of conducting the screening assay, a Wnt ligand such as Wnt1 or Wnt3a may be added exogenously to stimulate Wnt signaling through LRP6. Alternatively, a DNA construct for expressing a Wnt ligand (e.g., a Wnt expression vector) can be introduced into the cell to express a Wnt protein.

A cell with attenuated LRP5 activity can be provided by using a LRP5-specific antibody to block its activity or by using antisense oligonucleotides, siRNA, or shRNA to block LRP5 gene expression so that the level of LRP5 protein in the cell is reduced by at least 80%, 90%, or 95% (see e.g., Young J J et al. PLoS Pathog 2007, 3:e27). Agents that can inhibit LRP6 activity specifically are useful for treating mammary tumor or breast cancer.

Optionally, a cell that has wild-type LRP5 activity can also be employed in the screening assay as a control to select for agents that specifically modulate LRP6-mediated signaling.

Those agents that can modulate Wnt signaling in LRP5 attenuated cells but not wild-type LRP5 control cells are identified as specific modulators of LRP6-mediated signaling.

In a preferred embodiment, a LRP5 null (knockout) cell is used in the screening. By a LRP5 null cell, the inventors mean that no detectable level of functional LRP5 is produced. Such a cell can be provided by, for example, introducing one or more mutations into the LRP5 nucleic acid gene sequence (including complete deletion of the gene sequence). In one form, the LRP5 gene is disrupted so that the cell does not express any part of the LRP5 coding sequence at the mRNA level. Preferably, both chromosomal copies of the LRP5 nucleic acid sequence are disrupted in the cell.

A LRP5 null animal such as a LRP5 null mouse or rat can be a source of LRP5 null cells.

Null or knockout animals such as knockout mice and rats are routinely generated in the art. A LRP5 knockout rat can be generated by a variety method such as that described in published U.S. patent application 20030150001, which is herein incorporated by reference in its entirety. The term null or knockout animals are used broadly to encompass a knockout fetus and as well as a knockout neonate and adult animal.

The LRP5 gene may be disrupted using a variety of technologies familiar to those skilled in the art. For example, a stop codon may be introduced into the gene by homologous recombination. Alternatively, a deletion may be introduced into the gene by homologous recombination. In some embodiments, stop codons may be introduced into all reading frames in the sequence downstream of the deletion to eliminate artifactual translation products. In further embodiments, the gene may be disrupted by inserting a gene encoding a marker protein, for example, via homologous recombination.

Examples of suitable cells that can be used in the screening method include mouse or rat embryonic fibroblasts (MEFs), primary keratinocyte cultures (e.g., mouse or rat primary keratinocyte cultures), and mouse or rat embryonic stem cells. A skilled artisan could readily isolate from Lrp5$^{-/-}$ murine animals murine embryonic fibroblasts from mid-gestational embryos, primary keratinocyte cultures from later stage embryos, or murine embryonic stem cells. For example, to establish murine embryonic fibroblast lines, one could isolate Lrp5$^{-/-}$ embryos (or control littermate embryos) at embryonic day 12 or 13, remove the head and internal organs, and then disassociate the remaining tissue with a razor blade in the presence of trypsin. These cells will be useful for up to 6-7 passages.

LRP6 activity can be measured by any part of the Wnt pathway at or downstream of LRP6. For example, the level of LRP6 at the mRNA or protein level can be measured. Phosphorylation of the C-terminus of LRP6 can also be measured. Alternatively, the activity of glycogen synthase kinase-3 (GSK3) activity can be measured. An increase in GSK3 activity indicates an inhibition of LRP6 activity and a decrease in GSK3 activity indicates an increase in LRP6 activity. β-catenin level such as that in the cytosol and/or nucleus can also be measured as a reflection of LRP6 activity. An increase in β-catenin level indicates an increase in LRP6 activity and vise versa. In one embodiment, the β-catenin level in the nucleus is measured wherein an increase in level indicates more LRP6 activity and vise versa. Alternatively, a Wnt reporter construct containing a reporter operably linked to a suitable promoter responsive to Wnt pathway activity can be provided in a cell for measuring LRP6 activity. Examples of suitable promoters include promoters for Wnt/β-catenin-responsive genes such as Axin2, CyclinD1, PPAR-delta, TCF, and LEF1 (see e.g., Yan D et al. Proc Natl Acad Sci USA 2001, 98:14973-8; Lustig B et al. Mol Cell Biol 2002, 22:1184-93; Jho E H et al. Mol Cell Biol 2002, 2:1172-83; Tetsu O et al. Nature 1999, 398:422-6; Shtutman M et al. Proc Natl Acad Sci USA 1999, 96:5522-7; He T C et al. Cell 1999, 99:335-45; Roose J et al. Science 1999, 285:1923-6; Hovanes K et al. Nat Genet 2001, 28:53-7; and Filali M et al. J Biol Chem 2002, 277:33398-410). A skilled artisan is familiar with these promoters. For example, a TCF-luciferase reporter gene assay (TOPFLASH) is commercially available (Mao et al. Nature 2001, 411:321-325).

Additional examples of Wnt/β-catenin-responsive genes include c-myc, c-jun, fra-1, uPAR, matrix metalloproteinase MMP-7, Nr-CAM, ITF-2, Gastrin, CD44, EphB/ephrin-B, BMP4, claudin-1, Survivin, VEGF, FGF18, Hath1, Met, endothelin-1, c-myc binding protein, L1 neural adhesion, Id2, Tiaml, Nitric Oxide, Synthase 2, Dickkopf, FGF9, FGF20, Sox9, Runx2, SALL4, RANK ligand, CCN1/Cyr61, Sox2, Pituitary tumor transforming gene (PTTG), Delta-like 1, FoxN1, matrix metalloproteinase-26, nanog, Frizzled 7, Follistatin, Siamois, fibronectin, myogenic bHLH, engrailed-2, Xnr3, connexin43, twin, connexin 30, retinoic acid receptor gamma, dharma/bozozok, MITF/nacre, Wrch-1, TNF family 41BB ligand, ephrinBl, Stra6, autotoxin, ISLR, Twist, Stromelysin, WISP, Brachyury, Proglucagon, Osteocalcin, cyclooxygenase-2, Irx3, Six3, neurogenin 1, WISP-1, WISP-2, IGF-II, Proliferin-2, Proliferin-3, Emp, IGF-1, VEGF-C, MDR1, IL-6, periostin, Cdx1, Cdx4, betaTrCP, sFRP-2, Pitx2, EGF receptor, Eda (TNF-related), E-cadherin, Keratin, movol, Jaggedl, mBTEB2, FGF4, Interleukin8, ret, connexin43, versican, Ubx, wingless, Dpp, Engrailed, Dfrizzled2, shavenbaby, stripe, and Nemo.

A reporter gene is defined broadly here to refer to a DNA sequence whose expression in a cell can be measured. Preferably, the reporter gene produces a polypeptide product whose function can be measured. Examples of such reporter genes include but are not limited to a β-galactosidase gene, a luciferase gene, and a green fluorescent protein (GFP) gene. An increase in the expression (at the mRNA or protein level) or activity of the reporter gene indicates an increase in LRP6 activity and vise versa. As another example, the reporter gene can be an inhibitor of the expression of a killer gene (the product of which lead to the death of the host cell) from another expression construct introduced into the cell. This is especially useful for screening for agents that can inhibit the activity of LRP6. For example, when an agent sufficiently inhibits the activity of LRP6, the expression of reporter gene will be sufficiently inhibited resulting in the expression of the killer gene and in turn the death of the cell. In this regard, cell death is the end point of the screening.

In another aspect, the present invention relates to a method for inhibiting the proliferation or causing the death of a mammary tumor cell that expresses LRP6. The method includes the step of contacting the mammary tumor cell with an agent that inhibits LRP6 activity in an amount sufficient to inhibit the proliferation or causing the death of the mammary tumor cell. Preferably, the mammary tumor cell expresses a high level of LRP6. For example, the mammary tumor cell can be a mammary tumor stem cell. Since mammary tumor stem cells are expected to co-localize with the fraction of high level LRP6 mammary tumor cells, mammary tumor stem cells can be treated by contacting a population of mammary tumor cells that express a high level of LRP6.

In one embodiment, the above method is used to treat a mammary tumor in a mammal (e.g., a human, mouse, or rat) in vivo by administering an agent that inhibits LRP6 activity into the mammal in an amount sufficient to inhibit the proliferation or causing the death of mammary tumor cells such as mammary tumor stem cells. As mammary tumor stem cells express a high level of LRP6, the method is especially useful to inhibit the growth or causing the death of mammary tumor stem cells. Optionally, another mammary tumor/breast cancer therapeutic agent such as a chemotherapeutic agent or radiation is administered in connection with the agent that inhibits LRP6 activity. This other mammary tumor/breast cancer therapeutic agent in some cases may eradicate the non-stem cell population in the mammary tumor.

One example of agents that inhibit LRP6 activity is an anti-LRP6 antibody (e.g., specific for LRP6). As LRP6 is a cellular surface receptor with an extracellular domain, an anti-LRP6 antibody directed to an epitope in the extracellular domain can readily inhibit the activity of LRP6.

In some instances, the antibody belongs to a sub-type that activates serum complement when complexed with the transmembrane protein thereby mediating cytotoxicity or antigen-dependent cytotoxicity (ADCC).

The LRP6 antibody can also be conjugated to a mammary tumor/breast cancer therapeutic agent (e.g., a chemotherapeutic agent) to deliver the therapeutic agent to the targeted tumor cells. In this case, the LRP6 antibody serves as a delivering vehicle. The therapeutic agent can be conjugated to the antibody either covalently, through a linker or a chemical bond, or noncovalently, through ionic, van der Waals, electrostatic, or hydrogen bonds. The therapeutic agent is typically a cytotoxic agent that can cause the death of the target cell.

Another example of the agents that inhibit LRP6 activity is a nucleic acid molecule that inhibits LRP6 gene expression. Examples of such nucleic acid molecules include antisense oligonucleotides, RNA interference (RNAi) molecules such as siRNA (small interfering RNA) molecules, and shRNA (short hairpin RNA) molecules. Given the cDNA sequences of LRP6 for various species are known in the art, it is well within the capability of a skilled artisan to develop such nucleic acid molecules. Both non-viral and viral vector delivery systems can be used to deliver the nucleic acid molecules. For a review of gene therapy procedures, see Anderson, Science 1992, 256:808-813; Nabel & Felgner, TIBTECH 1993, 11:211-217; Mitani & Caskey, TIBTECH 1993, 11:162-166; Dillon, TIBTECH 1993, 11:167-175; Miller, Nature 1992, 357:455-460; Van Brunt, Biotechnology 1988, 6:1149-1154; Vigne, Restorative Neurology and Neuroscience 1995, 8:35-36; Kremer & Perricaudet, British Medical Bulletin 1995, 51:31-44; Haddada et al., in Current Topics in Microbiology and Immunology Doerfler and Bohm (eds) (1995); and Yu et al., Gene Therapy 1994, 1:13-26.

In some embodiments, small interfering RNAs are administered. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, Nature 2001, 411:428-29; Elbahir et al., Nature 2001, 411:494-98; and Fire et al., Nature 1998, 391:806-11, where methods of making interfering RNA also are discussed. The siRNA inhibitors are less than 100 base pairs, typically 30 bps or shorter, and are made by approaches known in the art. Exemplary siRNAs according to the invention can have up to 29 bps, 25 bps, 22 bps, 21 bps, 20 bps, 15 bps, 10 bps, 5 bps or any integer thereabout or therebetween.

Methods of non-viral delivery of nucleic acid molecules include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Delivery can be to cells (ex vivo administration) or target tissues (in vivo administration). The preparation of lipid: nucleic acid complexes, including targeted liposomes such as immunolipid complexes, is well known to one of ordinary skill in the art (see e.g., Crystal, Science 1995, 270:404-410; Blaese et al., Cancer Gene Ther. 1995, 2:291-297; Behr et al., Bioconjugate Chem. 1994, 5:382-389; Remy et al., Bioconjugate Chem. 1994, 5:647-654; Gao et al., Gene Therapy 1995, 2:710-722; Ahmad et al., Cancer Res. 1992, 52:4817-4820; and U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of the nucleic acid molecules are known in the art. Conventional viral based systems for the delivery of such nucleic acid molecules include retroviral, lentivirus, adenoviral, adeno-associated and herpes simplex virus vectors for gene transfer.

It may be desirable that the gene therapy vector be delivered with a high degree of specificity to a particular tissue type such as mammary tumor. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., Proc Natl Acad Sci USA 1995, 92:9747-9751, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient (include humans and other mammals such as mice and rats), typically by systemic administration (e.g., intravenous, intraperitoneal, intramuscular, subdermal, or intracranial infusion) or topical application, as described below.

Vectors (e.g., retroviruses, adenoviruses, liposomes, etc.) containing therapeutic nucleic acids can also be administered directly to the patient for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., Remington's Pharmaceutical Sciences, 17th ed., 1989).

The agents that inhibit LRP6 activity can be administered by a variety of methods including, but not limited to parenteral (e.g., intravenous, intramuscular, intradermal, intraperitoneal, and subcutaneous routes), topical, oral, local, or transdermal administration. These methods can be used for prophylactic and/or therapeutic treatment.

The compositions for administration will commonly comprise an agent that inhibits LRP6 activity dissolved in a pharmaceutically acceptable carrier, preferably an aqueous carrier. A variety of aqueous carriers can be used, e.g., buffered saline and the like. These solutions are preferably sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions containing agents that inhibit LRP6 activity (e.g., antibodies) can be administered for therapeutic or prophylactic treatments. In therapeutic applications, compositions are administered to a patient suffering from breast cancer/mammary tumor in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents to effectively treat the patient. An amount of an agent that is capable of preventing or slowing the development of breast cancer in a patient is referred to as a "prophylactically effective dose." The particular dose required for a prophylactic treatment will depend upon the medical condition and history of the patient as well as other factors such as age, weight, gender, administration route, efficiency, etc. Such prophylactic treatments may be used, e.g., in a patient who has previously had breast cancer/mammary tumor to prevent a recurrence of the cancer/tumor, or in a patient who is suspected of having a significant likelihood of developing breast cancer/mammary tumor.

In another aspect, the present invention relates to a method for detecting or imaging mammary or mammary tumor cells that express a high level of LRP6 such as somatic mammary stem cells and mammary tumor stem cells. The method includes the steps of administering an LRP6 antibody based contrast agent and obtaining an image of the labeled mammary or mammary tumor cells. This method is useful for monitoring the effectiveness of breast cancer treatment by determining whether the mammary tumor stem cells have been inhibited or eradicated. Any suitable medical imaging techniques can be used in this regard. Examples of such techniques include ultrasound, computerized tomography (CT), magnetic resonance imaging (MRI), and nuclear medicine techniques such as gamma ray detection by a gamma ray detector (e.g., a gamma scintillation camera or a 3-dimensional imaging camera), positron emission tomography (PET) and single photon emission computed tomography (SPECT). A skilled artisan can readily make the suitable contrast agents using the LRP6 antibody, for example, by attaching a detectable label for a particular imaging technique to a LRP6 antibody (e.g., covalently through a linker or a chemical bond). For example, for MRI detection, a superparamagnetic iron oxide nanoparticle (SPION) can be conjugated to an LRP6 antibody for administering and MRI detection. For nuclear medicine detection, radionuclide-labeled LRP6 antibody can be administered and radiation emission from the nucleotide can be measured and an image thereof can be obtained.

In another aspect, the present invention relates to the detection of mammary basal-like cells. In this method an agent is used to detect Lrp6 expression in a tissue or biological sample suspected of including mammary basal-like cells. Any agent that can bind to LRP6 can be used to practice the invention. Antibodies specific to LRP6 are examples of such agents. The antibody is detected in the tissue or sample by linking a detectable moiety to the antibody, contacting the antibody with the tissue or sample, and detecting the presence of the detectable moiety in the tissue or sample.

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss,-Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)).

Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be detectably labeled and used, for example, to detect LRP6 on the surface or in the interior of a mammary basal-like cell. The fate of the antibody during and after binding can be followed in vitro or in vivo by using the appropriate method to detect the label. The labeled antibody may be utilized in vivo for diagnosis.

There are many different labels and methods of labeling known to those of ordinary skill in the art. Examples of the types of labels which can be used in the present invention include radioactive isotopes paramagnetic isotopes, and compounds which can be imaged by positron emission tomography (PET). Those of ordinary skill in the art will know of other suitable labels for binding to the antibodies used in the invention, or will be able to ascertain such, by routine experimentation. Diagnostically-labeled (e.g., radiolabeled) antibodies are effective.

Suitable detectable labels for diagnosis and imaging include radioactive, fluorescent, fluorogenic, chromogenic, or other chemical labels. Useful radiolabels, which are detected simply by gamma counter, scintillation counter, PET scanning or autoradiography include $^{3}H$, $^{124}I$, $^{125}I$, $^{131}I$, $^{35}S$ and $^{14}C$. In addition, $^{131}I$ is a useful therapeutic isotope (see below).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, Handbook of Fluorescent Probes and Research Chemicals, Sixth Ed., Molecular Probes, Eugene, Oreg. 1996). Fluorescein, fluorescein derivatives and fluorescein-like molecules such as Oregon Green.™. and its derivatives, Rhodamine Green.™. and Rhodol Green.™., are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green.™. derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red.™. derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., Science 281:2013-2016 (1998), and quantum dots, e.g., zinc-sulfide-capped cadmium selenide (Chan, W. C. W. et al., Science 281:2016-2018 (1998)).

In yet another approach, the amino groups of a anti-LRP6 antibody are allowed to react with a reagent that yields a fluorescent product, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The antibodies can also be labeled for detection using fluorescence-emitting metals such as $^{152}Eu+$, or others of the lanthanide series. These metals can be attached to the peptide using such metal chelating groups as diethylenetriaminepentaacetic acid (DTPA) or ethylenediamine-tetraacetic acid (EDTA). DTPA in anhydride form can readily modify the $NH_2$-containing antibodies.

For in vivo diagnosis, radionuclides may be bound to the antibody either directly or indirectly using a chelating agent such as DTPA and EDTA. Examples of such radionuclides are $^{99}Tc$, $^{123}I$, $^{125}I$, $^{131}I$, $^{111}In$, $^{97}Ru$, $^{67}Cu$, $^{67}Ga$, $^{68}Ga$, $^{72}As$, $^{89}Zr$, $^{90}Y$ and $^{201}Tl$. Generally, the amount of labeled antibody needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

The antibodies can also be made detectable by coupling them to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, calorimetric detection is used, based on chromogenic compounds which have, or result in, chromophores with high extinction coefficients.

In situ detection of the labeled antibody may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay, which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140-200 keV range, which may be readily detected by conventional gamma cameras.

A preferred diagnostic method is radioimmunoscintigraphic analysis, which is preferably performed in a manner that results in serial total body gamma camera images and allows determination of regional activity by quantitative "region-of-interest" (ROI) analysis.

The diagnostically labeled antibodies may be incorporated into convenient dosage forms.

Preferably, for diagnosis, the labeled antibodies are administered systemically, e.g., by injection or infusion. When used, injection or infusion may be by any known route, preferably intravenous injection or infusion, subcutaneous injection, intramuscular, intracranial or intrathecal injection or infusion, or intraperitoneal administration. Injectables can be prepared in conventional forms, either as solutions or suspensions, solid forms.

A preferred way to label the antibody or fragment is by linking it to an enzyme and using it in an enzyme immunoassay (EIA), or enzyme-linked immunosorbent assay (ELISA). Such assays are described in greater detail in: Butler, J. E., The Behavior of Antigens and Antibodies Immobilized on a Solid Phase (Chapter 11) In: STRUCTURE OF ANTIGENS, Vol. 1 (Van Regenmortel, M., CRC Press, Boca Raton 1992, pp. 209-259; Butler, J. E., ELISA (Chapter 29), In: van Oss, C. J. et al., (eds), IMMUNOCHEMISTRY, Marcel Dekker, Inc., New York, 1994, pp. 759-803 Butler, J. E. (ed.), IMMUNOCHEMISTRY OF SOLID-PHASE IMMUNOASSAY, CRC Press, Boca Raton, 1991; Voller, A. et al., Bull. WHO 53:55-65 (1976); Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980 Ishikawa, E. et al. (eds.) Enzyme Immunoassay, Kagaku Shoin, Tokyo, 1981.

This enzyme, in turn, when later exposed to its substrate, will react with the substrate in such a manner as to produce a chemical moiety which can be detected, for example, by spectrophotometric, fluorometric or by visual means. Enzymes which are commonly used for this purpose include horseradish peroxidase, alkaline phosphatase, glucose-6-phosphate dehydrogenase, malate dehydrogenase, staphylococcal nuclease, .DELTA.-V-steroid isomerase, yeast alcohol dehydrogenase, .alpha.-glycerophosphate dehydrogenase, triose phosphate isomerase, asparaginase, glucose oxidase, .beta.-galactosidase, ribonuclease, urease, catalase, glucoamylase and acetylcholinesterase.

Radioimmunoscintigraphy is an important and attractive modality for experimental and clinical molecular imaging of cancer. One can raise, characterize, and propagate antibodies reactive against virtually any given protein antigen, even those present as minor components of complex protein mixtures or as minor surface components of whole cells. Established methods for radiolabeling antibodies in suitable quantity and of appropriate quantity for scintigraphy are available, feasible, relatively inexpensive, and adaptable to virtually any antibody regardless of its epitopic specificity. New radiolabeling methods are continually emerging, and many laboratories are evaluating a wide range of antibody derivatives—from full-length chimeric and humanized molecules, to monomeric and multimeric antibody fragments, to immuno-conjugates—as potentially superior imaging and therapeutic agents, with improved targeting selectivity and more favorable biological turnover kinetics (Program and Abstracts, Ninth Conference on Cancer Therapy with Antibodies and Immunoconjugates. 2002. Cancer Biotherapy & Radiopharmaceuticals 17:465-494).

Moreover, the reagents, supplies, and equipment required to perform radioimmunoscintigraphy in experimental animals and in humans are commonplace. For decades decommissioned or refurbished clinical gamma cameras have proven satisfactory for animal imaging applications, and they continue to do so. Modified or custom-built gamma cameras adapted for small animal imaging are becoming more widely available.

The major advantage of scintigraphy as a molecular imaging modality (not limited to imaging with antibodies) is that the acquired images are inherently quantitative. The physics of gamma radiation and the mathematical analysis of nuclear images, including corrections for photon attenuation and other artifacts, are well understood. In animal models as well as in human studies one can noninvasively and accurately measure net accumulation and some kinetic parameters of radiopharmaceutical interactions with target lesions, and the concurrent collection of even a small set of biological samples (e.g., blood and excreta) for direct counting combined with quantitative analysis of diagnostic images enables useful dosimetry estimates for therapeutic purposes.

Many different radiopharmaceuticals are available for imaging neoplasms. They range from classical agents such as sodium iodide (Na-.sup.131I, thallium chloride (.sup.201TlCl), and gallium citrate (.sup.67Ga-citrate) to highly selective positron-emitting reporter gene detection systems (Vallabhajosula S (2001), In: Nuclear Oncology. I Khalkhali et al., eds. Lippincott Williams & Wilkins, Philadelphia, Pa. pp. 31-62; Iyer M et al. (2001) J Nucl Med 42, 96-105). Radiolabeled molecules that bind to specific cell surface components provide one successful approach to tumor imaging and therapy. Examples are OctreoScan.®. for imaging and potentially treating neuroendocrine neoplasms, CEAScan.®. and OncoScint.®. for imaging colorectal and ovarian cancers, and Bexxar.®. and Zevalin.®. for detecting and treating certain lymphomas.

In another aspect, the present invention relates to a method of diagnosing basal-like breast cancer. The method utilizes an agent to detect Lrp6 expression in a tissue, organ, or biological sample of a patient suspected of having basal-like cell breast cancer, and that agent is linked to a detectable moiety. The presence of the detectable moiety is detected and the Lrp6 expression level in the tissue, organ, or sample is determined and compared to a suitable control.

Although Example 1 below showed that Lrp6 is useful as a basal-like cell breast cancer diagnostic marker at the mRNA level, it is expected that LRP6 protein level can be used the same way. Therefore, Lrp6 expression level can be measured either at the mRNA level or at the protein level to practice the method of the present invention. Based on the data presented in Example 1 below, a skilled artisan can readily set up suitable controls as reference points of comparison for the expression of Lrp6. One suitable control is the median or average expression level of many breast cancer patients that do not have basal-like cell breast cancer. Another suitable control is the median or average expression level of many patients without breast cancer. In one particular embodiment, both of the above controls are used. The larger the number of patients used to establish a median or average level of Lrp6 expression as a control, the more accurate the diagnostic determination. Preferably, at least 25, 50, or 100 patients are used to establish the control level of expression.

An example of a pharmaceutical composition or compound of the present invention is an RNAi for LRP6. Preferably, the RNAi would include an internal promoter driving the expression of the RNAi only in cancer stem cells or progenitor cells. More preferably, a short hairpin-based (shRNA) approach to RNAi could be used to antagonize, or inactivate the transcript for LRP6. siRNA has been directed against LRP6 in an effort to confirm the existence of an autocrine Wnt signaling loop [Bafico, A., Liu, G., Goldin, L., Harris, V., Aaronson, S. A., Cancer Cell. November 2004; 6:497-506].

Another example of a pharmaceutical composition or a compound of the present invention is an antibody specific to LRP6. In this composition, an antibody specific to LRP6 is an antagonist that competitively inhibits binding of the Wnt ligand to the LRP6 and thereby inhibits activation of the Wnt signaling pathway. Known examples of antagonistic antibodies against other receptors include Erbitux and Herceptin. Applications of antibodies as a composition or a therapeutic are generally known, see for example U.S. Patent Publication Nos. 2006/0093607 and 2005/0003465. Moreover, a therapeutic agent (drug, chemotoxin, radiotherapeutic, small molecule) can be conjugated to such an antibody, ensuring delivery of the therapeutic agent to a specific target. (U.S. Pat. No. 6,989,144.) Moreover, internalizing antibodies can be conjugated to such a therapeutic agent, ensuring delivery of the therapeutic agent into the cytoplasm of a target cell. Antibodies conjugated to a therapeutic toxin for delivery to a target receptor site can be selected from monoclonal antibodies (humanized, fully human, or other), Fabs, or scFvs. Antibodies conjugated to a therapeutic agent which is internalized into a cell may also be monoclonal antibodies, but are more generally Fabs or scFvs. Further, such an antibody can be conjugated to a detectable reporting agent to indicate delivery of the antibody to a target site for imaging studies.

Methods for administering a pharmaceutical composition or compound to the patient are known in the art. For example, shRNA can be delivered to a mammalian cell by a vector, such as an adenovirus or retrovirus, in a target-specific manner. [Mize-Omata, S., Yuichi, O., Shigeru, I., Mize, N., Doi, T. S., Biochem Biophys Res Commun. Mar. 25, 2005; 328(4):1034-42; see also Edwin, F., Singh, R., Endersby, R.,Baker, S., Patel, T., J. Biol. Chem., Vol. 281, Issue 8, 4816-4822, Feb. 24, 2006; Lee, S., Choi, E., Jin, C., Kim, D., Gynecol Oncol. April 2005; 97(1):26-34; Zhang, C., Comai, L., Johnson, D., Molecular and Cellular Biology, Sug. 2005, 6899-6911]. According to the present invention, the target for the shRNA is the transcript for LRP6.

Retroviral vectors used to express shRNA could be put under the control of an RNA polymerase III (pol III) promoter, such as U6 or H1 for the purpose of inhibiting gene expression in a sequence specific manner. Several replication-competent retroviral vectors have been developed for this general purpose [Bromberg-White, J. L., Webb, C. P., Patacsil, V. S., Miranti, C. K., Williams, B. O., and Holman, S. L., 2004 Journal of Virology, May:4914-4916].

Having now generally described the invention, the same will be more readily understood through reference to the following examples, which are provided by way of illustration, and are not intended to be limiting of the present invention, unless specified.

EXAMPLES

Example 1

The Wnt Signaling Receptor LRP6 is Required for Mammary Stem Cell Activity and Wnt1-Induced Tumorigenesis Signaling by the Wnt family of secreted lipoproteins plays a central role in development and disease (1). At the cellular level, Wnt proteins regulate a broad range of functions including the self-renewal and differentiation of stem cells (2). Activation of the canonical Wnt cascade is initiated by the binding of Wnt proteins to cell surface receptors composed of a member of the Frizzled (Fzd) protein family and one of the low-density lipoprotein receptor-related proteins LRP5 or LRP6 (3, 4). Signaling from Wnt receptors increases cytoplasmic levels of β-catenin, which binds to transcription factors such as those of the LEF-1/TCF family and modulates the transcription of specific target genes. While Wnt-Frizzled interactions may also be involved in non-canonical Wnt signaling events, the LRP5/6 moiety appears to be specifically required for the canonical pathway (5).

Studies in mice suggest that canonical Wnt signaling plays a significant role during normal mammary gland development (6-11), which begins at about embryonic day 10.5 with the formation of two "mammary lines" (12). In response to signals from the underlying mesenchyme, the mammary lines give rise to five pairs of lens-shaped mammary placodes that grow and invaginate downwards into dermis to colonize the rudimentary fat pad. Activation of the canonical Wnt signaling pathway along the mammary lines coincides with the initiation of mammary morphogenesis and subsequently localizes to mammary placodes and buds (13, 14). Several Wnt ligands and receptor genes, including Lrp6, are expressed during embryonic mammary morphogenesis (13). Embryos expressing the canonical Wnt inhibitor Dkk1 display a complete block in the formation of mammary placodes and mice deficient for Lef-1 fail to maintain their mammary buds (6, 7), showing that Wnt signals are necessary for embryonic mammary development.

By birth, the mammary gland is composed of a few rudimentary ducts—containing an outer layer of myoepithelial and an inner layer of luminal epithelial cells—surrounded by the fat pad. During pre-pubertal and pubertal development, the ductal epithelium proliferates, until the fat pad is fully colonized with a sparse ductal tree. Lobuloalveolar precursor cells respond to endocrine signals during pregnancy, to colonize all the inter-ductal spaces, increasing cell number at least 10-fold (15). The expansion of mammary epithelium during juvenile growth, estrous and pregnancy, together with the remarkable regenerative capacity apparent during successive reproductive cycles, imply the existence of a mammary stem cell. In fact a subset of mammary cells that are enriched for stem cells have recently been isolated by fluorescence-activated cell sorting (FACS) of freshly isolated mammary cells. These cells express CD24 and CD49f but not CD31 (endothelial cell marker) and not CD45/TER119 (hematopoietic cell markers) (Stingl et al, Nature. Feb. 23, 2006;439(7079): 993-7). They are defined as $CD31^-CD45^-CD119^-/CD24^+/CD49f^{high}$, and are comprised of approximately 8% of all $CD31^-CD45^-CD119^-$ mammary cells. While not every cell in this subset of cells is a true stem cell, transplantation experiments have established a single cell in this population can sometimes regenerate a whole ductal tree.

A connection between mammary stem/progenitor cells and Wnt1- or β-catenin-induced tumorigenesis has recently been established. Transgenic expression of these genes results in widespread mammary hyperplasia and rapid tumor formation (11, 18). The hyperplastic tissue contains an increased fraction of mammary stem/progenitor cells which are thought to directly give rise to transformed cells (17, 19, 20). Tumors arising from stem/progenitor cells often show mixed lineage differentiation (21) and tumors induced by Wnt effectors indeed contain cells from both epithelial lineages (19, 20). Shown here is that the LRP6 receptor is expressed in the mammary stem cell fraction by FACS. Furthermore, LRP6 is required both during normal development and for Wnt1-induced tumorigenesis. In MMTV-Wnt1 transgenic mice loss of one copy of Lrp6 markedly reduces both the early proliferation of the progenitor cell population and the subsequent formation of mammary tumors. Furthermore, mammary placode and ductal tree development is inhibited in $Lrp6^{-/-}$ embryos. Taken together, these results suggest that canonical signaling through the LRP6 receptor is critical for mammary stem cell activity.

Material and Methods.

Mice.

$Lrp6^{+/-}$ mice were obtained from Dr. Skarnes. These mice had been back-crossed to C57B1/6J (B6) mice for six generations to create congenic Lrp6 mouse on a B6 background (to minimize genetic variation). MMTV-Wnt1 transgenic mice (maintained on a FVB/N background) and BAT-gal transgenic mice (maintained on a B6D2F1 background) were crossed with $Lrp6^{+/-}$ mice. PCR-based strategies were then used to genotype these mice (details available upon request). All experiments performed were in compliance with the guiding principles of the Guide for the Care and Use of Laboratory Animals, National Academics Press, 1996 and were approved in advance by the Van Andel Research Institute Institutional Animal Care and Use Committee. To assay the appearance of mammary tumors, the mice were inspected weekly and were euthanized when tumors appeared.

Immunohistochemistry for LRP6.

Mammary tissues were fixed for 2 hours in 4% paraformaldehyde at 4° C. and then embedded in paraffin and sectioned (5 µm). Immunohistochemistry was performed by using Vector ABC and DAB kits according to the manufacturer's recommendations (Vector Laboratories). Rabbit polyclonal antibody against Lrp6 was used at a 1:250 dilution. The antibody was purchased from Zymed Laboratories, CA.

Mammary Whole Mounts.

Inguinal mammary glands were dissected, fixed overnight in Carnoy formula (6:3:1 ratio of ethanol:chloroform:glacial acetic acid), rehydrated and stained overnight in Carmine alum stain. The stained glands were dehydrated, cleared in Xylene and stored in Methyl Green. After whole mount pictures had been taken, the tissues were embedded in paraffin for sectioning. Sections (5 µm) were rehydrated and counterstained with H&E.

Analysis of BAT-Gal Expression

For the analysis of BAT-gal expression whole mount embryos were fixed (0.2% glutaraldehyde, 1.5% formaldehyde, 5 mM EGTA, 2 mM $MgCl_2$ in PBS), washed (2 mM $MgCl_2$, 0.01% sodium deoxycholate, 0.02% NP-40 in PBS) and stained with X-Gal (1 mg/ml X-gal, 2 mM $MgCl_2$, 0.01% sodium deoxycholate, 0.02% NP-40, 5 mM $Fe_3(CN)_6$, 5 mM $Fe_4(CN)_6$ in PBS) at 30° C. for 30 minutes, dehydrated and cleared in Xylene. After whole mount pictures had been taken, the embryos were embedded in paraffin for sectioning. Sections (5 µm) were rehydrated and counterstained with eosin. Embryonic stage was confirmed by analysis of limb morphology.

Analysis of β-Galactosidase Expression.

Lrp6+/− and Lrp6+/+ (negative control) mammary glands were isolated and fixed in 2% paraformaldehyde plus 0.25% glutaraldehyde in PBS at 4° C. for 2 h. Glands were rinsed in 2 mM $MgCl_2$, 0.1% sodium deoxycholate, and 0.2% NP40 in PBS at room temperature for 2×1 h and stained overnight at 30° C. in X-gal buffer (1 mg/ml X-gal, 5 mM K-ferricyanide, 5 mM K-ferro in rinse buffer). Glands were rinsed in PBS, dehydrated and cleared in BABB (2:1 ratio of benzyl alcohol: bezyl benzoate), and briefly stored in Xylene. After whole mount pictures had been taken, the tissues were embedded in paraffin for sectioning. Sections (5 µm) were counterstained with 0.1% Nuclear Fast Red.

Isolation of Mammary Ductal Cells.

Mammary glands were obtained from $Lrp6^{+/-}$ and $Lrp6^{+/+}$ 12 week old, virgin Balb/c mice. The glands were harvested and minced with fine scissors on ice. Mammary organoids were dissociated by enzymatic digestion with hyaluronidase and collagenase for seven hours at 37° C. (reagents and protocol from Stem Cell Technologies, Vancouver, Canada). The mammary organoids were then further dissociated into single cells by brief trypsin and dispase exposures (reagents and protocol from Stem Cell Technologies). Single mammary epithelial cell preparations were then stained with CD45, Ter119, or CD31 antibodies. Single cells that did not express these markers were then stained with CD24 and CD49f and exposed to 10 µm 9H-(1,3-dichloro-9,9-dimethylacridin-2-one-7-yl) β-D-galactopyranoside (DDAOG) in Hanks buffer for 30 minute. All reagents and protocols for this experiment except DDAOG were from Stem Cell Technologies. DDAOG was purchased from Invitrogen.

Results

LRP6 is Expressed in the Mammary Gland.

Figure 2:
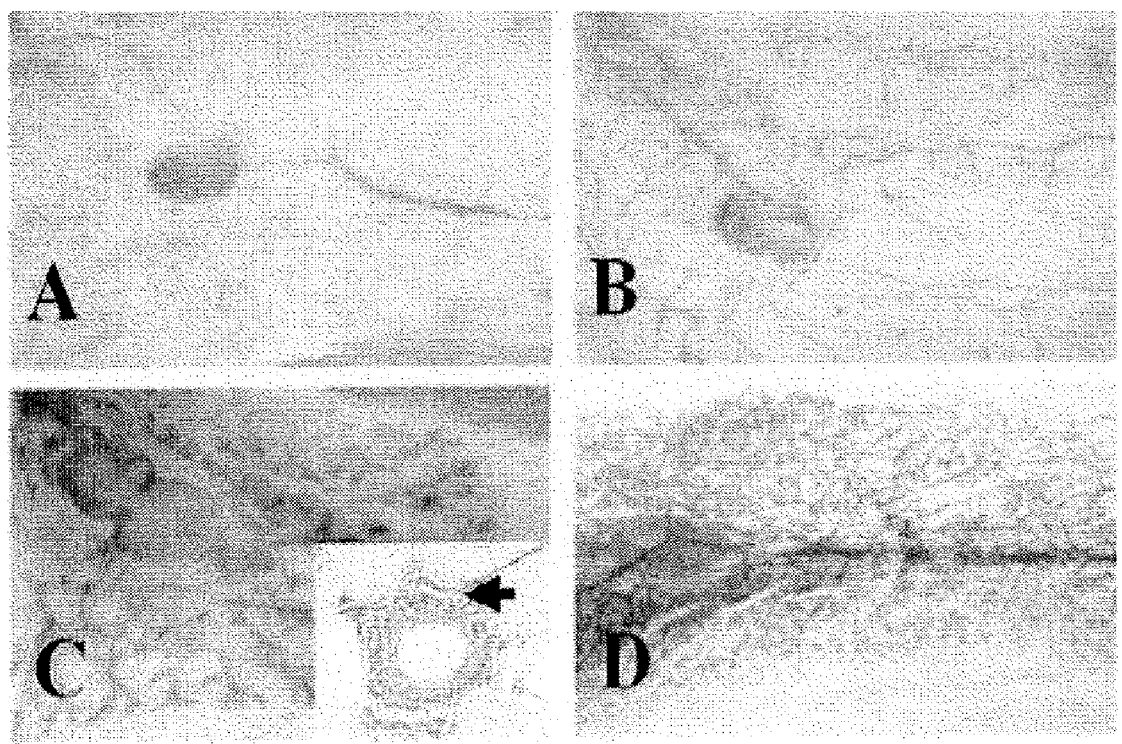
FIGS. 2A-D: LRP6 is expressed in the mammary. Mammary glands were isolated and stained for β-gal and β-gal is used as a marker for LRP6 expression.

LRP6-deficient mice were exploited to assess LRP6 expression. These mice were originally created in a large-scale mutagenesis screen designed to inactivate proteins containing signal peptides [Soriano, P., Nat Genet, 1999. 21(1): 70-1]. As part of this work, a targeting vector was used allowing for expression of the β-galactosidase (β-gal) gene from the promoter of the gene that was disrupted. Thus, the inventors used β-gal activity as a surrogate marker for LRP6 expression and found that LRP6 is expressed in the normal adult virgin mammary and during pregnancy (FIG. 2). β-gal reactive cells were present in the myoepithelial cell layer.

Lrp6 is Specifically Expressed in the Mammary Stem Cell Population.

Figure 4A:
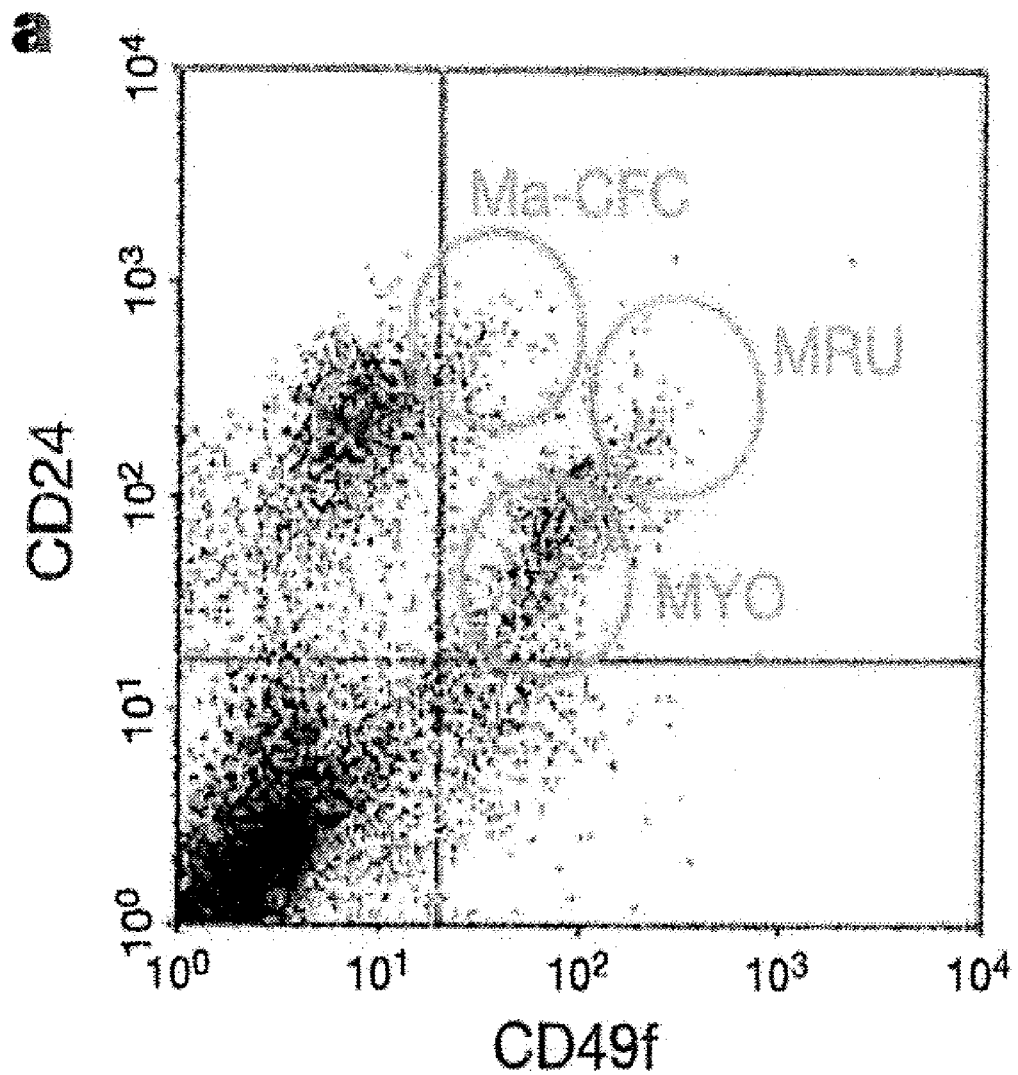
FIGS. 4A-C: Lrp6 is expressed in the MRU fraction (stem cell fraction). Shown in FIG. 4A is a FACS sort, 10,000 events, for mammary stem cells adapted from Stingl et al, Nature. Feb. 23, 2006;439(7079):993-7. The stem cells are located in the MRU fraction (right-hand-most circle).

A cell population enriched for mammary stem cells can be identified by FACS. These cells often referred to as MRUs (mammary repopulating units) express medium levels of CD24 and high levels of CD49f but do not express CD45, Ter119, or CD31. The method for isolating MRUs was first described by Stingl et al. (Nature. February 23, 2006;439 (7079):993-7). By performing single cell transplantations they found that the MRU cell population has a mammary stem cell frequency of 1/90 cells, compared to 1/1400 in unsorted mammary cells. FIG. 4A show a CD24, CD49f FACS sort of CD45−Ter119−CD31− mammary cells (adapted from Stingl et al, Nature. Feb. 23, 2006;439(7079):993-7).

Figure 4B:
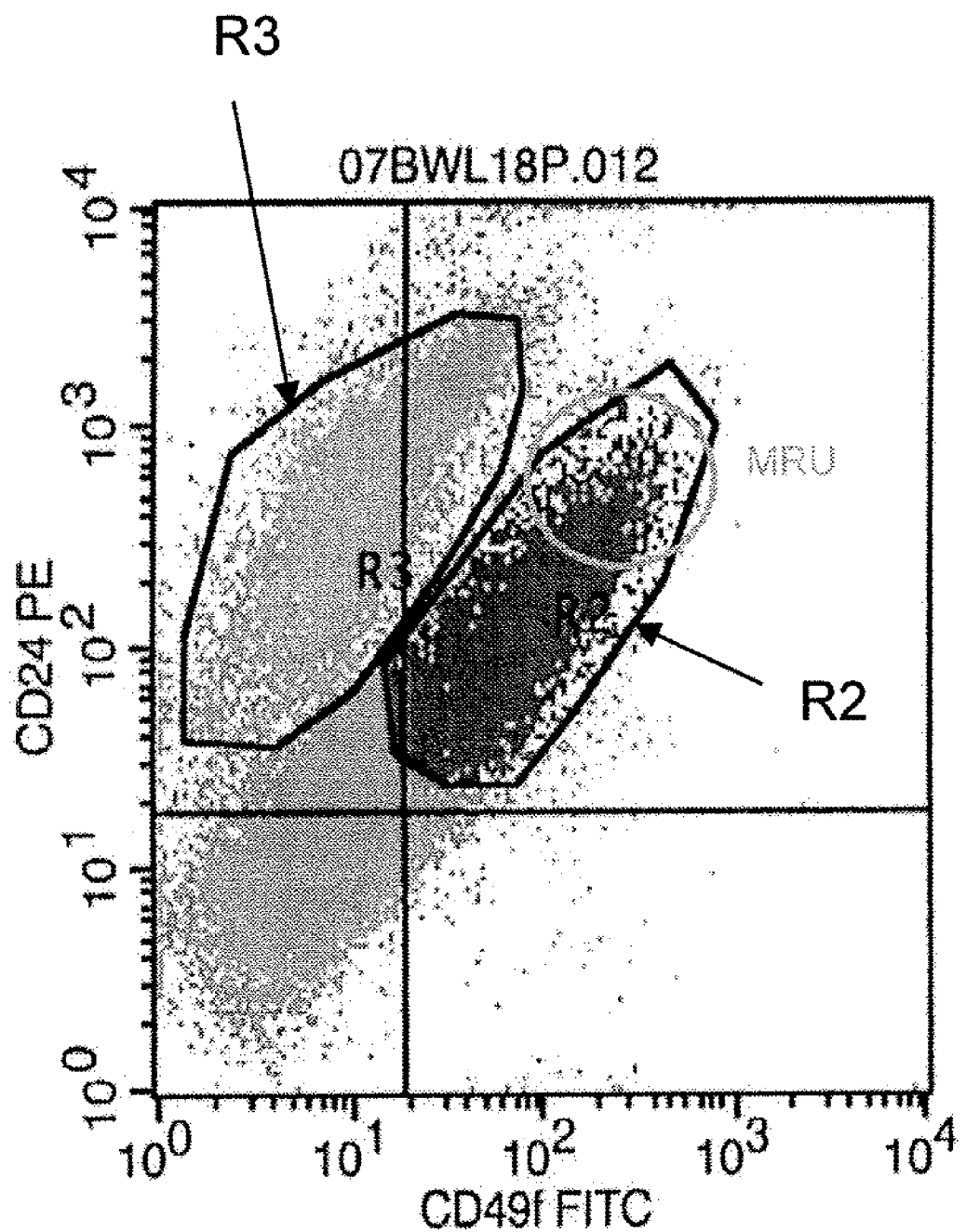
Figure 4C:
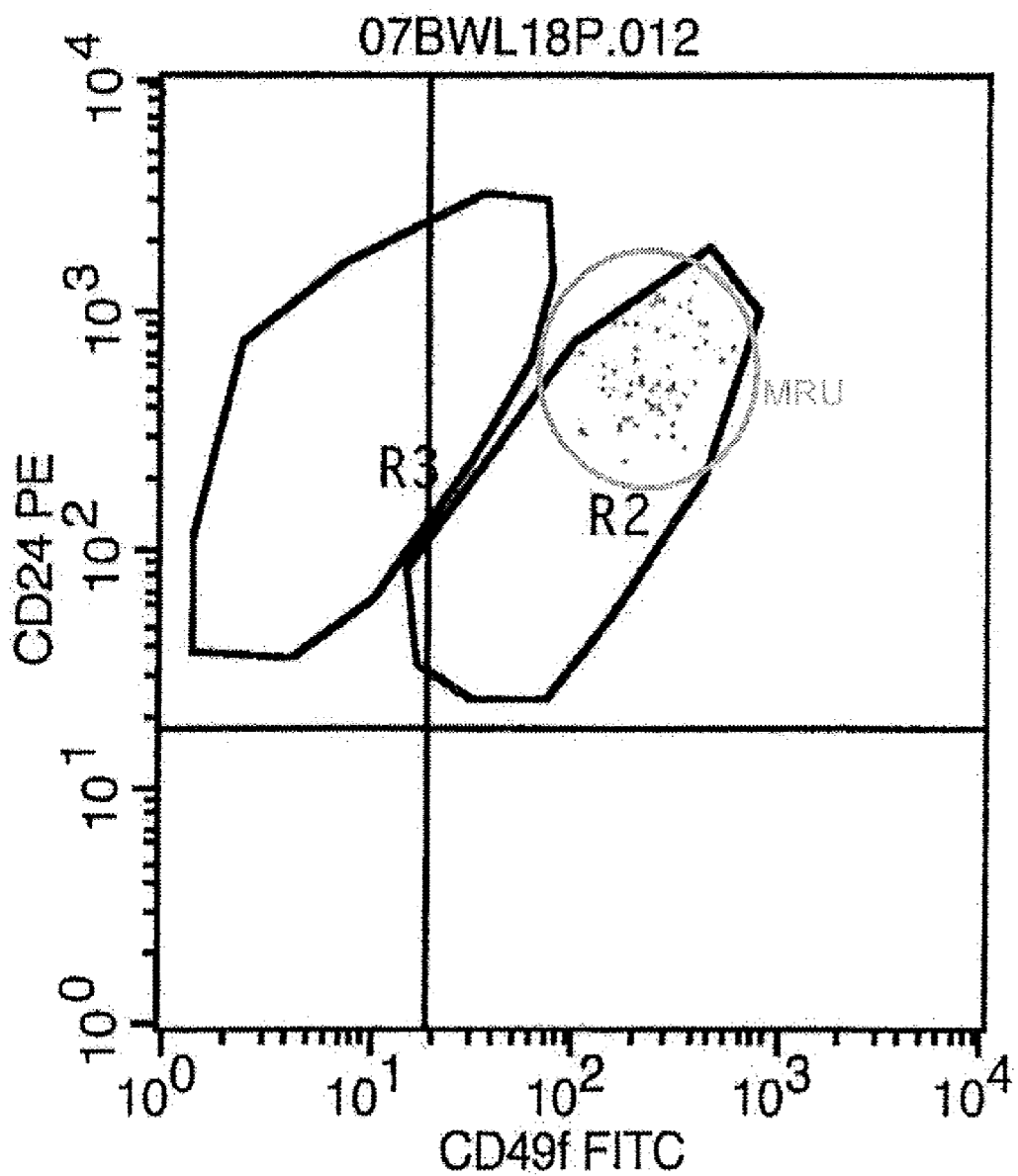

To determine which cell population in the mammary expressed LRP6, FACS was performed as described by Stingl. β-galactosidase was used as a surrogate marker for LRP6 expression. The targeting vector used to create the $Lrp6^{-/-}$ mouse strain contained the β-galactosidase gene and as a result β-galactosidase expression was directed from the Lrp6 promotor in $Lrp6^{+/-}$ and $Lrp6^{-/-}$ mice. Mammary ductal cells were isolated from adult virgin Lrp6+/− and Lrp6+/+ control females and an antibody mixture was used to selected cells that were CD45⁻Ter119⁻CD31⁻. Labelled Lrp6+/− and Lrp6+/+ cells were used with CD24 and CD49 antibodies, and DDAOG. DDAOG (9H-(1,3-dichloro-9,9-dimethylacridin-2-one-7-yl) β-D-galactopyranoside) binds β-galactosidase and has far red fluorescent properties that can be detected by FACS (Wehrman et al, Nat Genet. February 2004;36(2): 183-9.). Shown in FIG. 4B is the FACS sort for CD24 and CD49. The cell population labelled R3 contain the luminal epithelial cells, while R2 contain myoepithelial cells. The MRU cell population is indicated by the right-hand-most circle. FIG. 4C shows the cells that are positive for DDAOG, therefore expressing LRP6. DDAOG positive cells were exclusively found in the MRU cell population among the myoepithelial cells. 0.17% or 1/565 mammary cells were found to express Lrp6. Background DDAOG positive cells were not seen in the Lrp6+/+ control mammary cells (data not shown).

Histological Expression Pattern of Lrp6.

The FACS results suggested that in adult females LRP6 is expressed in a small fraction (the stem cell fraction) of the myoepithelial cell linage. In order to confirm this on the histological level, the inventors determined the expression pattern of LRP6 in mammary whole mount sections from different developmental time points. Again, β-galactosidase expression was used as a surrogate marker for Lrp6 expression. The targeting vector used to create the Lrp6$^{-/-}$ mouse strain contained the β-galactosidase gene. As a result β-galactosidase expression is directed from the Lrp6 promotor in Lrp6$^{+/-}$ and Lrp6$^{-/-}$ mice and can be used.

Figure 5A:
FIGS. 5A-C: Histological expression pattern of Lrp6 in mammary glands from new born and adult female mice. Cells that express Lrp6 stain blue. Lrp6 is expressed in most ductal cells until a few days after birth. In the adult, Lrp6 expression is restricted to a small fraction of cells located in the myoepithelial cell layer.
Figure 5B:
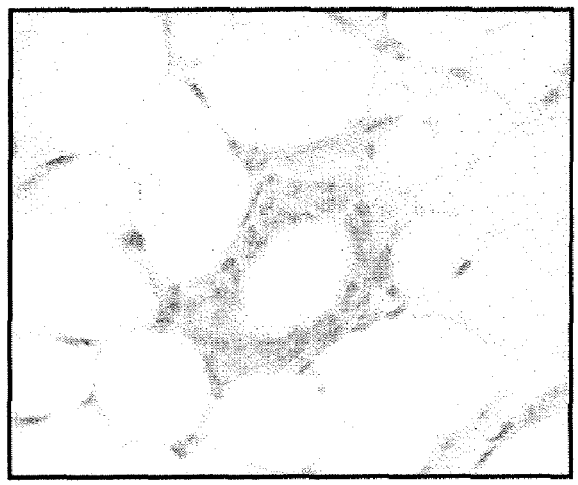
Figure 5C:
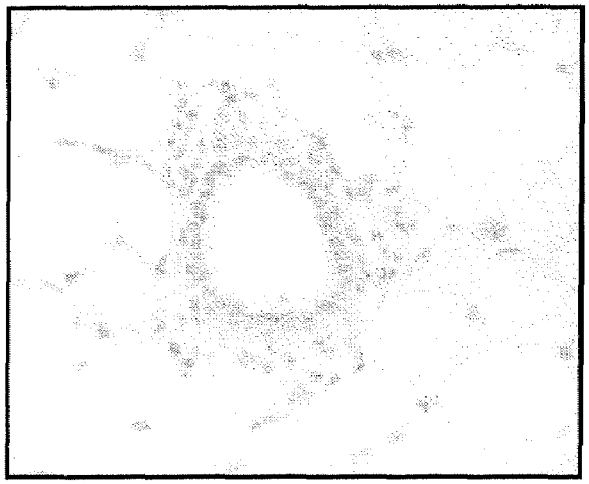

Lrp6 was expressed throughout embryonic and post-natal mammary development. During embryonic ductal development and until a few days after birth Lrp6 was expressed in both the basal myoepithelial and luminal epithelial cell layer (FIG. 5A). In juvenile and adult females Lrp6 expression was restricted to a small fraction of cells in the myoepithelial cell layer of the mammary ducts (FIG. 5B). No staining was seen in the negative control (FIG. 5C). These findings are consistent with the inventors' FACS results and LRP6 being a marker for stem cells in the adult mammary gland.

Impaired Mammary Development in Lrp6−/− Embryos.

Figure 3:
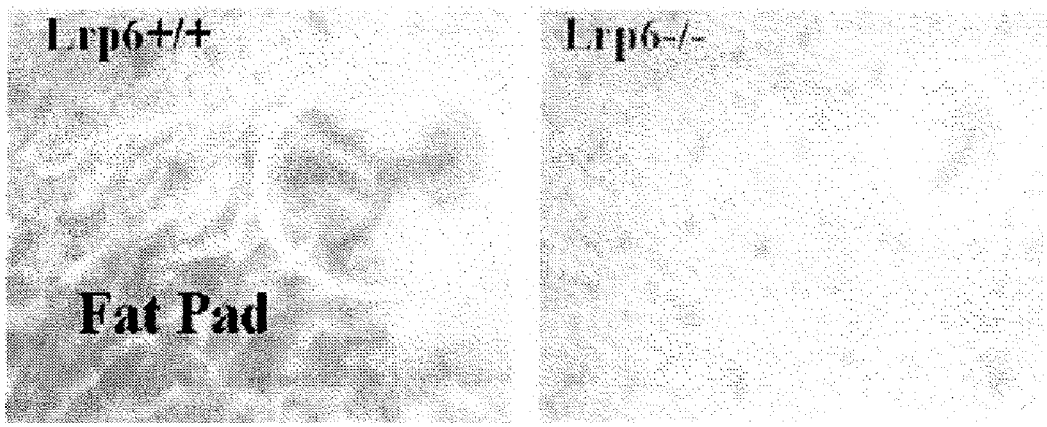
FIG. 3: LRP6-deficient mice have defective embryonic mammary development (whole mounts of skin pads isolated from the #4 or #9 mammary gland of E18.5 mice) and the stem cell compartment is formed during embryonic development. Note the presence of only a single mammary sprout in the LRP6$^{-/-}$ mouse relative to the LRP6$^{+/+}$ mouse (circled areas). The area of the fat pad (left panel) was abnormal in LRP6$^{-/-}$ mice (no equivalent area is present). Pictures are representative of the phenotype seen in three LRP6$^{-/-}$ embryos.

Lr6−/− mice die around birth [Pinson, K. I., et al., Nature, 2000. 407(6803): p. 535-8], precluding examination of the effects on LRP6 deficiency on the adult mammary. To determine whether the LRP6 receptor is required for embryonic mammary development, embryos were analyzed at embryonic day (E) 12.5 and E18.5. Mammary development begins at about E10.5 with the formation of two "mammary lines". By E12.5 the mammary lines have evolved into five pairs of lens-shaped mammary placodes presumed to contain the stem cells necessary for the outgrowth of the ductal tree. Normally at E18.5, the mammary epithelium has just started to grow into the presumptive mammary fat pad and started the branching process (FIG. 3). However, the LRP6-deficient mice reproducibly showed a lack of mammary epithelial branching, typically displaying only a single epithelial sprout (FIG. 3). Furthermore, the presumptive mammary fat pad appeared to be absent (FIG. 3).

Figure 6A:
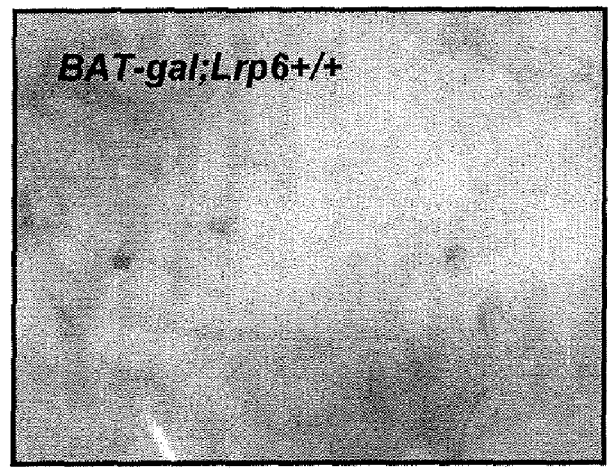
FIGS. 6A-D: Mammary BAT-gal expression in the presence or absence of Lrp6. X-gal stained BAT-gal embryo whole mounts (FIGS. 6A and 6C) and histology sections of mammary placode (FIGS. 6B and 6D) at E12.5. Cells expressing BAT-gal stain blue. At E12.5 X-gal staining reveals that the mammary placodes stain dark blue in Lrp6$^{+/+}$ embryos (FIG. 6A). In Lrp6$^{-/-}$ BAT-gal transgenic embryos the staining of the mammary placodes is significantly fainter (FIG. 6C). Arrows indicate mammary placodes number 2, 3, 4, and 5. The mammary placodes of Lrp6$^{-/-}$ embryos are significantly smaller and exhibit fewer cells with BAT-gal expression than mammary placodes from littermates carrying at least one intact copy Lrp6 (FIGS. 6B and 6D).
Figure 6B:
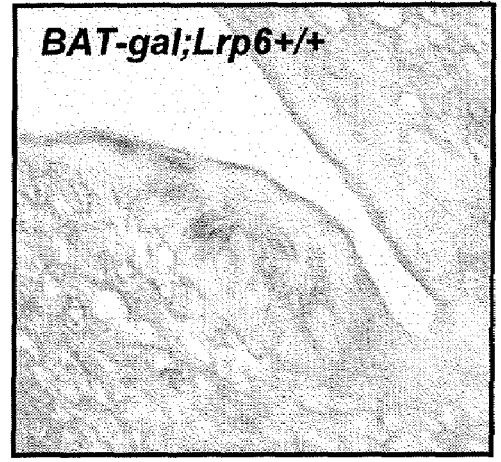

To determine whether LRP6-mediated Wnt signaling is required for the development of mammary placodes, Lrp6$^{-/-}$ and Lrp6$^{+/+}$ littermate whole embryos were analyzed at E12.5 FIGS. 6A-6D). These embryos also contained a BAT-gal β-galactosidase reporter gene that is expressed at sites of canonical pathway activity. β-galactosidase expression induced by BAT-gal reporter gene activity can be discriminated from β-galactosidase expression induced by Lrp6 promoter activity due to a large difference in the time it takes to detect the β-galactosidase by X-gal staining. While BAT-gal associated β-galactosidase expression is detected within 20 minutes of X-gal staining, Lrp6 associated β-galactosidase expression is not detected until after 12 hours of X-gal staining. The results show that loss of Lrp6 compromises canonical signaling in the developing mammary placodes and interferes with their formation (FIGS. 6A-6D). BAT-gal reporter gene activity was significantly reduced in Lrp6$^{-/-}$ embryos (FIG. 6C) relative to littermate controls (FIG. 6A). On the histological level the mammary placodes of Lrp6$^{-/-}$ embryos (FIG. 6D) were significantly smaller and contained fewer cells with reporter gene activity (FIG. 6B). This suggests that Lrp6-mediated Wnt signaling is essential for the development of the primitive mammary stem cell compartment during embryogenesis.

Reduced Number of Terminal End Buds in Juvenile Lrp6+/− Mammary Glands.

Figure 7A:
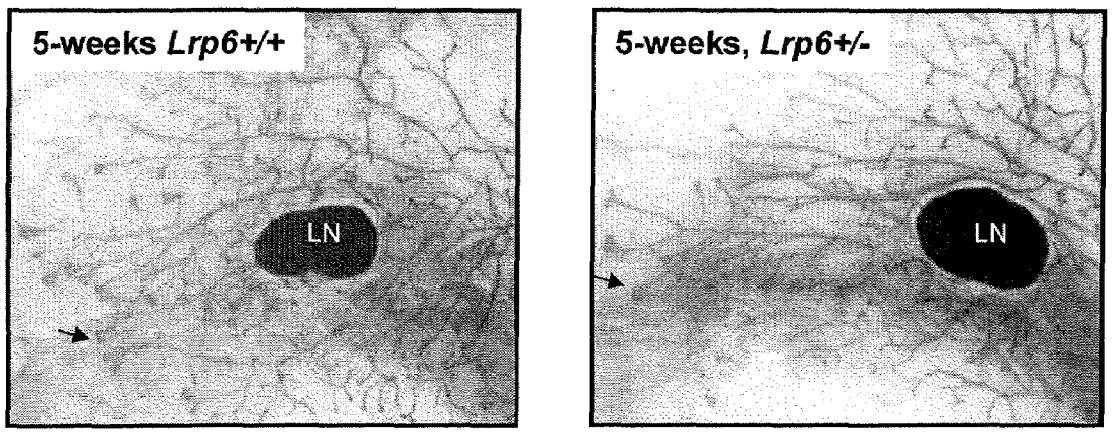
FIGS. 7A and 7B: Haploinsufficiency of Lrp6 during normal mammary development.
Figure 7B:
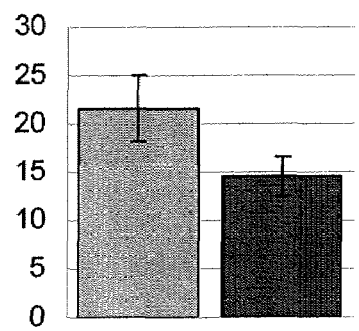

Lrp6+/− mice live and are fertile. To test whether Lrp6 is required for post-natal mammary development, ductal branching and extension were examined in virgin Lrp6+/− females. Whole-mount preparations of inguinal mammary glands are shown in (FIG. 7A). The number of terminal end buds (TEBs) was reduced by 32% in juvenile Lrp6+/− mice compared with littermate wild-type mice (p=3.8×10$^{-6}$) (FIGS. 7A and 7B). TEBs are club-shaped epithelial thickenings at the distal ends of growing ducts presumed to be rich in mammary stem cells (Kenny—J Biomed Biotechnol. 2001;1(3):133-143.), and are the sites of most rapid cell proliferation. The branching complexity in adult mice is a function of terminal end bud activity during juvenile ductal extension. Morphometric analysis showed that the branching complexity of adult Lrp6$^{+/-}$ glands was decreased by 15% compared with littermate wild-type mice (data not shown).

Lrp6+/− Mice Are Resistant to MMTV-Wnt1-Induced Tumorgenesis.

Figure 8A:
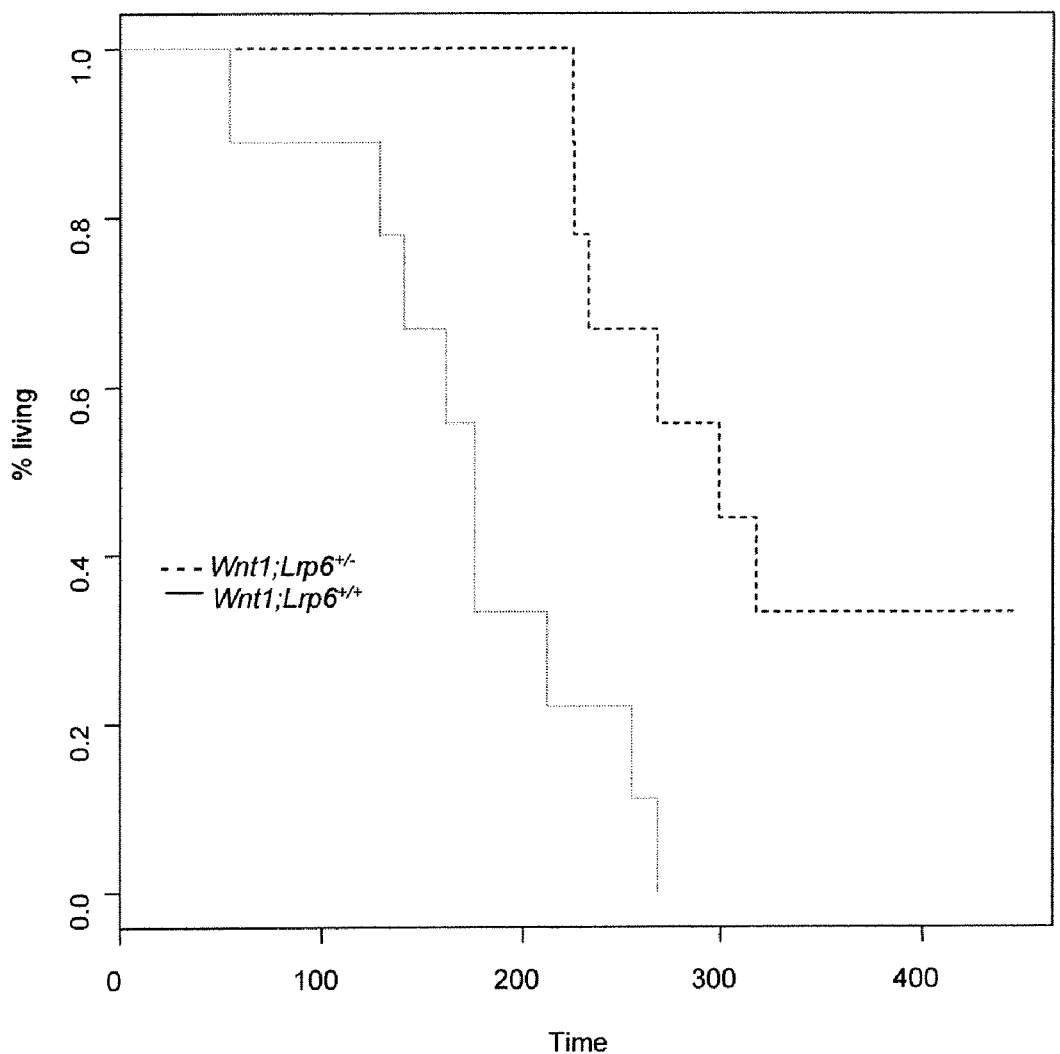
FIGS. 8A ad 8B: Emergence of Wnt1-induced mammary tumors is delayed in Lrp6$^{+/-}$ mice. Nine Lrp6$^{+/+}$ and 9 Lrp6$^{+/-}$ Wnt1 transgenic female mice were palpated weekly and dates of tumor appearance recorded.
Figure 8B:
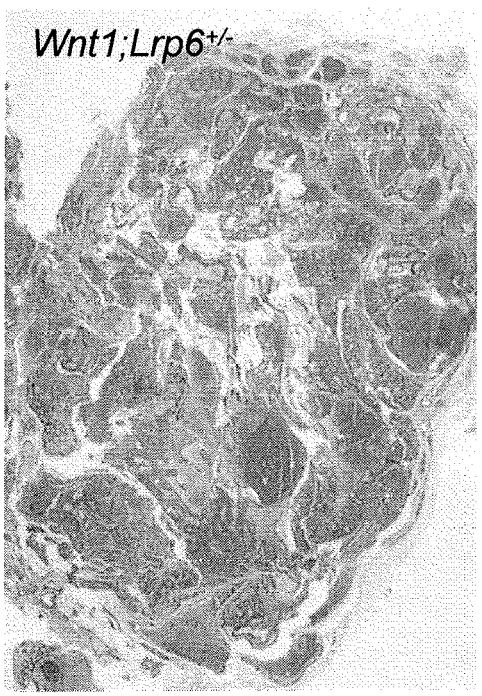
FIG. 8B shows standard histopathological evaluation showed that Lrp6$^{+/+}$ and Lrp6$^{+/-}$ mammary tumors are moderately differentiated alveolar adenocarcinomas with mixed lineage differentiation.

Female mice expressing the Wnt1 gene under the control of the MMTV promoter reproducibly develop mammary adenocarcinomas within one year (Tsukamoto A S—Cell. November. 1988 18,;55(4):619-25.). The tumors develop in a context of widespread hyperplasia. The hyperplastic mammary tissue has been shown to contain an increased fraction of mammary stem/progenitor cells that are thought to directly give rise to transformed cells (Alexander—Proc Natl Acad Sci U S A. Mar. 23, 2004;101(12):4158-63., Li - Proc Natl Acad Sci U S A. Dec. 23, 2003;100(26):15853-8.). Tumors arising from stem/progenitor cells often show mixed lineage differentiation and mammary tumors induced by Wnt1 indeed contain cells from both epithelial lineages (Owens D M, Watt F M.—Nat Rev Cancer. June 2003;3(6):444-51, Wnt1 transgenic mammary tissue and tumors normally express LRP6 (FIGS. 1A-1C). To test whether LRP6-mediated Wnt signaling is required for Wnt1-induced tumorigenesis, the development of mammary tumors in Wnt1;Lrp6$^{+/-}$ and Wnt1;Lrp6$^{+/+}$ female mice was monitored. The gene dose of Lrp6 had a dramatic effect on Wnt1-induced tumorigenesis. Tumor appearance was significantly delayed in Wnt1; Lrp6$^{+/-}$ mice (p=0.001). Within 10 months, 100% of Wnt1; Lrp$^{+/+}$ females developed tumors with a median time of onset of 25 weeks, and 50% of Wnt1;Lrp6$^{+/-}$ females formed tumors with a median time of onset of 43 weeks (FIG. 8A). Histopathological examination of the tumors in this study revealed that all Lrp6$^{+/+}$ and Lrp6$^{+/-}$ tumors were moderately differentiated alveolar mammary adenocarcinomas and exhibited show mixed lineage differentiation (FIG. 8B). Taken together, these data suggest that Lrp6$^{+/-}$ tumors also originate from the mammary progenitor cell population. The delay in tumorigenesis could thus be explained by a reduction in the number of transformable progenitor cells.

LRP6 is Expressed in Human Basal Like Breast Cancer.

There are several molecular subgroups of human breast cancer. Basal-like breast cancer (BLC) is a newly recognized subtype, which express genes that are characteristic of basal epithelial cells, and are associated with poor relapse-free and overall survival (Finnegan, T. G., Carey, L. A., Gene-expression analysis and the basal-like breast cancer subtype. Future Oncol. February 2007;3(1):55-63. Review).

The tumors are estrogen receptor-negative and HER2/ErbB2-negative and are often referred to as triple negative (since they also lack expression of the progesterone receptor). A number of studies have suggested that the tumor precursor of BLC is a mammary stem cell. Yehiely F et al. Trends Mol Med. November 2006;12(11):537-44; Birnbaum D et al. Int J Oncol. August 2004;25(2):249-58. However, the genetic alterations that are responsible for these tumors are not well understood, thereby hindering efforts to develop targeted therapies.

Figure 9A:
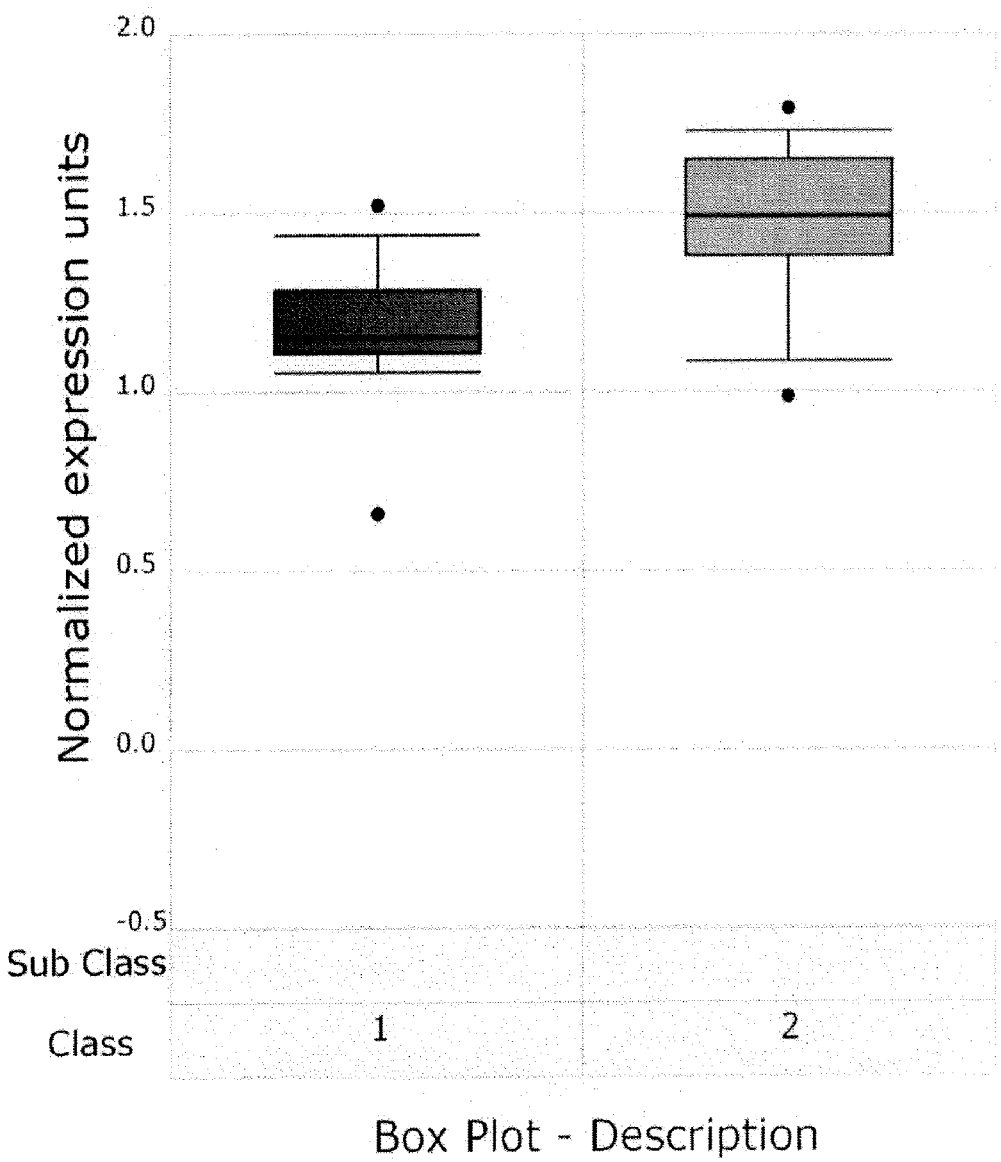
FIGS. 9A-9C show LRP6 mRNA expression level is upregulated in basal-like breast cancer (BLC). The normalized mRNA expression values of LRP6 in BLC (class 2) and non-BLC (class 1) breast tumors are shown in FIG. 9A and FIG. 9B (Richardson and Farmer studies, respectively). The line inside the boxes represents the sample with the median expression value of LRP6. The upper and lower bars represent samples with LRP6 expression values in the 75$^{th}$ percentile and in the 25$^{th}$ percentile, respectively. Asterisks indicate samples with highest or lowest LRP6 expression values. Shown in FIG. 9C is a comparison of the normalized mRNA expression values of LRP6 in 18 BLC and 20 non-BLC subtype tumors and seven normal breast (n) samples (expression values were downloaded from Richardson et al. Cancer Cell. 2006 February;9(2):121-32). The scales are in log 2.
Figure 9B:
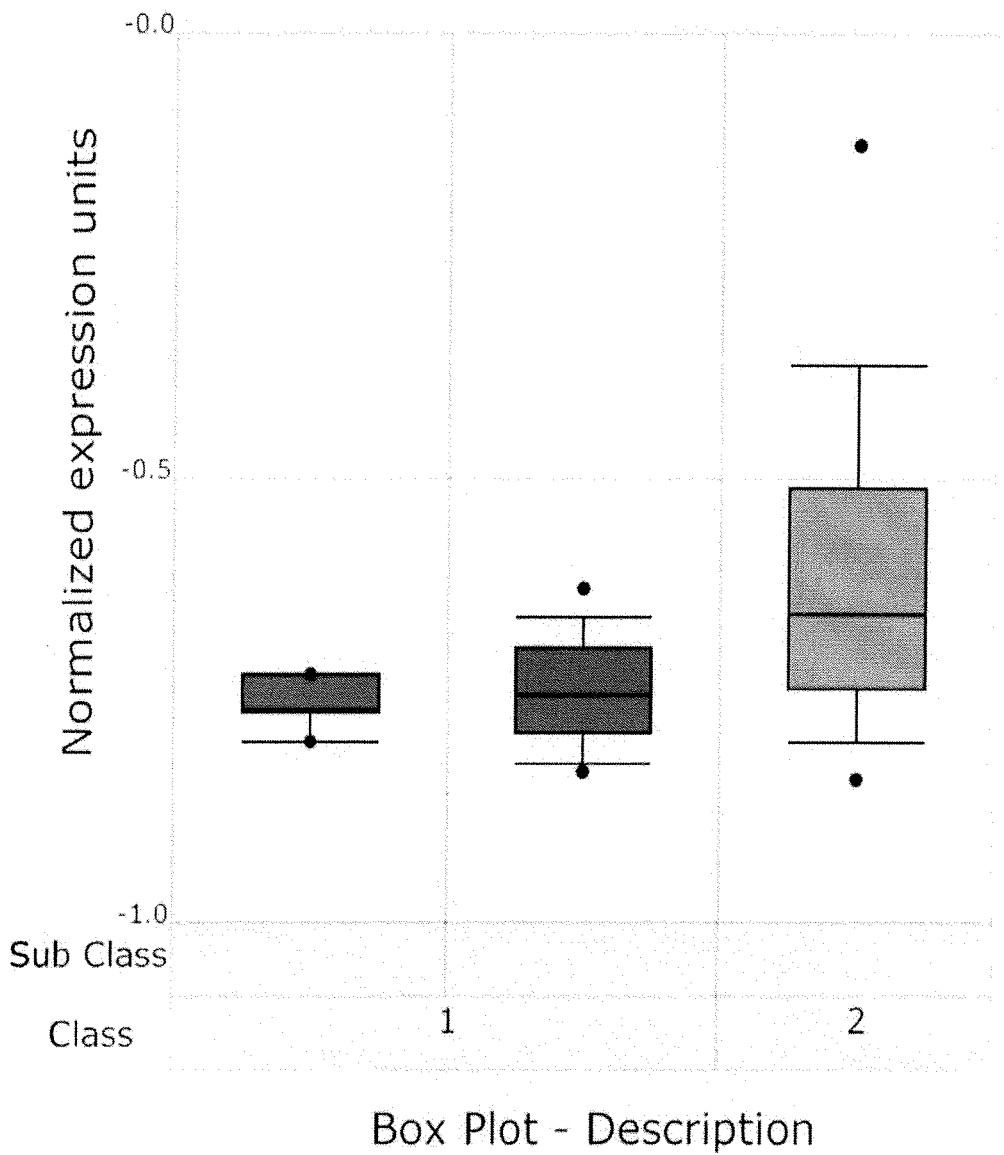

In order to investigate whether LRP6 is expressed in BLC the inventors analyzed the data sets of two published gene expression studies (Richardson et al. Cancer Cell. February 2006;9(2):121-32 and Farmer et al. Oncogene. Jul. 7, 2005; 24(29):4660-71) using the software Oncomine. The inventors found that the population of breast cancer patients with tumors of the BLC subtype express a higher level of LRP6 in the tumor cells at the mRNA level than the population of breast cancer patients with tumors that fall into the other subgtypes ($p=3.5 \times 10^{-5}$; Richardson et al. data analyzed) and ($p=0.009$; Farmer, et al. data analyzed) (FIGS. 9A and 9B). Therefore LRP6 could be used as a marker to diagnose BLC and as a drug target for breast cancer therapies.

Figure 6C:
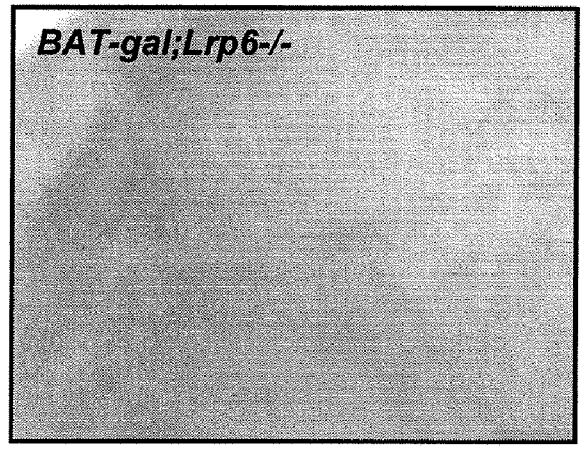
Figure 6D:
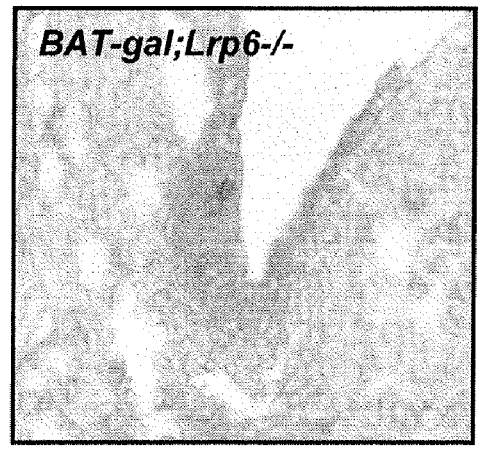
Figure 8B:
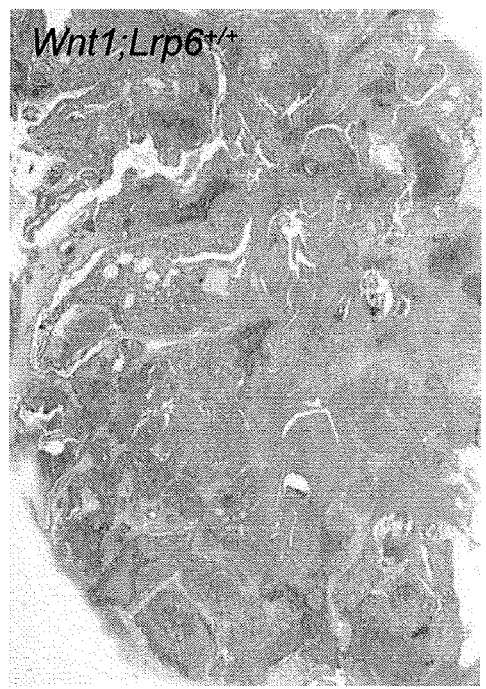

In summary, disclosed herein is a requirement for the Wnt co-receptor Lrp6 in normal mammary morphogenesis and tumor formation mediated by putative ductal stem cells. Importantly, $Lrp6^{+/-}$ mice are resistant to Wnt1-induced tumors, which have been shown to be derived from the mammary stem/progenitor cell population (FIG. 8). These mice exhibit a delay in tumorigenesis that is associated with reduced Wnt1-induced hyperplasia. In addition to the tumor-resistance phenotype, loss of Lrp6 impairs various stem cell activities required for normal mammary development (FIG. 6 and 7). $Lrp6^{-/-}$ embryos also exhibit substantially impaired canonical Wnt signaling in the primitive stem cell compartment of the mammary placode (FIGS. 6C and 6D). Most importantly, the inventors also show that Lrp6 is specifically expressed in the mammary stem cell fraction by FACS (FIG. 4C).

Canonical Wnt signaling has been implicated in the regulation of various stem cells including hematopoietic, intestinal, and epidermal stem cells (30). For example, soluble Wnt proteins promote growth and inhibit differentiation in hematopoietic stem cells (2). Wnt signaling also inhibits the differentiation of stem cells in the intestinal epithelium and in hair follicles (31, 32). Importantly, in many of the same tissues where the Wnt pathway controls stem cells, deregulation of Wnt signaling leads to tumor formation. Stabilization of β-catenin in the intestinal epithelium or overexpression of β-catenin in the epidermis results in the development of intestinal adenomas or hair tumors, respectively (33, 34). This suggests that Wnt ligands can initiate tumor formation through altered regulation of stem cell populations. Consistently, mice that overexpress Wnt signaling effectors in the mammary epithelium develop tumors with stem/progenitor cell properties, in contrast to mice overexpressing several other oncogenes (19).

The pre-neoplastic hyperplasia contains an increased fraction of cells positive for molecular markers that have been associated with mammary progenitor cells, and the likelihood of progression to carcinoma correlates with the overall number of progenitor cells (17, 19, 20). In addition, mammary ductal cells from pre-neoplastic Wnt1 transgenic mice show an increased frequency of cells with stem cell activity, measured by transferring limiting dilutions of cells to fat pads in vivo (17, 20). This finding again demonstrates the ability of the Wnt pathway to target stem/progenitor cells for transformation, possibly reflecting a role of the Wnt pathway in the self-renewal of normal breast epithelium.

Herein disclosed is the loss of Lrp6-mediated canonical Wnt signaling impairs the mammary stem cell compartment. Furthermore, LRP6 is specifically expressed by $CD24^{medium}CD49^{high}$ mammary stem cells. During normal development, the ductal tree fills the mammary fat pad by the end of puberty and TEBs disappear. In $Lrp6^{+/-}$ females, juvenile ductal branching and extension is supported by fewer TEBs and is significantly delayed (FIGS. 7A and 7B). The ductal branching of adult $Lrp6^{+/-}$ mammary glands is reduced by 15%. There are various ways to explain why $Lrp6^{+/-}$ mammary glands are relatively normal but contain a reduced number of stem cells: 1) fewer primitive mammary stem cells develop (leading to very low stem cell fractions in the adult mammary gland, 2) the proportion of stem cells dividing by self-renewal (and symmetric division) is decreased, leading to progenitor-based organogenesis (either because the stem cell niche is ineffective, or the cells differentiate precociously), 3) canonical Wnt signaling is required for stem/progenitor survival (35). The inventors have no data to support or refute the second and third proposals, but in support of the first proposal, our analysis of Wnt reporter mice shows that $Lrp6^{-/-}$ embryos develop abnormally small mammary placodes with significantly reduced canonical signaling relative to littermate controls. Previous literature on Wnt reporter mice have shown that canonical Wnt signaling is specifically active during embryonic mammary development (13, 14). Furthermore, Wnt signaling is absolutely required, because mammary placodes fail to develop in transgenic mice overexpressing the Wnt inhibitor Dkk1 (6). Dkk1 inhibits the Wnt signaling pathway by binding to, and presumably inactivating, LRP5 and LRP6.

Figure 9C:
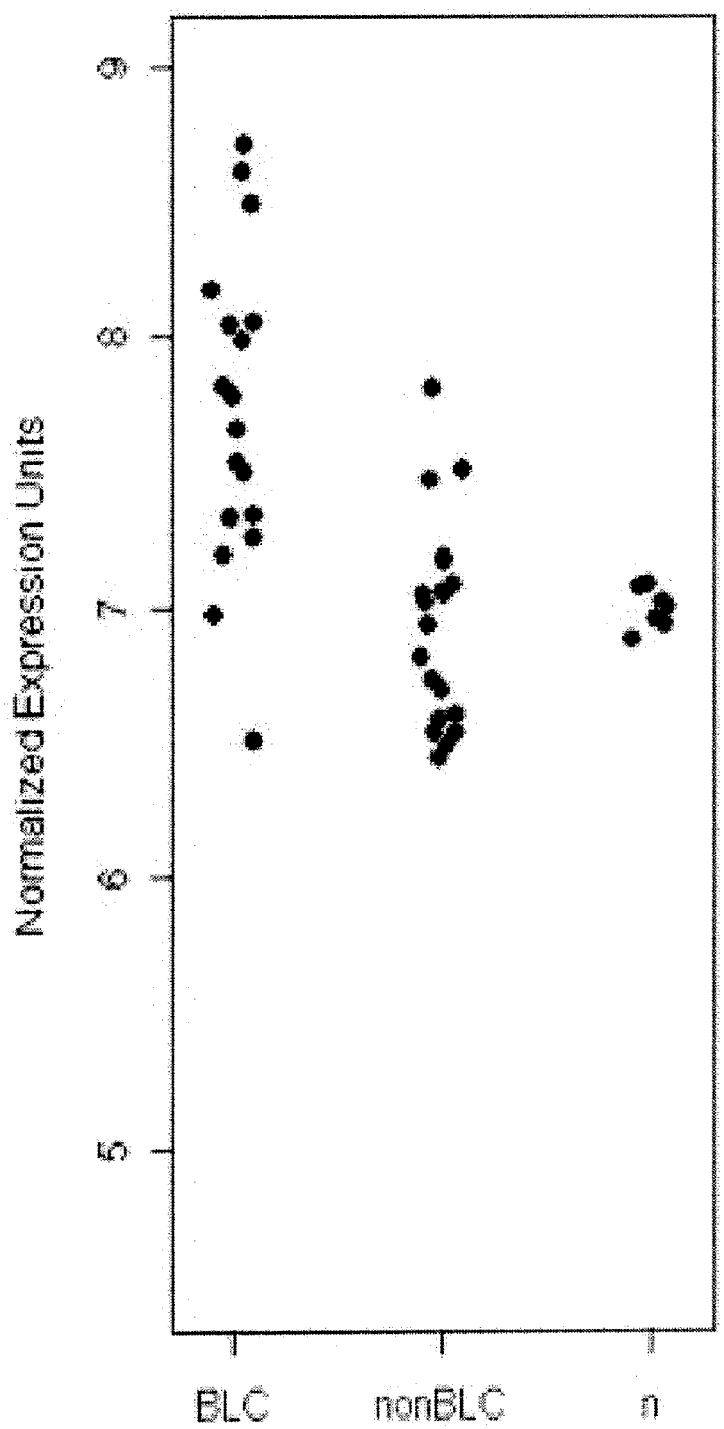

Finally, a growing body of evidence suggests that specific subtypes of the most common human tumors—including breast (36), lung (37), and colon (38)—originate in stem cell compartments. Signaling pathways that regulate stem cell activity could therefore be effective drug targets. In fact, several studies have shown that activation of canonical Wnt signaling is common in human breast cancer (39-41). The inventors show that in $Lrp6^{+/-}$ mice, the response to ectopically expressed Wnt1 is inhibited as demonstrated by an increased latency in tumor development (FIG. 8). The mammary tumors that arise in $Lrp6^{+/-}$ mice exhibit histology and differentiation similar to those of Lrp6-expressing tumors (FIG. 8), suggesting that $Lrp6^{+/-}$ tumors also originate from the mammary progenitor cell population. The delay in tumorigenesis could thus be explained by a reduction in the number of transformable progenitor cells. In concordance with this, the inventors found that LRp6 is upregulated in a subtype of human breast cancer presumed to originate from the mammary stem cell compartment (FIG. 9). Taken together, these findings suggest that the Lrp6 receptor may be a highly effective target for inhibiting oncogenic canonical Wnt signaling in human malignancies.

Example 2

Method of Screening for LRP6-Specific Inhibitors

First, establish mouse embryonic fibroblasts (MEFs) from control mouse embryos (CONTROL) or from Lrp5-deficient (Lrp5$^{-/-}$) embryos. These MEFs would also contain a reporter gene (Bat-Gal) that directs the expression of β-galactosidase under the control of a β-catenin-responsive promoter. Thus, β-catenin signaling activity could be measured by analyzing the level of β-galactosidase activity in lysates prepared from these cells. Next, expose CONTROL and Lrp5$^{-/-}$ MEFs to exogenously added Wnt ligands which are commercially available. After 4-12 hours, measure the amount of β-galactosidase activity in the lysates. Any activity noted in the Lrp5$^{-/-}$ lysates would be due to Wnt signaling through the LRP6 molecule. Then, screen for compounds that inhibit the ability of Wnt ligands to increase β-galactosidase activity in Lrp5$^{-/-}$ MEFs. Compounds identified in this screen would subsequently be used to test their ability to inhibit signaling in CONTROL MEFs. Those that inhibit signaling in Lrp5$^{-/-}$ but not CONTROL, MEFs would be strong candidates to be specific inhibitors of LRP6-mediated signaling.

REFERENCES

1. Nusse, R. (2005) *Cell Res* 15, 28-32.
2. Reya, T., Duncan, A. W., Ailles, L., Domen, J., Scherer, D. C., Willert, K., Hintz, L., Nusse, R. & Weissman, I. L. (2003) *Nature* 423, 409-14.
3. Sharpe, C., Lawrence, N. & Martinez Arias, A. (2001) *Bioessays* 23, 311-8.
4. Schweizer, L. & Varmus, H. (2003) *BMC Cell Biol* 4, 4.
5. Liu, G., Bafico, A. & Aaronson, S. A. (2005) *Mol Cell Biol* 25, 3475-82.
6. Andl, T., Reddy, S. T., Gaddapara, T. & Millar, S. E. (2002) *Dev Cell* 2, 643-53.
7. van Genderen, C., Okamura, R. M., Farinas, I., Quo, R. G., Parslow, T. G., Bruhn, L. & Grosschedl, R. (1994) *Genes Dev* 8, 2691-703.
8. Hsu, W., Shakya, R. & Costantini, F. (2001) *J Cell Biol* 155, 1055-64.
9. Brisken, C., Heineman, A., Chavarria, T., Elenbaas, B., Tan, J., Dey, S. K., McMahon, J. A., McMahon, A. P. & Weinberg, R. A. (2000) *Genes Dev* 14, 650-4.
10. Tepera, S. B., McCrea, P. D. & Rosen, J. M. (2003) *J Cell Sci* 116, 1137-49.
11. Imbert, A., Eelkema, R., Jordan, S., Feiner, H. & Cowin, P. (2001) *J Cell Biol* 153, 555-68.
12. Veltmaat, J. M., Mailleux, A. A., Thiery, J. P. & Bellusci, S. (2003) *Differentiation* 71, -17.
13. Chu, E. Y., Hens, J., Andl, T., Kairo, A., Yamaguchi, T. P., Brisken, C., Glick, A., Wysolmerski, J. J. & Millar, S. E. (2004) *Development* 131, 4819-29.
14. Boras-Granic, K., Chang, H., Grosschedl, R. & Hamel, P. A. (2006) *Dev Biol*.
15. Hennighausen, L. & Robinson, G. W. (1998) *Genes Dev* 12, 449-55.
16. Stingl, J., Eirew, P., Ricketson, I., Shackleton, M., Vaillant, F., Choi, D., Li, H. I. & Eaves, C. J. (2006) *Nature* 439, 993-7.
17. Shackleton, M., Vaillant, F., Simpson, K. J., Stingl, J., Smyth, G. K., Asselin-Labat, M. L., Wu, L., Lindeman, G. J. & Visvader, J. E. (2006) *Nature* 439, 84-8.
18. Tsukamoto, A. S., Grosschedl, R., Guzman, R. C., Parslow, T. & Varmus, H. E. (1988) *Cell* 55, 619-25.
19. Li, Y., Welm, B., Podsypanina, K., Huang, S., Chamorro, M., Zhang, X., Rowlands, T., Egeblad, M., Cowin, P., Werb, Z., Tan, L. K., Rosen, J. M. & Varmus, H. E. (2003) *Proc Natl Acad Sci USA* 100, 15853-8.
20. Liu, B. Y., McDermott, S. P., Khwaja, S. S. & Alexander, C. M. (2004) *Proc Natl Acad Sci USA* 101, 4158-63.
21. Owens, D. M. & Watt, F. M. (2003) *Nat Rev Cancer* 3, 444-51.
22. Holmen, S. L., Giambernardi, T. A., Zylstra, C. R., Buckner-Berghuis, B. D., Resau, J. H., Hess, J. F., Glatt, V., Bouxsein, M. L., Ai, M., Warman, M. L. & Williams, B. O. (2004) *J Bone Miner Res* 19, 2033-40.
23. Maretto, S., Cordenonsi, M., Dupont, S., Braghetta, P., Broccoli, V., Hassan, A. B., Volpin, D., Bressan, G. M. & Piccolo, S. (2003) *Proc Natl Acad Sci USA* 100, 3299-304.
24. Babij, P., Zhao, W., Small, C., Kharode, Y., Yaworsky, P. J., Bouxsein, M. L., Reddy, P. S., Bodine, P. V., Robinson, J. A., Bhat, B., Marzolf, J., Moran, R. A. & Bex, F. (2003) *J Bone Miner Res* 18, 960-74.
25. Kordon, E. C. & Smith, G. H. (1998) *Development* 125, 1921-30.
26. Donehower, L. A., Godley, L. A., Aldaz, C. M., Pyle, R., Shi, Y. P., Pinkel, D., Gray, J., Bradley, A., Medina, D. & Varmus, H. E. (1995) *Genes Dev* 9, 882-95.
27. Clarke, R. B., Spence, K., Anderson, E., Howell, A., Okano, H. & Potten, C. S. (2005) *Dev Biol* 277, 443-56.
28. Kenney, N. J., Smith, G. H., Lawrence, E., Barrett, J. C. & Salomon, D. S. (2001) *J Biomed Biotechnol* 1, 133-143.
29. Williams, J. M. & Daniel, C. W. (1983) *Dev Biol* 97, 274-90.
30. Reya, T. & Clevers, H. (2005) *Nature* 434, 843-50.
31. Korinek, V., Barker, N., Moerer, P., van Donselaar, E., Huls, G., Peters, P. J. & Clevers, H. (1998) *Nat Genet* 19, 379-83.
32. Huelsken, J., Vogel, R., Erdmann, B., Cotsarelis, G. & Birchmeier, W. (2001) *Cell* 105, 533-45.
33. Dietrich, W. F., Lander, E. S., Smith, J. S., Moser, A. R., Gould, K. A., Luongo, C., Borenstein, N. & Dove, W. (1993) *Cell* 75, 631-9.
34. Gat, U., DasGupta, R., Degenstein, L. & Fuchs, E. (1998) *Cell* 95, 605-14.
35. Paguirigan, A., Beebe, D. J., Liu, B. & Alexander, C. (2006) *Eur J Cancer* 42, 1225-36.
36. Al-Hajj, M., Wicha, M. S., Benito-Hernandez, A., Morrison, S. J. & Clarke, M. F. (2003) *Proc Natl Acad Sci USA* 100, 3983-8.
37. Kim, C. F., Jackson, E. L., Woolfenden, A. E., Lawrence, S., Babar, I., Vogel, S., Crowley, D., Bronson, R. T. & Jacks, T. (2005) *Cell* 121, 823-35.
38. Radtke, F. & Clevers, H. (2005) Science 307, 1904-9.
39. Lin, S. Y., Xia, W., Wang, J. C., Kwong, K. Y., Spohn, B., Wen, Y., Pestell, R. G. & Hung, M. C. (2000) *Proc Natl Acad Sci USA* 97, 4262-6.
40. Ugolini, F., Charafe-Jauffret, E., Bardou, V. J., Geneix, J., Adelaide, J., Labat-Moleur, F., Penault-Llorca, F., Longy, M., Jacquemier, J., Birnbaum, D. & Pebusque, M. J. (2001) *Oncogene* 20, 5810-7.
41. Klopocki, E., Kristiansen, G., Wild, P. J., Klaman, I., Castanos-Velez, E., Singer, G., Stohr, R., Simon, R., Sauter, G., Leibiger, H., Essers, L., Weber, B., Hermann, K., Rosenthal, A., Hartmann, A. & Dahl, E. (2004) *Int J Oncol* 25, 641-9.

What is claimed is:

1. A method for selecting mammary stem cells or mammary tumor stem cells from a population of mammary cells mammary tumor cells, the method comprising the steps of:
   obtaining a population of mammary cells or mammary tumor cells containing one or more somatic mammary stem cells or mammary tumor stem cells;
   contacting said population of mammary cells or mammary tumor cells with an LRP6 antibody; and
   selecting cells that bind to the antibody.

2. The method of claim 1, wherein the population of mammary cells or mammary tumor cells is a population of human, mouse, or rat cells.

3. The compound of claim 1 wherein the antibody is attached to a solid matrix.

4. The method of claim 1 wherein cells that bind to the antibody are selected by flow cytometry.

5. The method of claim 4 wherein the top 10% or higher of the highest LRP6 expressing mammary cells or mammary tumor cells of the total population is selected.

6. The method of claim 1, wherein the method is for enriching a population of mammary cells for somatic mammary stem cells.

7. The method of claim 6 further comprising the step of contacting said population of mammary cells with an antibody against a cell surface marker for endothelial cells, hematopoietic cells, or stromal cells wherein cells that bind to the anti-LRP6 antibody but not the antibody against the cell surface marker for endothelial cells, hematopoietic cells, or stromal cells are selected.

8. The method of claim 6, wherein at least 1% of the selected cells are somatic mammary stem cells.

9. The method of claim 6, wherein at least 5% of the selected cells are somatic mammary stem cells.

* * * * *

UNITED STATES PATENT AND TRADEMARK OFFICE
CERTIFICATE OF CORRECTION

| | | |
|---|---|---|
| PATENT NO. | : 7,622,267 B2 | |
| APPLICATION NO. | : 11/755638 | |
| DATED | : November 24, 2009 | |
| INVENTOR(S) | : Bart O. Williams et al. | |

It is certified that error appears in the above-identified patent and that said Letters Patent is hereby corrected as shown below:

Column 2
line 25 "initiates" should be -- initiate --.

Column 3
lines 4 and 5 "Dkk1" should be -- Dkk-1 --.

Column 4
lines 10-11 Delete "(Is this correct)".
lines 15, 22 and 47 "Dkk1" should be -- Dkk-1 --.

Column 5
lines 16-17 "Jackson, E. L." is made into a new paragraph after "E." and should not be.

Column 6
line 20 After "154(2):325-9]" insert -- ) --.
line 25 After "109]" insert -- . --.

Column 7
line 61 "4158-4163) (Shackleton" should be -- 4158-4163; Shackleton --.
line 65 "increase" should be -- increased --.

Column 10
lines 36 and 37 "Lrp6" should be -- LRP6 --.
line 61 "locus.)" should be -- locus). --.
line 64 "B-gal" should be -- β-gal --.

Column 11
line 11 "Lrp6" should be -- LRP6 --.
line 22 "Lrp6" should be -- LRP6 --.

Signed and Sealed this
Twelfth Day of July, 2011

David J. Kappos
*Director of the United States Patent and Trademark Office* line 24 "Lrp6" should be -- LRP6 --.
line 25 "Lrp6" should be -- LRP6 --.
line 29 "Lrp6" should be -- LRP6 --.
line 33 "Lrp6$^{+/+}$" should be -- LRP6$^{+/+}$ --.
line 34 "Lrp6$^{-/-}$" should be -- LRP6$^{-/-}$ --.
line 37 "Lrp6$^{-/-}$" should be -- LRP6$^{-/-}$ --.
line 40 "copy Lrp6" should be -- copy of LRP6 --.
line 41 "Lrp6" should be -- LRP6 --.
line 44 "Lrp6+/+" should be -- LRP6$^{+/+}$ --.
line 45 "Lrp6+/-" should be -- LRP6$^{+/-}$ --.
lines 45-46 "mice. The" is made into a new paragraph after "mice." and should not be.
line 48 "Lrp6+/-" should be -- LRP6$^{+/-}$ --.
line 50 "Lrp6+/+" should be -- LRP6$^{+/+}$ --.
line 52 "ad" should be -- and --.
line 53 "delayed in Lrp6$^{+/-}$ mice. Nine Lrp6$^{+/+}$ and 9 Lrp6$^{+/-}$" should be -- delayed in LRP6$^{+/-}$ mice. Nine LRP6$^{+/+}$ and 9 LRP6$^{+/-}$ --.
lines 58-59 "evaluation showed that Lrp6$^{+/+}$ and Lrp6$^{+/-}$" should be -- evaluation which showed that LRP6$^{+/+}$ and LRP6$^{+/-}$ --.

Column 13
line 14 "1993)." should be -- 1993)). --.
line 32 "sequences" should be -- sequence --.
line 53 "a organ" should be -- an organ --.

Column 15
line 60 "CD3 1" should be -- CD31 --.

Column 16
line 63 "vise versa" should be -- vice versa --.

Column 17
line 2 "(e.g. fluorescein)" should be -- (e.g., fluorescein) --.

Column 18
line 3 "same)." should be -- same.) --.
line 28 "recovered, is" should be -- recovered is --.

Column 19
line 35 "by a variety method" should be -- by a variety of methods --.
line 36 "20030150001" should be -- 2003/0150001 --.
line 37 "term" should be -- terms --.
line 54 "Lrp5$^{-/-}$" should be -- LRP5$^{-/-}$ --.
line 55 "murine animals murine embryonic" should be -- murine animals, murine embryonic --.
line 59 "Lrp5$^{-/-}$" should be -- LRP5$^{-/-}$ --.

CERTIFICATE OF CORRECTION (continued)

U.S. Pat. No. 7,622,267 B2

Column 20
lines 7-8 "vise versa" should be -- vice versa --.
line 10 "vise versa" should be -- vice versa --.
line 42 "IGF-1" should be -- IGF-I --.
lines 45-46 delete "connexin43".
line 56 "vise versa" should be -- vice versa --.

Column 21
line 50 "Given the" should be -- Given that --.

Column 22
line 36 "are" should be -- is --.
line 46 "viruses" should be -- virus' --.
line 53 "virus" should be -- viruses --.
line 63 "(include" should be -- (including --.

Column 24
line 42 "Lrp6" should be -- LRP6 --.

Column 25
line 33 "isotopes paramagnetic" should be -- isotopes, paramagnetic --.
lines 44-46 ".sup.3H, .sup.124I, .sup.125I, .sup.131I, .sup.35S and .sup.14C. In addition, .sup.131I" should be -- $^{3}H$, $^{124}I$, $^{125}I$, $^{131}I$, $^{35}S$ and $^{14}C$. In addition, $^{131}I$ --.
lines 55, 56, 61 and 67 ".™." should be -- ™ --.

Column 26
line 12 "a anti-LRP6" should be -- an anti-LRP6 --.
line 20 ".sup.152Eu+" should be -- $^{152}Eu^{+}$ --.
line 25 "NH.sub.2" should be -- $NH_2$ --.
lines 29-31 ".sup.99Tc, .sup.123I, .sup.125I, .sup.131I, .sup.111In, .sup.97Ru, .sup.67Cu, .sup.67Ga, .sup.68Ga, .sup.72As, .sup.89Zr, sup.90Y and .sup.201Tl." should be -- $^{99}Tc$, $^{123}I$, $^{125}I$, $^{131}I$, $^{111}In$, $^{97}Ru$, $^{67}Cu$, $^{67}Ga$, $^{68}Ga$, $^{72}As$, $^{89}Zr$, $^{90}Y$ and $^{201}Tl$. --.

Column 27
line 31 "1 (Van" should be -- 1, (Van --.
line 34 "803 Butler" should be -- 803; Butler --.
line 40 "1980 Ishikawa" should be -- 1980; Ishikawa --.
line 49 ".Delta.-V-steroid" should be -- Δ-V-steroid --.
line 50 ".alpha.-glycerophosphate" should be -- α-glycerophosphate --.
line 52 ".beta.-galactosidase" should be -- β-galactosidase --.

Column 28
line 30 "(Na-.sup.131I," should be -- (Na-$^{131}I$, --.
line 31 "(.sup.201TlCl)" should be -- ($^{201}TlCl$) --.
line 31 "(.sup.67Ga-citrate)" should be -- ($^{67}Ga$-citrate) --.

CERTIFICATE OF CORRECTION (continued)
U.S. Pat. No. 7,622,267 B2 line 39 "OcteroScan.®." should be -- OcteroScan® --.
line 41 "CEAScan.®." should be -- CEAScan® --.
line 41 "OncoScint.®. should be -- OncoScint® --.
line 42 "Bexxar.® should be -- Bexxar® --.
line 42 "Zevalin.®. should be -- Zevalin® --.
line 46 "Lrp6" should be -- LRP6 --.
line 50 "Lrp6" should be -- LRP6 --.
line 52 "Lrp6" should be -- LRP6 --.
line 55 "Lrp6" should be -- LRP6 --.
line 60 "Lrp6" should be -- LRP6 --.
line 66 "Lrp6" should be -- LRP6 --.

Column 29
line 51 "Sug." should be -- Aug. --.

Column 30
line 35 "Lrp6" should be -- LRP6 --.

Column 31
line 13 "Lrp6" should be -- LRP6 --.
line 16 "Lrp6$^{-/-}$" should be -- LRP6$^{-/-}$ --.
line 22 "Lrp6$^{+/-}$" should be -- LRP6$^{+/-}$ --.
line 24 "Lrp6 mouse" should be -- LRP6 mice --.
line 28 "Lrp6$^{+/-}$" should be -- LRP6$^{+/-}$ --.
line 43 "Lrp6" should be -- LRP6 --.
line 55 "Expression" should be -- Expression. --.
line 60 "X-gal" should be -- X-Gal --.

Column 32
line 2 "Lrp6+/- and Lrp6+/+" should be -- LRP6$^{+/-}$ and LRP6$^{+/+}$ --.
line 7 "X-gal" should be -- X-Gal -- (both occurrences).
line 15 "Lrp6" should be -- LRP6 --.
line 28 "β-D-galactopyranoside" should be -- β-D-galactopyranoside --.
line 29 "minute" should be -- minutes --.
line 45 "Lrp6" should be -- LRP6 --.
line 56 "show" should be -- shows --.
line 58 "et al" should be -- et al. --.
line 61 "Stingl." should be -- Stingl et al., --.
line 63 "Lrp6$^{-/-}$" should be -- LRP6$^{-/-}$ --.
line 65 "Lrp6 promotor in Lrp6$^{+/-}$ and Lrp6$^{-/-}$" should be -- LRP6 promotor in LRP6$^{+/-}$ and LRP6$^{-/-}$ --.
line 66 "Lrp6+/- and Lrp6+/+" should be -- LRP6$^{+/-}$ and LRP6$^{+/+}$ --.
line 67 "to selected" should be -- to select --.

CERTIFICATE OF CORRECTION (continued)
U.S. Pat. No. 7,622,267 B2

Column 33
lines 1 and 2 "Lrp6+/- and Lrp6+/+" should be -- LRP6$^{+/-}$ and LRP6$^{+/+}$ --.
line 4 "β-D-galactopyranoside" should be -- β-D-galactopyranoside --.
line 7 "9.)." should be -- 9). --.
line 8 "contain" should be -- contains --.
line 9 "contain" should be -- contains --.
line 15 "Lrp6" should be -- LRP6 --.
line 16 "Lrp6+/+" should be -- LRP6$^{+/+}$ --.
line 18 "Lrp6" should be -- LRP6 --.
line 21 "linage" should be -- lineage --.
line 25 "Lrp6" should be -- LRP6 --.
line 26 "Lrp6$^{-/-}$" should be -- LRP6$^{-/-}$ --.
line 28 "Lrp6" should be -- LRP6 --.
line 29 "Lrp6$^{+/-}$ and Lrp6$^{-/-}$" should be -- LRP6$^{+/-}$ and LRP6 $^{-/-}$ --.
line 30 "Lrp6" should be -- LRP6 --.
line 32 "Lrp6" should be -- LRP6 --.
line 34 "Lrp6" should be -- LRP6 --.
line 59 "Lrp6$^{-/-}$" should be -- LRP6$^{-/-}$ --.
line 60 "Lrp6$^{+/+}$" should be -- LRP6$^{+/+}$ --.
line 61 "E12.5 Figs." should be -- E12.5 (Figs. --.
line 65 "Lrp6" should be -- LRP6 --.

Column 34
line 2 "Lrp6" should be -- LRP6 --.
line 4 "Lrp6" should be -- LRP6 --.
line 7 "Lrp6$^{-/-}$" should be -- LRP6$^{-/-}$ --.
line 9 "Lrp6$^{-/-}$" should be -- LRP6$^{-/-}$ --.
line 12 "Lrp6" should be -- LRP6 --.
line 16 "Lrp6+/-" should be -- LRP6$^{+/-}$ --.
line 17 "Lrp6+/-" should be -- LRP6$^{+/-}$ --.
line 17 "Lrp6" should be -- LRP6 --.
line 19 "Lrp6+/-" should be -- LRP6$^{+/-}$ --.
line 22 "Lrp6+/-" should be -- LRP6$^{+/-}$" --.
line 31 "Lrp6$^{+/-}$" should be -- LRP6$^{+/-}$ --.
line 33 "Lrp6+/-" should be -- LRP6$^{+/-}$ --.
line 34 "Tumorgenesis" should be -- Tumorigenesis --.
line 48 "444-51," should be -- 444-51. --.
line 52 "Lrp6$^{+/-}$" should be -- LRP6$^{+/-}$ --.
line 53 "Lrp6$^{+/+}$" should be -- LRP6$^{+/+}$ --.
line 54 "Lrp6" should be -- LRP6 --.
line 56 "Lrp6$^{+/-}$" should be -- LRP6$^{+/-}$ --.
line 57 "Lrp$^{+/+}$" should be -- LRP6$^{+/+}$ --.
line 58 "Lrp6$^{+/-}$" should be -- LRP6$^{+/-}$ --.
line 61 "Lrp6$^{+/+}$ and Lrp6$^{+/-}$" should be -- LRP6$^{+/+}$ and LRP6$^{+/-}$ --.

line 63 "and exhibited show mixed" should be -- and exhibited mixed --.
line 64 "Lrp6" should be -- LRP6 --.

Column 35
line 28 "subgtypes" should be -- subtypes --.
line 33 "Lrp6" should be -- LRP6 --.
line 35 "Lrp6$^{+/-}$" should be -- LRP6$^{+/-}$ --.
line 40 "Lrp6" should be -- LRP6 --.
line 41 "(FIG." should be -- (FIGS. --.
line 42 "Lrp6$^{-/-}$" should be -- LRP6$^{-/-}$ --.
line 45 "Lrp6" should be -- LRP6 --.

Column 36
line 12 "disclosed is the" should be -- disclosed is that the --.
line 12 "Lrp6" should be -- LRP6 --.
line 15 "CD24$^{medium}$CD49$^{high}$" should be -- CD24$^{medium}$CD49f$^{high}$ --.
line 17 "Lrp6$^{+/-}$" should be -- LRP6$^{+/-}$ --.
line 20 "Lrp6$^{+/-}$" should be -- LRP6$^{+/-}$ --.
line 21 "Lrp6$^{+/-}$" should be -- LRP6$^{+/-}$ --.
line 26 "gland," should be -- gland), --.
line 34 "Lrp6$^{-/-}$" should be -- LRP6$^{-/-}$ --.
line 52 "Lrp6$^{+/-}$" should be -- LRP6$^{+/-}$ --.
line 55 "Lrp6$^{+/-}$" should be -- LRP6$^{+/-}$ --.
line 56 "Lrp6" should be -- LRP6 --.
line 57 "Lrp6$^{+/-}$" should be -- LRP6$^{+/-}$ --.
line 62 "LRp6" should be -- LRP6 --.
line 65 "Lrp6" should be -- LRP6 --.

Column 37
line 6 "Lrp5" should be -- LRP5 --.
line 8 "Bat-Gal" should be -- BAT-gal --.
line 13 "Lip5$^{-/-}$" should be -- LRP5$^{-/-}$ --.
line 16 "Lrp5$^{-/-}$" should be -- LRP5$^{-/-}$ --.
line 19 "Lrp5$^{-/-}$" should be -- LRP5$^{-/-}$ --.
line 22 "Lrp5$^{-/-}$" should be -- LRP5$^{-/-}$, --.

Column 65
claim 1, lines 3-4 "of mammary cells mammary tumor" should be -- of mammary cells or mammary tumor --.
claim 3, line 15 "compound of claim 1 wherein" should be -- method of claim 1, wherein --.
claim 4, line 17 "claim 1 wherein" should be -- claim 1, wherein --.